United States Patent
Lian et al.

(10) Patent No.: US 10,556,888 B2
(45) Date of Patent: Feb. 11, 2020

(54) PYRAZOLE COMPOUNDS OR SALTS THEREOF, PREPARATION METHODS THEREFOR, HERBICIDAL COMPOSITIONS AND USE THEREOF

(71) Applicant: QINGDAO KINGAGROOT CHEMICAL COMPOUNDS CO., LTD, Shinan District, Qingdao, Shandong (CN)

(72) Inventors: Lei Lian, Shandong (CN); Yurong Zheng, Shandong (CN); Song Li, Shandong (CN); Xuegang Peng, Shandong (CN); Tao Jin, Shandong (CN); Qi Cui, Shandong (CN)

(73) Assignee: QINGDAO KINGAGROOT CHEMICAL COMPOUNDS CO., LTD., Shinan District (CN)

( * ) Notice: Subject to any disclaimer, the term of this patent is extended or adjusted under 35 U.S.C. 154(b) by 0 days.

(21) Appl. No.: 15/561,394

(22) PCT Filed: Mar. 4, 2016

(86) PCT No.: PCT/CN2016/075578
§ 371 (c)(1),
(2) Date: Sep. 25, 2017

(87) PCT Pub. No.: WO2017/113509
PCT Pub. Date: Jul. 6, 2017

(65) Prior Publication Data
US 2018/0105513 A1    Apr. 19, 2018

(30) Foreign Application Priority Data
Dec. 31, 2015 (CN) .......................... 2015 1 1030154

(51) Int. Cl.
*A01N 43/56* (2006.01)
*C07D 403/14* (2006.01)
*C07D 231/20* (2006.01)
*C07D 405/14* (2006.01)
*C07D 403/12* (2006.01)

(52) U.S. Cl.
CPC ........... *C07D 403/14* (2013.01); *A01N 43/56* (2013.01); *C07D 231/20* (2013.01); *C07D 403/12* (2013.01); *C07D 405/14* (2013.01)

(58) Field of Classification Search
CPC ............................. A01N 43/56; C07D 403/12
See application file for complete search history.

(56) References Cited

U.S. PATENT DOCUMENTS

| | | |
|---|---|---|
| 4,948,887 A | 8/1990 | Baba et al. |
| 6,156,702 A | 12/2000 | Engel et al. |
| 6,165,944 A | 12/2000 | Von Deyn et al. |

FOREIGN PATENT DOCUMENTS

| | | |
|---|---|---|
| CN | 88101455 A | 9/1988 |
| CN | 103980202 A | 8/2014 |
| EP | 2106697 A1 | 10/2009 |
| JP | S63-122673 A | 5/1988 |
| JP | 2008-081406 A | 4/2008 |
| WO | WO 98/42648 A1 | 10/1998 |
| WO | WO 00/03993 A1 | 1/2000 |

OTHER PUBLICATIONS

Australian Patent Office, Office Action in counterpart Australian Application No. 2016382562, dated Jun. 28, 2018.
Russian Patent Office, Office Action in counterpart Russian Application No. 2018110616, dated Dec. 3, 2018.
Russian Patent Office, Search Report in counterpart Russian Application No. 2018110616, dated Dec. 3, 2018.
Indian Patent Office, Office Action in counterpart Indian Application No. 201747035236, dated Jun. 17, 2019.

*Primary Examiner* — Johann R Richter
*Assistant Examiner* — Danielle Sullivan
(74) *Attorney, Agent, or Firm* — Leydig Voit & Mayer, Ltd.

(57) ABSTRACT

The present invention relates to the technical field of pesticides, particularly relates to a pyrazole compound or a salt thereof, a preparation method therefor, a herbicidal composition and use thereof. A pyrazole compound of formula (I) or a salt thereof:

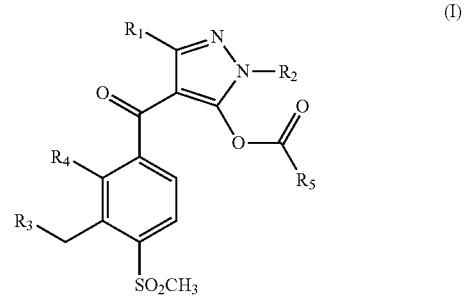

wherein, $R_1$ represents hydrogen or C1-C4 alkyl; $R_2$ represents C1-C3 alkyl; $R_3$ represents C1-C6 linear chain or cyclic group containing one or more heteroatoms selected from O, S, and N; $R_4$ represents C1-C3 alkyl or halogen; $R_5$ represents pyrazole ring or pyrazole ring substituted with one or more groups selected from alkyl, alkoxyl, halogen, halogenated alkyl, amino, and nitro. The pyrazole compound is an excellent herbicide with broad spectrum biological activity and outstanding safety for crops.

13 Claims, No Drawings

PYRAZOLE COMPOUNDS OR SALTS THEREOF, PREPARATION METHODS THEREFOR, HERBICIDAL COMPOSITIONS AND USE THEREOF

CROSS-REFERENCE TO RELATED APPLICATIONS

This patent application is the U.S. National Stage of International Application No. PCT/CN2016/075578, filed Mar. 4, 2016, which claims the benefit of Chinese Application No. 201511030154.6, filed Dec. 31, 2015, which are each incorporated by reference.

TECHNICAL FIELD

The present invention relates to the technical field of pesticides, particularly relates to a pyrazole compound or a salt thereof, a preparation method therefor, a herbicidal composition and use thereof.

TECHNICAL BACKGROUND

Weed control is one of the most important links in the course of achieving high-efficiency agriculture. Although various herbicides are available in the market, scientists still need to do continuously research and develop new herbicides with high efficacy, safety, economics and different modes of action due to problems such as the growing market, weed resistance, the service life and economics of pesticides as well as people's increasing concern on environment. There are many researches on pyrazole compounds, for example, CN88101455A discloses a series of pyrazole compounds containing a pyrazole ring in the general structure, but the compounds have some defects in safety and activity.

INVENTION CONTENTS

In order to design and synthesize herbicidal compounds with higher efficacy, broader activity spectrum and better safety, through molecular design and optimization, the present invention synthesized a novel pyrazole compound containing at least two pyrazole rings which can be used as herbicidal active ingredient. The compound has more outstanding activity and better safety for crops.

In order to achieve the above purpose, the present invention provide the following technical solution:

A pyrazole compound of formula (I) or a salt thereof:

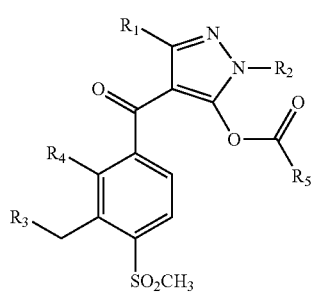

(I)

wherein,
$R_1$ represents hydrogen or C1-C4 alkyl;
$R_2$ represents C1-C3 alkyl;
$R_3$ represents C1-C6 linear or cyclic group containing one or more heteroatoms selected from O, S, and N;
$R_4$ represents C1-C3 alkyl or halogen;
$R_5$ represents pyrazole ring or pyrazole ring substituted with one or more groups selected from alkyl, alkoxyl, halogen, halogenated alkyl, amino, and nitro.

Preferably, the structure of the pyrazole compound or the salt thereof is shown as follows:

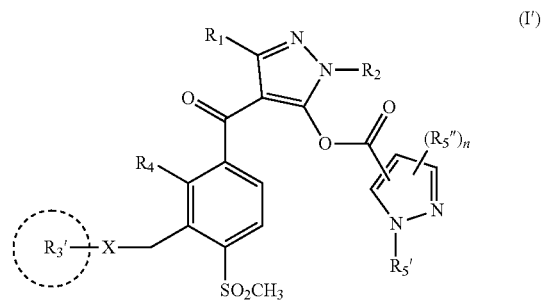

(I')

wherein,
$R_1$ represents hydrogen or C1-C4 alkyl;
$R_2$ represents C1-C3 alkyl;
X represents O, N or S, X and $R_3'$ may form a ring or a linear chain, wherein, when X is O or S, $R_3'$ represents C1-C6 alkyl, C3-C6 alkoxyl alkyl, C2-C6 halogenated alkyl, C3-C6 alkenyl or C3-C6 alkynyl; when X is N, X and $R_3'$ form a pyrazole ring or substituted pyrazole ring, C3-C5 lactam ring or substituted lactam ring.
$R_4$ represents C1-C3 alkyl or halogen;
$R_5'$ represents C1-C3 alkyl;
$R_5''$ represents hydrogen, C1-C3 alkyl, C1-C3 alkoxyl, C1-C3 halogenated alkyl, halogen, amino or nitro; n is 0, 1 or 2, wherein, when n is 2, the two $R_5''$ may be the same or different.

More preferably, $R_1$ represents hydrogen, methyl, ethyl or cyclopropyl;
$R_2$ represents methyl, ethyl or isopropyl;
X represents O, N or S, X and $R_3'$ may form a ring or a linear chain, wherein, when X is O or S, $R_3'$ represents C1-C6 alkyl, C3-C6 alkoxyl alkyl, C2-C4 halogenated alkyl, C3-C5 alkenyl or C3-C5 alkynyl; when X is N, X and $R_3'$ form a pyrazole ring or substituted pyrazole ring, C3-C5 lactam ring or substituted lactam ring.
$R_4$ represents methyl or chlorine;
$R_5'$ represents methyl, ethyl or isopropyl;
$R_5''$ represents hydrogen, methyl, ethyl, isopropyl, methoxyl, ethoxyl, difluoromethyl, chloro or bromo; n is 0, 1 or 2, wherein, when n is 2, the two $R_5''$ may be the same or different.

Most preferably, X represents O or N, X and $R_3'$ may form a ring or a linear chain, wherein, when X is O, $R_3'$ represents methyl, ethyl, n-butyl, methoxyl ethyl, ethoxyl ethyl, methoxyl isopropyl, methoxyl n-propyl, 2,2-difluoroethyl, 2,2,2-trifluoroethyl, 1,1,2,2-tetrafluoropropyl, propargyl, 2-alkene butyl or tetrahydrofurfuryl; when X is N, X and $R_3'$ form a pyrazole ring, 3-methyl pyrazole ring, 4-methyl pyrazole ring, 3,5-dimethyl pyrazole ring, 4-chloropyrazole ring or pyrrolidone ring.

In the definition of the above mentioned compound of formula (I), the terms used, either alone or in combine with other terms, represent the following substituent groups:
Halogen: refers to fluorine, chlorine, bromine, and iodine;
Alkyl: refers to linear alkyl or branched alkyl;

Halogenated alkyl: refers to a linear or branched alkyl with all or part of the hydrogen substituted with halogen atom;

Alkoxyl: refers to a functional group formed by connecting an alkyl with an oxygen atom.

A method for preparing the pyrazole compound of formula (I) or the salt thereof, comprising a step of subjecting a compound of formula (II) and a compound of formula (III) to an esterification reaction to obtain the pyrazole compound of formula (I) or the salt thereof, wherein, the compound of formula (II) is shown as follows:

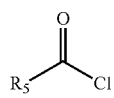
(II)

the compound of formula (III) is shown as follows:

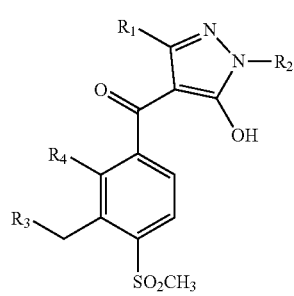
(III)

and the detailed reaction route is shown as follows:

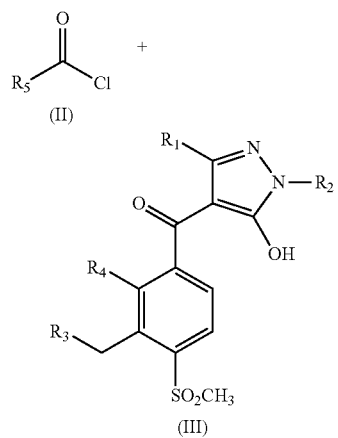

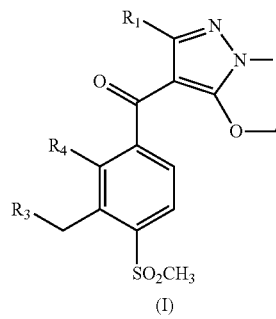
(I)

A method for preparing the pyrazole compound of formula (I') or the salt thereof, comprising a step of subjecting a compound of formula (II') and a compound of formula (III') to an esterification reaction to obtain the pyrazole compound of formula (I') or the salt thereof, wherein, the compound of formula (II') is shown as follows:

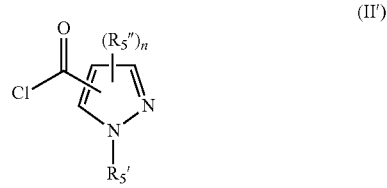
(II')

the compound of formula (III') is shown as follows:

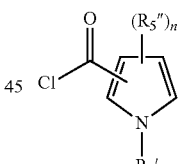
(III')

and the detailed reaction route is shown as follows:

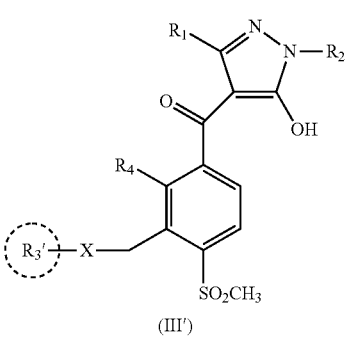
(III')

-continued

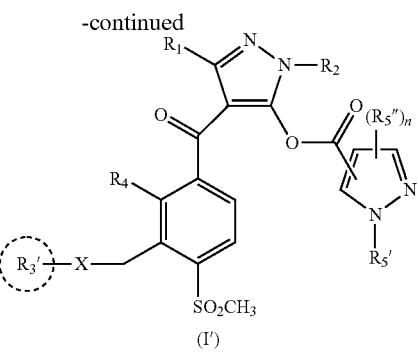

The compound of formula (II') can be prepared by reacting a corresponding carboxylic acid (that is, a compound of formula (II-1)) with sulfoxide chloride. The compound of formula (II-1) is shown as follows:

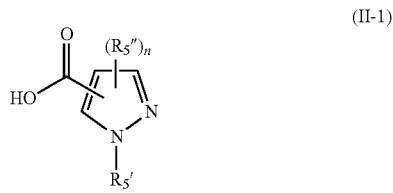

The structure as shown in formula (II-1) is the structure of pyrazolecarboxylic acid. The formula indicates that such pyrazolecarboxylic acid may be 3-pyrazolecarboxylic acid or substituted 3-pyrazolecarboxylic acid, 4-pyrazolecarboxylic acid or substituted 4-pyrazolecarboxylic acid, or 5-pyrazolecarboxylic acid or substituted 5-pyrazolecarboxylic acid.

The esterification reaction in the above mentioned reaction route needs to be conducted in the presence of a solvent. The solvent used should be those inert to the reaction. Such solvent is generally an aprotic solvent, which is either polar or non-polar, for example, acetonitrile, methylbenzene, dimethylbenzene, dichloromethane, dichloroethane, tetrahydrofuran, acetone, etc., preferably acetonitrile or dichloromethane.

The above mentioned esterification reaction should to be conducted in the presence of a deacid reagent; the deacid reagent used is usually an alkali, which is either inorganic or organic. One or more of such alkalis could be selected for use from carbonates (e.g. sodium carbonate, potassium carbonate), bicarbonates (e.g. sodium bicarbonate, potassium bicarbonate), amines (e.g. dimethylamine, triethylamine, N,N-diisopropylethylamine), and pyridines (e.g. pyridine, 4-dimethylaminopyridine), preferably triethylamine or potassium carbonate.

The reaction temperature of the above mentioned esterification reaction is generally between −10 to 50° C., preferably 0 to 20° C.; the reaction time is between 0.1 to 12 hours, preferably 0.5 to 3 hours.

The compound of the present invention may exist in a form of one or multiple stereoisomers. The stereoisomer includes enantiomer, diastereoisomer and geometric isomer. All of these stereoisomers and mixture thereof are within the scope of the present invention.

Also disclosed is a herbicidal composition which comprises a herbicidally effective amount of at least one pyrazole compound or the salt thereof.

The herbicidal composition also comprises a preparation auxiliary.

Also disclosed is a method for controlling a harmful plant, which comprises a step of applying a herbicidally effective amount of at least one pyrazole compound or the salt thereof or the herbicidal composition to the plant or an area with the harmful plant.

Use of at least one pyrazole compound or the salt thereof or the herbicidal composition in controlling a harmful plant, preferably, the pyrazole compound or the salt thereof is applied to control the harmful plant in a desirable crop, preferably, the desirable crop is a genetically modified crop or a crop treated by a genome editing technique.

The compounds of the formula (I) according to the invention have an outstanding herbicidal activity against a broad spectrum of economically important monocotyledonous and dicotyledonous harmful plants. The active compounds also act efficiently on perennial weeds which produce shoots from rhizomes, root stocks or other perennial organs and which are difficult to control. In this context, it is generally immaterial whether the substances are applied pre-sowing, pre-emergence or post-emergence. Specifically, examples may be mentioned of some representatives of the monocotyledonous and dicotyledonous weed flora which can be controlled by the compounds according to the invention, without these being a restriction to certain species. Examples of weed species on which the active compounds act efficiently are, from amongst the monocotyledons, *Avena*, *Lolium*, *Alopecurus*, *Phalaris*, *Echinochloa*, *Digitaria*, *Setaria* and also *Cyperus* species from the annual sector and from amongst the perennial species *Agropyron*, *Cynodon*, *Imperata* and *Sorghum*, and also perennial *Cyperus* species.

In the case of the dicotyledonous weed species, the spectrum of action extends to species such as, for example, *Galium*, *Viola*, *Veronica*, *Lamium*, *Stellaria*, *Amaranthus*, *Sinapis*, *Ipomoea*, *Sida*, *Matricaria* and *Abutilon* from amongst the annuals, and *Convolvulus*, *Cirsium*, *Rumex* and *Artemisia* in the case of the perennial weeds. The active compounds according to the invention also effect outstanding control of harmful plants which occur under the specific conditions of rice growing such as, for example, *Echinochloa*, *Sagittaria*, *Alisma*, *Eleocharis*, *Scirpus* and *Cyperus*. If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely. If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely. In particular, the compounds according to the invention exhibit excellent activity against *Apera spica venti*, *Chenopodium album*, *Lamium purpureum*, *Polygonum convulvulus*, *Stellaria media*, *Veronica hederifolia*, *Veronica persica*, *Viola tricolor* and against *Amaranthus*, *Galium* and *Kochia* species.

Although the compounds according to the invention have an excellent herbicidal activity against monocotyledonous and dicotyledonous weeds, crop plants of economically important crops such as, for example, wheat, barley, rye, rice, corn, sugarbeet, cotton and soya, are not damaged at all, or only to a negligible extent. In particular, they have excellent compatibility in cereals, such as wheat, barley and corn, in particular wheat. For these reasons, the present compounds are highly suitable for selectively controlling undesired plant growth in plantings for agricultural use or in plantings of ornamentals.

Owing to their herbicidal properties, these active compounds can also be employed for controlling harmful plants in crops of known or still to be developed genetically engineered plants. The transgenic plants generally have particularly advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested produce are known.

The use of the compounds of the formula (I) according to the invention or their salts in economically important transgenic crops of useful and ornamental plants, for example of cereal, such as wheat, barley, rye, oats, millet, rice, maniok and corn, or else in crops of sugarbeet, cotton, soya, rapeseed, potato, tomato, pea and other vegetable species is preferred. The compounds of the formula (I) can preferably be used as herbicides in crops of useful plants which are resistant or which have been made resistant by genetic engineering toward the phytotoxic effects of the herbicides.

Conventional ways for preparing novel plants which have modified properties compared to known plants comprise, for example, traditional breeding methods and the generation of mutants. Alternatively, novel plants having modified properties can be generated with the aid of genetic engineering methods (see, for example, EP-A 0 221 044, EP-A 0 131 624). For example, there have been described several cases of genetically engineered changes in crop plants in order to modify the starch synthesized in the plants (for example WO 92/11376, WO 92/14827, WO 91/19806), transgenic crop plants which are resistant to certain herbicides of the glufosinate (Glufosinate ammonium)- (cf., for example, EP-A 0 242 236, EP-A 0 242 246) or glyphosate-type (WO 92/00377), or of the sulfonylurea-type (EP-A 0 257 993, U.S. Pat. No. 5,013,659), transgenic crop plants, for example cotton, having the ability to produce *Bacillus thuringiensis* toxins (Bt toxins) which impart resistance to certain pests to the plants (EP-A 0 142 924, EP-A 0 193 259), transgenic crop plants having a modified fatty acid composition (WO 91/13972).

Numerous molecular biological techniques which allow the preparation of novel transgenic plants having modified properties are known in principle; see, for example, Sambrook et al., 1989, Molecular Cloning, A Laboratory Manual, 2nd ed. Cold Spring Harbor Laboratory Press, Cold Spring Harbor, N.Y.; or Winnacker "Gene und Klone" [Genes and Clones], VCH Weinheim, 2nd edition 1996, or Christou, "Trends in Plant Science" 1 (1996) 423-431). In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the abovementioned gene product.

To this end it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cells. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated to whole plants using known techniques. The transgenic plants can in principle be plants of any desired plant species, i.e. both monocotyledonous and dicotyledonous plants. In this manner, it is possible to obtain transgenic plants which have modified properties by overexpression, suppression or inhibition of homologous (=natural) genes or gene sequences or by expression of heterologous (=foreign) genes or gene sequences.

When using the active compounds according to the invention in transgenic crops, in addition to the effects against harmful plants which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crops are resistant, and an effect on the growth and the yield of the transgenic crop plants. The invention therefore also provides for the use of the compounds according to the invention as herbicides for controlling harmful plants in transgenic crop plants.

In addition, the substances according to the invention have outstanding growth-regulating properties in crop plants. They engage in the plant metabolism in a regulating manner and can this be employed for the targeted control of plant constituents and for facilitating harvesting, for example by provoking desiccation and stunted growth. Furthermore, they are also suitable for generally regulating and inhibiting undesirable vegetative growth, without destroying the plants in the process. Inhibition of vegetative growth plays an important role in many monocotyledon and dicotyledon crops because lodging can be reduced hereby, or prevented completely.

The compounds according to the invention can be applied in the customary formulations in the form of wettable powders, emulsifiable concentrates, sprayable solutions, dusts or granules. The invention therefore also provides herbicidal compositions comprising compounds of the formula (I). The compounds of the formula (I) can be formulated in various ways depending on the prevailing biological and/or chemico-physical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, dusts (DP), capsule suspensions (CS), seed-dressing compositions, granules for broadcasting and soil application, granules (GR) in the form of microgranules, spray granules, coating granules and adsorption granules, water-dispersible granules (WG), water-soluble granules (SG), ULV formulations, microcapsules and waxes. These individual formulation types are known in principle and are described, for example, in Winnacker-Kuhler, "Chemische Technologie" [Chemical Technology], Volume 7, C. Hauser Verlag Munich, 4th. Edition 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries, such as inert materials, surfactants, solvents and other additives, are likewise known and are described, for example, in Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schonfeldt, "Grenzflchenaktive thylenoxidaddukte" [Surface-active ethylene oxide adducts], Wiss. Verlagsgesell, Stuttgart 1976; Winnacker-Kuchler, "Chemische Technologie" [Chemical Technology], Volume 7, C. Hauser Verlag Munich, 4th Edition 1986.

Wettable powders are preparations which are uniformly dispersible in water and which contain, in addition to the active compound and as well as a diluent or inert substance, surfactants of ionic and/or nonionic type (wetting agents, dispersants), for example polyethoxylated alkyl phenols, polyethoxylated fatty alcohols, polyethoxylated fatty amines, fatty alcohol polyglycol ethersulfates, alkanesulfonates, alkylbenzenesulfonates, sodium ligninsulfonate, sodium 2,2'-dinaphthylmethane-6,6'-disulfonate, sodium dibutyinaphthalenesulfona-te or else sodium oleoylmethyltaurinate. To prepare the wettable powders, the herbicidally active compounds are finely ground, for example in customary apparatus such as hammer mills, fan mills and air-jet mills, and are mixed simultaneously or subsequently with the formulation auxiliaries.

Emulsifiable concentrates are prepared by dissolving the active compound in an organic solvent, for example butanol, cyclohexanone, dimethylformamide, xylene or else relatively high-boiling aromatic compounds or hydrocarbons or mixtures of the solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth. Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers. Water-dispersible granules are generally prepared by the customary processes, such as spray-drying, fluidized-bed granulation, disk granulation, mixing using high-speed mixers, and extrusion without solid inert material.

For the preparation of disk, fluidized-bed, extruder and spray granules, see for example processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8-57. For further details on the formulation of crop protection products, see for example G. C. Klingman, "Weed Control as a Science", John Wiley and Sons Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations generally contain from 0.1 to 99% by weight, in particular from 0.1 to 95% by weight, of active compound of the formula (I). In wettable powders the concentration of active compound is, for example, from about 10 to 90% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably most commonly from 5 to 20% by weight of active compound, while sprayable solutions contain from about 0.05 to 80%, preferably from 2 to 50%, by weight of active compound. In the case of water-dispersible granules the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, said formulations of active compound may comprise the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

Based on these formulations it is also possible to produce combinations with other pesticidally active substances, for example insecticides, acaricides, herbicides and fungicides, and also with safeners, fertilizers and/or growth regulators, for example in the form of a ready-mix or tank mix.

Suitable active compounds which can be combined with the active compounds according to the invention in mixed formulations or in a tank mix are, for example, known active compounds as described in for example *World Herbicide New Product Technology Handbook*, China Agricultural Science and Farming Techniques Press, 2010.9 and in the literature cited therein. For example the following active compounds may be mentioned as herbicides which can be combined with the compounds of the formula (I) (note: the compounds are either named by the "common name" in accordance with the International Organization for Standardization (ISO) or by the chemical names, if appropriate together with a customary code number): acetochlor, butachlor, alachlor, propisochlor, metolachlor, s-metolachlor, pretilachlor, propachlor, ethachlor, napropamide, R-left handed napropamide, propanil, mefenacet, diphenamid, diflufenican, ethaprochlor, beflubutamid, bromobutide, dimethenamid, dimethenamid-P, etobenzanid, flufenacet, thenylchlor, metazachlor, isoxaben, flamprop-M-methyl, flamprop-M-propyl, allidochlor, pethoxamid, chloranocryl, cyprazine, mefluidide, monalide, delachlor, prynachlor, terbuchlor, xylachlor, dimethachlor, cisanilide, trimexachlor, clomeprop, propyzamide, pentanochlor, carbetamide, benzoylprop-ethyl, cyprazole, butenachlor, tebutam, benzipram, 1379, dichlofluanid, naproanilide, diethatyl-ethyl, naptalam, flufenacet, benzadox, chlorthiamid, chlorophthalimide, isocarbamide, picolinafen, atrazine, simazine, prometryn, cyanatryn, simetryn, ametryn, propazine, dipropetryn, SSH-108, terbutryn, terbuthylazine, triaziflam, cyprazine, proglinazine, trietazine, prometon, simetone, aziprotryne, desmetryn, dimethametryn, procyazine, mesoprazine, sebuthylazine, secbumeton, terbumeton, methoprotryne, cyanatryn, ipazine, chlorazine, atraton, pendimethalin, eglinazine, cyanuric acid, indaziflam, chlorsulfuron, metsulfuron-methyl, bensulfuron methyl, chlorimuron-ethyl, tribenuron-methyl, thifensulfuron-methyl, pyrazosulfuron-ethyl, mesosulfuron, iodosulfuron-methyl sodium, foramsulfuron, cinosulfuron, triasulfuron, sulfometuron methyl, nicosulfuron, ethametsulfuron-methyl, amidosulfuron, ethoxysulfuron, cyclosulfamuron, rimsulfuron, azimsulfuron, flazasulfuron, monosulfuron, monosulfuron-ester, flucarbazone-sodium, flupyrsulfuron-methyl, halosulfuron-methyl, oxasulfuron, imazosulfuron, primisulfuron, propoxycarbazone, prosulfuron, sulfosulfuron, trifloxysulfuron, triflusulfuron-methyl, tritosulfuron, sodium metsulfuron methyl, flucetosulfuron, HNPC-C, orthosulfamuron, propyrisulfuron, metazosulfuron, acifluorfen, fomesafen, lactofen, fluoroglycofen, oxyfluorfen, chlornitrofen, aclonifen, ethoxyfen-ethyl, bifenox, nitrofluorfen, chlomethoxyfen, fluorodifen, fluoronitrofen, furyloxyfen, nitrofen, TOPE, DMNP, PPG1013, AKH-7088, halosafen, chlortoluron, isoproturon, linuron, diuron, dymron, fluometuron, benzthiazuron, methabenzthiazuron, cumyluron, ethidimuron, isouron, tebuthiuron, buturon, chlorbromuron, methyldymron, phenobenzuron, SK-85, metobromuron, metoxuron, afesin, monuron, siduron, fenuron, fluothiuron, neburon, chloroxuron, noruron, isonoruron, 3-cyclooctyl-1, thiazfluron, tebuthiuron, difenoxuron, parafluron, methylamine tribunil, karbutilate, trimeturon, dimefuron, monisouron, anisuron, methiuron, chloreturon, tetrafluron, phenmedipham, phenmedipham-ethyl, desmedipham, asulam, terbucarb, barban, propham, chlorpropham, rowmate, swep, chlorbufam, carboxazole, chlorprocarb, fenasulam, BCPC, CPPC, carbasulam, butylate, benthiocarb, vernolate, molinate, triallate, dimepiperate, esprocarb, pyributicarb, cycloate, avadex, EPTC, ethiolate, orbencarb, pebulate, prosulfocarb, tiocarbazil, CDEC, dimexano, isopolinate, methiobencarb, 2,4-D butyl ester, MCPA-Na, 2,4-D isooctyl ester, MCPA isooctyl ester, 2,4-D sodium salt, 2,4-D dimethyla mine salt, MCPA-thioethyl, MCPA, 2,4-D propionic acid, high 2,4-D propionic acid salt, 2,4-D butyric acid, MCPA propionic acid, MCPA propionic acid salt, MCPA butyric acid, 2,4,5-D, 2,4,5-D propionic acid, 2,4,5-D butyric acid, MCPA amine salt, dicamba, erbon, chlorfenac, saison, TBA, chloramben, methoxy-TBA, diclofop-methyl, fluazifop-butyl, fluazifop-p-butyl, haloxyfop-methyl, haloxyfop-P, quizalofop-ethyl, quizalofop-p-ethyl, fenoxaprop-ethy, fenoxaprop-p-ethyl, propaquizafop, cyhalofop-butyl, metamifop, clodinafop-propargyl, fenthiaprop-ethyl, chloroazifop-propynyl, poppenate-methyl, trifopsime, isoxapyrifop, paraquat, diquat, oryzalin, ethalfluralin, isopropalin, nitralin, profluralin, prodinamine, benfluralin, fluchloraline, dinitramina, dipropalin, chlornidine, methalpropalin, dinoprop, glyphosate, anilofos, glufosinate ammonium, amiprophos-methyl, sulphosate, piperophos, bialaphos-sodium, bensulide, butamifos, phocarb, 2,4-DEP, H-9201, zytron, imazapyr, imazethapyr, imazaquin, imazamox, imazamox ammonium salt, imazapic, imazamethabenz-methyl, fluroxypyr, fluroxypyr isooctyl ester, clopyralid, picloram, trichlopyr, dithiopyr, haloxydine, 3,5,6-trichloro-2-pyridinol, thiazopyr, fluridone, aminopyralid, diflufenzopyr, triclopyr-butotyl, Cliodinate, sethoxydim, clethodim, cycloxydim, alloxydim, clefoxydim, butroxydim, tralkoxydim, tepraloxydim, buthidazole, metribuzin, hexazinone, metamitron, ethiozin, ametridione, amibuzin, bromoxynil, bromoxynil octanoate, ioxynil octanoate, ioxynil, dichlobenil, diphenatrile, pyraclonil, chloroxynil, iodobonil, flumetsulam, florasulam, penoxsulam, metosulam, cloransulam-methyl, diclosulam, pyroxsulam, benfuresate, bispyribac-sodium, pyribenzoxim, pyriftalid, pyriminobac-methyl, pyrithiobac-sodium, benzobicylon, mesotrione, sulcotrione, tembotrione, tefuryltrione, bicyclopyrone, ketodpiradox, isoxaflutole, clomazone, fenoxasulfone, methiozolin, fluazolate, pyraflufen-ethyl, pyrazolynate, difenzoquat, pyrazoxyfen, benzofenap, nipyraclofen, pyrasulfotole, topramezone, pyroxasulfone, cafenstrole, flupoxam, aminotriazole, amicarbazone, azafenidin, carfentrazone-ethyl, sulfentrazone, bencarbazone, benzfendizone, butafenacil, bromacil, isocil, lenacil, terbacil, flupropacil, cinidon-ethyl, flumiclorac-pentyl, flumioxazin, propyzamide, MK-129, flumezin, pentachlorophenol, dinoseb, dinoterb, dinoterb acetate, dinosam, DNOC, chloronitrophene, medinoterb acetate, dinofenate, oxadiargyl, oxadiazon, pentoxazone, Flufenacet, fluthiacet-methyl, fentrazamide, flufenpyr-ethyl, pyrazon, brompyrazon, metflurazon, kusakira, dimidazon, oxapyrazon, norflurazon, pyridafol, quinclorac, quinmerac, bentazone, pyridate, oxaziclomefone, benazolin, clomazone, cinmethylin, ZJ0702, pyribambenz-propyl, indanofan, sodium chlorate, dalapon, trichloroacetic acid, monochloroacetic acid, hexachloroacetone, flupropanate, cyperquat, bromofenoxim, epronaz, methazole, flurtamone, benfuresate, ethofumesate, tioclorim, chlorthal, fluorochloridone, tavron, acrolein, bentranil, tridiphane, chlorfenpropmethyl, thidiarizonaimin, phenisopham, busoxinone, methoxyphenone, saflufenacil, clacyfos, chloropon, alorac, diethamquat, etnipromid, iprymidam, ipfencarbazone, thiencarbazone-methyl, pyrimisulfan, chlorflurazole, tripropindan, sulglycapin, prosulfalin, cambendichlor, aminocyclopyrachlor, rodethanil, benoxacor, fenclorim, flurazole, fenchlorazole-ethyl, cloquintocet-mexyl, oxabetrinil, MG/91, cyometrinil, DKA-24, mefenpyr-diethyl, furilazole, fluxofenim, isoxadifen-ethyl, dichlormid, halauxifen-methyl, DOW848, UBH-509, D489, LS 82-556, KPP-300, NC-324, NC-330, KH-218, DPX-N8189, SC-0744, DOWC0535, DK-8910, V-53482, PP-600, MBH-001, KIH-9201, ET-751, KIH-6127 and KIH-2023.

For use, the formulations which are present in commercially available form are, if appropriate, diluted in the customary manner, for example using water in the case of wettable powders, emulsifiable concentrates, dispersions and water-dispersible granules. Products in the form of dusts, granules for soil application or broadcasting and sprayable solutions are usually not further diluted with other inert substances prior to use. The application rate of the compounds of the formula (I) required varies with the external conditions, such as temperature, humidity, the nature of the herbicide used and the like. It can vary within wide limits, for example between 0.001 and 1.0 kg/ha or more of active substance, but it is preferably between 0.005 and 750 g/ha, in particular between 0.005 and 250 g/ha.

In view of economics, variety and biological activity of a compound, we preferably synthesized several compounds, part of which are listed in the following table. The structure and information of a certain compound are shown in Table 1. The compounds in Table 1 are listed for further explication of the present invention, other than any limit therefor. The subject of the present invention should not be interpreted by those skilled in the art as being limited to the following compounds. The physical property data related to the present invention have not been calibrated.

TABLE 1

COMPOUND STRUCTURES AND $^1$H NMR DATA (I)

| NO. | $R_1$ | $R_2$ | $R_3$ | $R_4$ | $R_5$ | $^1$H NMR |
|---|---|---|---|---|---|---|
| 01 | —CH$_3$ | —CH$_3$ | (pyrazole) | —Cl | (methylpyrazole) | $^1$H NMR (DMSO-d$_6$, 500 MHz): δ 2.08 (s, 3H), 2.34 (s, 3H), 3.26 (s, 3H), 3.35 (s, 3H), 3.77 (s, 3H), 5.75 (s, 2H), 6.26 (s, 1H), 7.25 (s, 1H), 7.56 (s, 1H), 7.59 (d, 1H, J = 8.0 Hz), 7.91 (d, 1H, J = 8.0 Hz), 8.02 (s, 1H). |
| 02 | —CH$_3$ | —CH$_3$ | (3-methylpyrazole) | —Cl | (methylpyrazole) | $^1$H NMR (DMSO-d$_6$, 500 MHz): δ 2.09 (s, 3H), 2.29 (s, 3H), 2.37 (s, 3H), 3.15 (s, 3H), 3.58 (s, 3H), 3.77 (s, 3H), 5.76 (s, 2H), 6.29 (s, 1H), 7.55 (s, 1H), 7.58 (d, 1H, J = 8.0 Hz), 7.92 (d, 1H, J = 8.0 Hz), 8.03 (s, 1H). |
| 03 | —CH$_3$ | —CH$_3$ | (3,5-dimethylpyrazole) | —Cl | (methylpyrazole) | $^1$H NMR (DMSO-d$_6$, 500 MHz): δ 2.07 (s, 3H), 2.17 (s, 3H), 2.26 (s, 3H), 2.34 (s, 3H), 3.09 (s, 3H), 3.58 (s, 3H), 3.74 (s, 3H), 5.72 (s, 2H), 6.24 (s, 1H), 7.56 (d, 1H, J = 8.0 Hz), 7.91 (d, 1H, J = 8.0 Hz), 8.02 (s, 1H). |
| 04 | —CH$_3$ | —CH$_3$ | (4-methylpyrazole) | —Cl | (methylpyrazole) | $^1$H NMR (DMSO-d$_6$, 500 MHz): δ 1.99 (s, 3H), 2.28 (s, 3H), 2.35 (s, 3H), 3.07 (s, 3H), 3.56 (s, 3H), 3.76 (s, 3H), 5.74 (s, 2H), 7.24 (s, 1H), 7.54 (s, 1H), 7.57 (d, 1H, J = 8.0 Hz), 7.90 (d, 1H, J = 8.0 Hz), 8.00 (s, 1H). |
| 05 | —CH$_3$ | —CH$_3$ | (4-chloropyrazole) | —Cl | (methylpyrazole) | $^1$H NMR (DMSO-d$_6$, 500 MHz): δ 2.24 (s, 3H), 2.36 (s, 3H), 3.25 (s, 3H), 3.58 (s, 3H), 3.79 (s, 3H), 5.72 (s, 2H), 7.28 (s, 1H), 7.56 (d, 1H, J = 8.0 Hz), 7.93 (d, 1H, J = 8.0 Hz), 7.99 (s, 1H), 8.05 (s, 1H). |

TABLE 1-continued

COMPOUND STRUCTURES AND $^1$H NMR DATA (I)

| NO. | R$_1$ | R$_2$ | R$_3$ | R$_4$ | R$_5$ | $^1$H NMR |
|---|---|---|---|---|---|---|
| 06 | —H | —CH$_3$ | 3-methyl-1-methylpyrazol-4-yl (via CH$_2$) | —Cl | 1,3-dimethylpyrazol-4-yl | $^1$H NMR (DMSO-d$_6$, 500 MHz): δ 2.13 (s, 3H), 2.25 (s, 3H), 3.13 (s, 3H), 3.58 (s, 3H), 3.72 (s, 3H), 5.79 (s, 2H), 7.20 (s, 1H), 7.42 (s, 1H), 7.51 (s, 1H), 7.56 (d, 1H, J = 8.0 Hz), 7.95 (d, 1H, J = 8.0 Hz), 8.08 (s, 1H). |
| 07 | —H | —CH$_3$ | 4-methyl-1-methylpyrazol-3-yl (via CH$_2$) | —Cl | 1,3-dimethylpyrazol-4-yl | $^1$H NMR (DMSO-d$_6$, 500 MHz): δ 2.00 (s, 3H), 2.25 (s, 3H), 3.08 (s, 3H), 3.54 (s, 3H), 3.74 (s, 3H), 5.76 (s, 2H), 7.26 (s, 1H), 7.38 (s, 1H), 7.52 (s, 1H), 7.58 (d, 1H, J = 8.0 Hz), 7.92 (d, 1H, J = 8.0 Hz), 8.04 (s, 1H). |
| 08 | —H | —CH$_3$ | 1-methylpyrazol-5-yl (via CH$_2$) | —Cl | 1,3-dimethylpyrazol-4-yl | $^1$H NMR (DMSO-d$_6$, 500 MHz): δ 2.22 (s, 3H), 3.23 (s, 3H), 3.54 (s, 3H), 3.72 (s, 3H), 5.78 (s, 2H), 6.23 (s, 1H), 7.22 (s, 1H), 7.35 (s, 1H), 7.55 (s, 1H), 7.61 (d, 1H, J = 8.0 Hz), 7.93 (d, 1H, J = 8.0 Hz), 8.07 (s, 1H). |
| 09 | cyclopropyl | —CH$_3$ | 3-methyl-1-methylpyrazol-4-yl (via CH$_2$) | —Cl | 1,3-dimethylpyrazol-4-yl | $^1$H NMR (DMSO-d$_6$, 300 MHz): δ 0.67-1.42 (m, 4H), 2.12 (s, 3H), 2.25 (s, 3H), 2.42 (s, 1H), 3.16 (s, 3H), 3.55 (s, 3H), 3.74 (s, 3H), 5.83 (s, 2H), 6.26 (s, 1H), 7.58 (s, 1H), 7.68 (d, 1H, J = 7.8 Hz), 7.99 (d, 1H, J = 7.8 Hz), 8.11 (s, 1H). |
| 10 | cyclopropyl | —CH$_3$ | 4-chloro-1-methylpyrazol-3-yl (via CH$_2$) | —Cl | 1,3-dimethylpyrazol-4-yl | $^1$H NMR (DMSO-d$_6$, 300 MHz): δ 0.60-1.39 (m, 4H), 2.23 (s, 3H), 2.39 (s, 1H), 3.14 (s, 3H), 3.53 (s, 3H), 3.77 (s, 3H), 5.81 (s, 2H), 7.55 (s, 1H), 7.64 (d, 1H, J = 7.8 Hz), 7.93 (d, 1H, J = 7.8 Hz), 8.02 (s, 1H), 8.06 (s, 1H). |
| 11 | cyclopropyl | —CH$_3$ | 3,5-dimethyl-1-methylpyrazol-4-yl (via CH$_2$) | —Cl | 1,3-dimethylpyrazol-4-yl | $^1$H NMR (DMSO-d$_6$, 300 MHz): δ 0.65-1.40 (m, 4H), 2.07 (s, 3H), 2.18 (s, 3H), 2.27 (s, 3H), 2.45 (s, 1H), 3.21 (s, 3H), 3.58 (s, 3H), 3.77 (s, 3H), 5.88 (s, 2H), 6.26 (s, 1H), 7.66 (d, 1H, J = 7.8 Hz), 7.98 (d, 1H, J = 7.8 Hz), 8.07 (s, 1H). |

TABLE 1-continued

COMPOUND STRUCTURES AND ¹H NMR DATA

(I)

| NO. | R₁ | R₂ | R₃ | R₄ | R₅ | ¹H NMR |
|---|---|---|---|---|---|---|
| 12 | 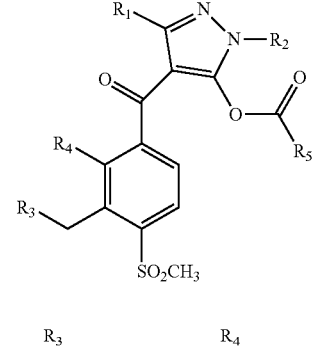 | —CH₃ | 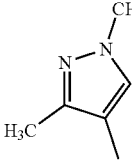 | —Cl |  | ¹H NMR (DMSO-d₆, 300 MHz): δ 0.69-1.45 (m, 4H), 1.99 (s, 3H), 2.26 (s, 3H), 2.43 (s, 1H), 3.15 (s, 3H), 3.54 (s, 3H), 3.76 (s, 3H), 5.85 (s, 2H), 6.24 (s, 1H), 7.55 (s, 1H), 7.71 (d, 1H, J = 7.8 Hz), 7.96 (d, 1H, J = 7.8 Hz), 8.08 (s, 1H). |
| 13 | 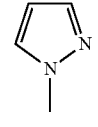 | —CH₃ | 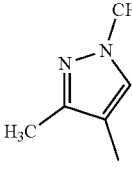 | —Cl | 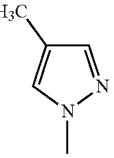 | ¹H NMR (DMSO-d₆, 300 MHz): δ 0.67-1.42 (m, 4H), 2.24 (s, 3H), 2.41(s, 1H), 3.17 (s, 3H), 3.54 (s, 3H), 3.76 (s, 3H), 5.83 (s, 2H), 6.25 (s, 1H), 7.58 (s, 1H), 7.67 (d, 1H, J = 7.8 Hz), 7.95 (d, 1H, J = 7.8 Hz), 8.05 (s, 1H), 8.10 (s, 1H). |
| 14 | —CH₃ | —CH₃ | 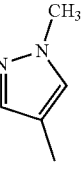 | —Cl | 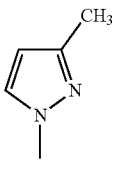 | ¹H NMR (DMSO-d₆, 500 MHz): δ 1.99 (s, 3H), 2.26 (s, 3H), 2.36 (s, 3H), 3.10 (s, 3H), 3.53 (s, 3H), 5.70 (s, 2H), 7.22 (s, 1H), 7.53 (s, 1H), 7.58 (d, 1H, J = 8.0 Hz), 7.72 (s, 1H), 7.91 (d, 1H, J = 8.0 Hz), 8.08 (s, 1H). |
| 15 | —CH₃ | —CH₃ | 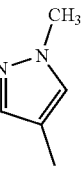 | —Cl | 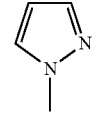 | ¹H NMR (DMSO-d₆, 500 MHz): δ 2.05 (s, 3H), 2.28 (s, 3H), 2,35 (s, 3H), 3.07 (s, 3H), 3.56 (s, 3H), 5.74 (s, 2H), 6.24 (s, 1H), 7.54 (s, 1H), 7.57 (d, 1H, J = 8.0 Hz), 7.71 (s, 1H), 7.90 (d, 1H, J = 8.0 Hz), 8.10 (s, 1H). |
| 16 | —CH₃ | —CH₃ | 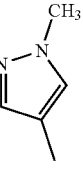 | —Cl | 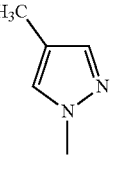 | ¹H NMR (DMSO-d₆, 500 MHz): δ2.24 (s, 3H), 2,32 (s, 3H), 3.14 (s, 3H), 3.56 (s, 3H), 5.76 (s, 2H), 6.25 (s, 1H), 7.25 (s, 1H), 7.50 (s, 1H), 7.56 (d, 1H, J = 8.0 Hz), 7.75 (s, 1H), 7.89 (d, 1H, J = 8.0 Hz), 8.09 (s, 1H). |
| 17 | —H | —CH₃ | 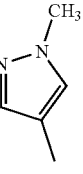 | —Cl |  | ¹H NMR (DMSO-d₆, 500 MHz): δ 1.99 (s, 3H), 2.25 (s, 3H), 3.08 (s, 3H), 3.54 (s, 3H), 5.76 (s, 2H), 7.26 (s, 1H), 7.38 (s, 1H), 7.52 (s, 1H), 7.58 (d, 1H, J = 8.0 Hz), 7.71 (s, 1H), 7.92 (d, 1H, J = 8.0 Hz), 8.04 (s, 1H). |

TABLE 1-continued

COMPOUND STRUCTURES AND $^1$H NMR DATA

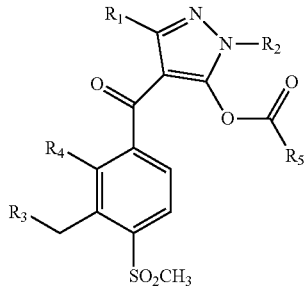

(I)

| NO. | $R_1$ | $R_2$ | $R_3$ | $R_4$ | $R_5$ | $^1$H NMR |
|---|---|---|---|---|---|---|
| 18 | cyclopropyl | —CH$_3$ | 4-chloro-1-methylpyrazol-3-yl | —Cl | 1,4-dimethylpyrazol-5-yl | $^1$H NMR (DMSO-d$_6$, 300 MHz): δ 0.68-1.42 (m, 4H), 2.18 (s, 3H), 2.37 (s, 1H), 3.16 (s, 3H), 3.59 (s, 3H), 5.88 (s, 2H), 7.52 (s, 1H), 7.66 (d, 1H, J = 7.8 Hz), 7.78 (s, 1H), 7.93 (d, 1H, J = 7.8 Hz), 8.01 (s, 1H), 8.11 (s, 1H). |
| 19 | cyclopropyl | —CH$_3$ | 1-methylpyrazol-3-yl | —Cl | 1,4-dimethylpyrazol-5-yl | $^1$H NMR (DMSO-d$_6$, 300 MHz): δ 0.71-1.48 (m, 4H), 2.20 (s, 3H), 2.36 (s, 1H), 3.15 (s, 3H), 3.64 (s, 3H), 5.87 (s, 2H), 6.35 (s, 1H), 7.50 (s, 1H), 7.62 (d, 1H, J = 7.8 Hz), 7.74 (s, 1H), 7.93 (d, 1H, J = 7.8 Hz), 8.04 (s, 1H), 8.10 (s, 1H). |
| 20 | cyclopropyl | —CH$_3$ | 1,3,5-trimethylpyrazol-4-yl | —Cl | 1,4-dimethylpyrazol-5-yl | $^1$H NMR (DMSO-d$_6$, 300 MHz): δ 0.69-1.43 (m, 4H), 2.12 (s, 3H), 2.22 (s, 3H), 2.39 (s, 1H), 3.27 (s, 3H), 3.43 (s, 3H), 3.65 (s, 3H), 5.86 (s, 2H), 6.29 (s, 1H), 7.60 (d, 1H, J = 7.8 Hz), 7.76 (s, 1H), 7.91 (d, 1H, J = 7.8 Hz), 8.08 (s, 1H). |
| 21 | cyclopropyl | —CH$_3$ | 1,3-dimethylpyrazol-5-yl | —Cl | 1,4-dimethylpyrazol-5-yl | $^1$H NMR (DMSO-d$_6$, 300 MHz): δ 0.66-1.42 (m, 4H), 2.15 (s, 3H), 2.26 (s, 3H), 2.41 (s, 1H), 3.19 (s, 3H), 3.69 (s, 3H), 5.86 (s, 2H), 6.42 (s, 1H), 7.64 (d, 1H, J = 7.8 Hz), 7.78 (s, 1H), 7.89 (d, 1H, J = 7.8 Hz), 7.98 (s, 1H), 8.09 (s, 1H). |
| 22 | cyclopropyl | —CH$_3$ | 1,4-dimethylpyrazol-5-yl | —Cl | 1,4-dimethylpyrazol-5-yl | $^1$H NMR (DMSO-d$_6$, 300 MHz): δ 0.63-1.41 (m, 4H), 1.99 (s, 3H), 2.21 (s, 3H), 2.40 (s, 1H), 3.21 (s, 3H), 3.59 (s, 3H), 5.82 (s, 2H), 7.26 (s, 1H), 7.60 (d, 1H, J = 7.8 Hz), 7.75 (s, 1H), 7.87 (d, 1H, J = 7.8 Hz), 7.99 (s, 1H), 8.09 (s, 1H). |
| 23 | —H | —CH$_3$ | 1,4-dimethylpyrazol-5-yl | —Cl | 5-ethoxy-1,4-dimethylpyrazol-5-yl | $^1$H NMR (DMSO-d$_6$, 500 MHz): δ 1.32 (t, 3H, J = 7.0 Hz), 1.99 (s, 3H), 2.25 (s, 3H), 3.08 (s, 3H), 3.54 (s, 3H), 4.32 (q, 2H, J = 7.0 Hz), 5.76 (s, 2H), 7.24 (s, 1H), 7.49 (s, 1H), 7.61 (s, 1H), 7.65 (d, 1H, J = 8.0 Hz), 7.94 (d, 1H, J = 8.0 Hz), 7.99 (s, 1H). |

TABLE 1-continued

COMPOUND STRUCTURES AND $^1$H NMR DATA

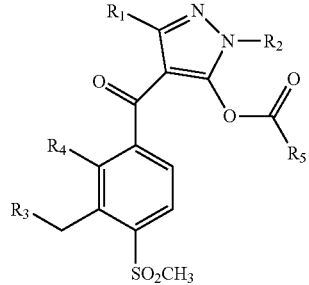

(I)

| NO. | R$_1$ | R$_2$ | R$_3$ | R$_4$ | R$_5$ | $^1$H NMR |
|-----|-------|-------|-------|-------|-------|-----------|
| 24 | —H | —CH$_3$ | ![3-methyl-1H-pyrazol-1-yl-methyl] (1-methyl-3-methylpyrazol-CH$_2$—) | —Cl | 1,4-dimethyl-5-ethoxypyrazol-yl | $^1$H NMR (DMSO-d$_6$, 500 MHz): δ 1.30 (t, 3H, J = 7.0 Hz), 2.14 (s, 3H), 2.28 (s, 3H), 3.15 (s, 3H), 3.58 (s, 3H), 4.30 (q, 2H, J = 7.0 Hz), 5.76 (s, 2H), 6.24 (s, 1H), 7.47 (s, 1H), 7.60 (s, 1H), 7.78 (d, 1H, J = 8.0 Hz), 7.96 (d, 1H, J = 8.0 Hz), 8.02 (s, 1H). |
| 25 | —CH$_3$ | —CH$_3$ | —OCH$_2$CHF$_2$ | —Cl | 1,3,4-trimethylpyrazol-5-yl | $^1$H NMR (DMSO-d$_6$, 500 MHz): δ 2.23 (s, 3H), 2.33 (s, 3H), 3.19 (s, 3H), 3.68 (s, 3H), 3.78 (s, 3H), 3.85-3.90 (td, 2H, J = 3.5 Hz, J$_{HF}$ = 15.5 Hz), 5.04 (s, 2H), 6.11-6.33 (tt, 1H, J = 3.5 Hz, J$_{HF}$ = 55 Hz), 7.63 (d, 1H, J = 8.0 Hz), 7.92 (d, 1H, J = 8.0 Hz), 8.10 (s, 1H). |
| 26 | —CH$_3$ | —CH$_3$ | —OCH$_3$ | —Cl | 1,3,4-trimethylpyrazol-5-yl | $^1$H NMR (DMSO-d$_6$, 500 MHz): δ 2.14 (s, 3H), 2.23 (s, 3H), 3.34 (s, 3H), 3.36 (s, 3H), 3.40 (s, 3H), 3.78 (s, 3H), 4.96 (s, 2H), 7.40 (d, 1H, J = 8.0 Hz), 8.01 (d, 1H, J = 8.0 Hz), 8.10 (s, 1H). |
| 27 | —CH$_3$ | —CH$_3$ | —OCH$_2$CH$_3$ | —Cl | 1,3,4-trimethylpyrazol-5-yl | $^1$H NMR (DMSO-d$_6$, 500 MHz): δ 1.14 (t, 3H, J = 7.0 Hz), 2.18 (s, 3H), 2.25 (s, 3H), 3.36 (s, 3H), 3.41 (s, 3H), 3.55 (q, 2H, J = 7.0 Hz), 3.77 (s, 3H), 4.98 (s, 2H), 7.45 (d, 1H, J = 8.0 Hz), 7.98 (d, 1H, J = 8.0 Hz), 8.06 (s, 1H). |
| 28 | —CH$_3$ | —CH$_3$ | —OCH$_2$CH$_2$OCH$_3$ | —Cl | 1,3,4-trimethylpyrazol-5-yl | $^1$H NMR (DMSO-d$_6$, 500 MHz): δ 2.12 (s, 3H), 2.23 (s, 3H), 3.18 (s, 3H), 3.38 (s, 3H), 3.49 (s, 3H), 3.50-3.58 (m, 4H), 3.72 (s, 3H), 5.04 (s, 2H), 7.55 (d, 1H, J = 8.0 Hz), 7.99 (d, 1H, J = 8.0 Hz), 8.09 (s, 1H). |
| 29 | —CH$_3$ | —CH$_3$ | —OCH$_2$CF$_3$ | —Cl | 1,3,4-trimethylpyrazol-5-yl | $^1$H NMR (DMSO-d$_6$, 500 MHz): δ 2.16 (s, 3H), 2.23 (s, 3H), 3.34 (s, 3H), 3.40 (s, 3H), 3.78 (s, 3H), 4.22 (q, 2H, J$_{HF}$ = 9.0 Hz), 4.96 (s, 2H), 7.42 (d, 1H, J = 8.0 Hz), 8.02 (d, 1H, J = 8.0 Hz), 8.11 (s, 1H). |

TABLE 1-continued

COMPOUND STRUCTURES AND $^1$H NMR DATA

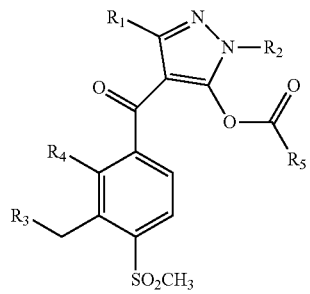

(I)

| NO. | $R_1$ | $R_2$ | $R_3$ | $R_4$ | $R_5$ | $^1$H NMR |
|---|---|---|---|---|---|---|
| 30 | —CH$_2$CH$_3$ | —CH$_3$ | 3,5-dimethyl-1-methylpyrazol-4-yl-CH$_2$- | —Cl | 1,3-dimethylpyrazol-5-yl | $^1$H NMR (DMSO-d$_6$, 500 MHz): δ 1.20 (t, 3H, J = 7.0 Hz), 2.07 (s, 3H), 2.17 (s, 3H), 2.26 (s, 3H), 2.33 (q, 2H, J = 7.0 Hz), 3.09 (s, 3H), 3.58 (s, 3H), 3.74 (s, 3H), 5.72 (s, 2H), 6.24 (s, 1H), 7.56 (d, 1H, J = 8.0 Hz), 7.91 (d, 1H, J = 8.0 Hz), 8.02 (s, 1H). |
| 31 | —CH$_2$CH$_3$ | —CH$_3$ | —OCH$_2$CH$_3$ | —Cl | 1,3-dimethylpyrazol-5-yl | $^1$H NMR (DMSO-d$_6$, 500 MHz): δ 1.14-1.28 (m, 6H), 2.18 (s, 3H), 2.36 (q, 2H, J = 7.0 Hz), 3.36 (s, 3H), 3.41 (s, 3H), 3.55 (q, 2H, J = 7.0 Hz), 3.77 (s, 3H), 4.98 (s, 2H), 7.45 (d, 1H, J = 8.0 Hz), 7.98 (d, 1H, J = 8.0 Hz), 8.06 (s, 1H). |
| 32 | —CH$_2$CH$_3$ | —CH$_3$ | —OCH$_2$CF$_3$ | —Cl | 1,3-dimethylpyrazol-5-yl | $^1$H NMR (DMSO-d$_6$, 500 MHz): δ. 1.22 (t, 3H, J = 7.0 Hz), 2.16 (s, 3H), 2.32 (q, 2H, J = 7.0 Hz), 3.34 (s, 3H), 3.40 (s, 3H), 3.78 (s, 3H), 4.22 (q, 2H, $J_{HF}$ = 9.0 Hz), 4.96 (s, 2H), 7.42 (d, 1H, J = 8.0 Hz), 8.02 (d, 1H, J = 8.0 Hz), 8.11 (s, 1H). |
| 33 | —CH$_3$ | —CH$_3$ | HC≡C—CH$_2$O— | —Cl | 1,3-dimethylpyrazol-5-yl | $^1$H NMR (DMSO-d$_6$, 500 MHz): δ 2.17 (s, 3H), 2.42 (s, 3H), 3.12 (s, 3H), 3.56 (s, 3H), 3.57 (s, 1H), 3.74 (s, 3H), 4.32 (s, 2H), 4.91 (s, 2H), 7.54 (d, 1H, J = 8.0 Hz), 7.84 (d, 1H, J = 8.0 Hz), 7.90 (s, 1H). |
| 34 | —CH$_3$ | —CH$_3$ | —OCH$_2$CH$_2$CH$_2$CH$_2$CH$_3$ | —Cl | 1,3-dimethylpyrazol-5-yl | $^1$H NMR (DMSO-d$_6$, 500 MHz): δ 0.90 (s, 3H), 1.45-1.51 (m, 4H), 2.21 (s, 3H), 2.33 (s, 3H), 3.37 (s, 3H), 3.45 (s, 3H), 3.56 (t, 2H, J = 7.0 Hz), 3.78 (s, 3H), 4.99 (s, 2H), 7.58 (d, 1H, J = 8.0 Hz), 7.96 (d, 1H, J = 8.0 Hz), 8.10 (s, 1H). |
| 35 | —CH$_3$ | —CH$_3$ | —OCH$_2$CF$_2$CHF$_2$ | —Cl | 1,3-dimethylpyrazol-5-yl | $^1$H NMR (DMSO-d$_6$, 500 MHz): δ 2.23 (s, 3H), 2.33 (s, 3H), 3.19 (s, 3H), 3.68 (s, 3H), 3.78 (s, 3H), 3.96 (t, 2H, $J_{HF}$ = 15 Hz), 5.04 (s, 2H), 5.89-6.11 (m, 1H), 7.63 (d, 1H, J = 8.0 Hz), 7.92 (d, 1H, J = 8.0 Hz), 8.11 (s, 1H). |

TABLE 1-continued

COMPOUND STRUCTURES AND $^1$H NMR DATA

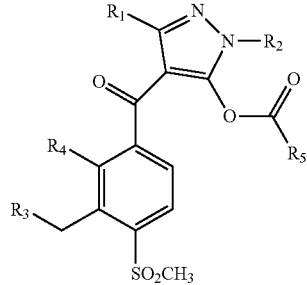

(I)

| NO. | R$_1$ | R$_2$ | R$_3$ | R$_4$ | R$_5$ | $^1$H NMR |
|---|---|---|---|---|---|---|
| 36 | —CH$_3$ | —CH$_3$ | CH$_3$OCH$_2$CHCH$_3$ (with O-methoxy branch) | —Cl | 1,3,4-trimethylpyrazol-5-yl | $^1$H NMR (DMSO-d$_6$, 500 MHz): δ 1.36 (d, 3H, J = 7.0 Hz), 2.14 (s, 3H), 2.23 (s, 3H), 3.32-3.39 (m, 4H), 3.40 (s, 3H), 3.61-3.67 (m, 5H), 3.78 (s, 3H), 4.96 (s, 2H), 7.40 (d, 1H, J = 8.0 Hz), 8.01 (d, 1H, J = 8.0 Hz), 8.10 (s, 1H). |
| 37 | —CH$_3$ | —CH$_3$ | —OCH$_2$CH$_2$OCH$_3$ | —Cl | 1,3,4-trimethylpyrazol-5-yl | $^1$H NMR (DMSO-d$_6$, 300 MHz): δ 1.09 (m, 2H), 2.25 (s, 3H), 2.40 (s, 3H), 3.18 (s, 3H), 3.45 (s, 3H), 3.53-3.67 (m, 7H), 3.85 (s, 3H), 4.921 (s, 2H), 7.51 (d, 1H, J = 7.8 Hz), 7.85 (d, 1H, J = 7.8 Hz), 8.09 (s, 1H). |
| 38 | —CH$_3$ | —CH$_3$ | H$_2$C=CH—CH$_2$O— | —Cl | 1,3,4-trimethylpyrazol-5-yl | $^1$H NMR (DMSO-d$_6$, 500 MHz): δ 1.95 (s, 3H), 2.14 (s, 3H), 2.23 (s, 3H), 3.34 (s, 3H), 3.40 (s, 3H), 3.78 (s, 3H), 3.92 (s, 2H), 4.96 (s, 2H), 5.28 (s, 1H), 5.31 (s, 1H), 7.49 (d, 1H, J = 8.0 Hz), 7.89 (d, 1H, J = 8.0 Hz), 8.08 (s, 1H). |
| 39 | —CH$_3$ | —CH$_3$ | —OCH$_2$OCH$_2$CH$_3$ | —Cl | 1,3,4-trimethylpyrazol-5-yl | $^1$H NMR (DMSO-d$_6$, 500 MHz): δ 1.10 (t, 3H, J = 7.0 Hz), 2.21 (s, 3H), 2.32 (s, 3H), 3.13 (s, 3H), 3.45 (q, 2H, J = 7.0 Hz), 3.51-3.57 (m, 4H), 3.67 (s, 3H), 3.78 (s, 3H), 5.14 (s, 2H), 7.65 (d, 1H, J = 8.0 Hz), 7.89 (d, 1H, J = 8.0 Hz), 8.04 (s, 1H). |
| 40 | —H | —CH$_3$ | —OCH$_2$CHF$_2$ | —Cl | 1,3,4-trimethylpyrazol-5-yl | $^1$H NMR (DMSO-d$_6$, 500 MHz): δ 2.23 (s, 3H), 3.19 (s, 3H), 3.68 (s, 3H), 3.78 (s, 3H), 3.85-3.90 (td, 2H, J = 3.5 Hz, J$_{HF}$ = 15.5 Hz), 5.04 (s, 2H), 6.11-6.33 (tt, 1H, J = 3.5 Hz, J$_{HF}$ = 55 Hz), 7.63 (d, 1H, J = 8.0 Hz), 7.92 (d, 1H, J = 8.0 Hz), 8.00 (s, 1H), 8.10 (s, 1H). |
| 41 | —H | —CH$_3$ | HC≡C—CH$_2$O— | —Cl | 1,3,4-trimethylpyrazol-5-yl | $^1$H NMR (DMSO-d$_6$, 500 MHz): δ 2.42 (s, 3H), 3.12 (s, 3H), 3.56 (s, 3H), 3.57 (s, 1H), 3.74 (s, 3H), 4.32 (s, 2H), 4.91 (s, 2H), 7.54 (d, 1H, J = 8.0 Hz), 7.71 (s, 1H), 7.84 (d, 1H, J = 8.0 Hz), 7.98 (s, 1H). |

TABLE 1-continued

COMPOUND STRUCTURES AND ¹H NMR DATA (I)

| NO. | R₁ | R₂ | R₃ | R₄ | R₅ | ¹H NMR |
|-----|----|----|----|----|----|--------|
| 42 | —H | —CH₃ | —OCH₂CH₃ | —Cl | (1,3-dimethyl-1H-pyrazol-5-yl) | ¹H NMR (DMSO-d₆, 500 MHz): δ 1.14 (t, 3H, J = 7.0 Hz), 2.25 (s, 3H), 3.36 (s, 3H), 3.41 (s, 3H), 3.55 (q, 2H, J = 7.0 Hz), 3.77 (s, 3H), 4.98 (s, 2H), 7.45 (d, 1H, J = 8.0 Hz), 7.63 (s, 1H), 7.98 (d, 1H, J = 8.0 Hz), 8.06 (s, 1H). |
| 43 | —H | —CH₃ | H₃C—CH=CH—CH₂O— | —Cl | (1,3-dimethyl-1H-pyrazol-5-yl) | ¹H NMR (DMSO-d₆, 500 MHz): δ 1.95 (s, 3H), 2.46 (s, 3H), 3.34 (s, 3H), 3.40 (s, 3H), 3.78 (s, 3H), 3.92 (s, 2H), 4.96 (s, 2H), 5.28 (s, 1H), 5.31 (s, 1H), 7.49 (d, 1H, J = 8.0 Hz), 7.67 (s, 1H), 7.89 (d, 1H, J = 8.0 Hz), 8.08 (s, 1H). |
| 44 | —H | —CH₃ | —OCH₂CF₃ | —Cl | (1,3-dimethyl-1H-pyrazol-5-yl) | ¹H NMR (DMSO-d₆, 500 MHz): δ 2.19 (s, 3H), 3.34 (s, 3H), 3.40 (s, 3H), 3.78 (s, 3H), 4.22 (q, 2H, J$_{HF}$ = 9.0 Hz), 4.96 (s, 2H), 7.42 (d, 1H, J = 8.0 Hz), 7.71 (s, 1H), 8.02 (d, 1H, J = 8.0 Hz), 8.11 (s, 1H). |
| 45 | —H | —CH₃ | —OCH₂CH₂OCH₂CH₃ | —Cl | (1,3-dimethyl-1H-pyrazol-5-yl) | ¹H NMR (DMSO-d₆, 500 MHz): δ 1.11 (t, 3H, J = 7.0 Hz), 2.32 (s, 3H), 3.13 (s, 3H), 3.48 (q, 2H, J = 7.0 Hz), 3.51-3.57 (m, 4H), 3.67 (s, 3H), 3.78 (s, 3H), 5.14 (s, 2H), 7.65 (d, 1H, J = 8.0 Hz), 7.89 (d, 1H, J = 8.0 Hz), 7.97 (s, 1H), 8.08 (s, 1H). |
| 46 | cyclopropyl | —CH₃ | —OCH₂CH₃ | —Cl | (1,3-dimethyl-1H-pyrazol-5-yl) | ¹H NMR (DMSO-d₆, 500 MHz): δ 0.87-1.00 (m, 4H), 1.17 (t, 3H, J = 7.0 Hz), 2.28 (s, 3H), 2.52 (s, 1H), 3.35 (s, 3H), 3.42 (s, 3H), 3.54 (q, 2H, J = 7.0 Hz), 3.72 (s, 3H), 5.01 (s, 2H), 7.45 (d, 1H, J = 8.0 Hz), 7.99 (d, 1H, J = 8.0 Hz), 8.08 (s, 1H). |
| 47 | cyclopropyl | —CH₃ | HC≡C—CH₂O— | —Cl | (1,3-dimethyl-1H-pyrazol-5-yl) | ¹H NMR (DMSO-d₆, 300 MHz): δ 0.90-1.01 (m, 4H), 2.28 (s, 3H), 2.51 (s, 1H), 3.15 (s, 3H), 3.52 (s, 3H), 3.59 (s, 1H), 3.84 (s, 3H), 4.33 (s, 2H), 4.93 (s, 2H), 7.57 (d, 1H, J = 7.8 Hz), 7.85 (d, 1H, J = 7.8 Hz), 8.10 (s, 1H). |

TABLE 1-continued

COMPOUND STRUCTURES AND $^1$H NMR DATA

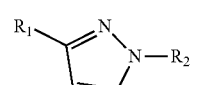

(I)

| NO. | $R_1$ | $R_2$ | $R_3$ | $R_4$ | $R_5$ | $^1$H NMR |
|---|---|---|---|---|---|---|
| 48 | cyclopropyl | —CH$_3$ | —OCH$_2$CF$_2$CHF$_2$ | —Cl | 1,4-dimethylpyrazol-5-yl | $^1$H NMR (DMSO-d$_6$, 500 MHz): δ 0.90-1.01 (m, 4H), 2.23 (s, 3H), 2.51 (s, 1H), 3.19 (s, 3H), 3.68 (s, 3H), 3.78 (s, 3H), 3.96 (t, 2H, J$_{HF}$ = 15 Hz), 5.04 (s, 2H), 5.89-6.11 (m, 1H), 7.63 (d, 1H, J = 8.0 Hz), 7.92 (d, 1H, J = 8.0 Hz), 8.11 (s, 1H). |
| 49 | cyclopropyl | —CH$_3$ | —OCH$_2$CF$_3$ | —Cl | 1,4-dimethylpyrazol-5-yl | $^1$H NMR (DMSO-d$_6$, 500 MHz): δ 0.87-1.01 (m, 4H), 2.22 (s, 3H), 2.51 (s, 1H), 3.22 (s, 3H), 3.60 (s, 3H), 3.72 (s, 3H), 4.27 (q, 2H, J$_{HF}$ = 9.0 Hz), 5.04 (s, 2H), 7.68 (d, 1H, J = 8.0 Hz), 7.92 (d, 1H, J = 8.0 Hz), 8.09 (s, 1H). |
| 50 | cyclopropyl | —CH$_3$ | —OCH$_2$CHF$_2$ | —Cl | 1,4-dimethylpyrazol-5-yl | $^1$H NMR (DMSO-d$_6$, 500 MHz): δ 0.85-0.99 (m, 4H), 2.23 (s, 3H), 2.52 (s, 1H), 3.19 (s, 3H), 3.68 (s, 3H), 3.78 (s, 3H), 3.85-3.90 (td, 2H, J = 3.5 Hz, J$_{HF}$ = 15.5 Hz), 5.04 (s, 2H), 6.11-6.33 (tt, 1H, J = 3.5 Hz, J$_{HF}$ = 55 Hz), 7.63 (d, 1H, J = 8.0 Hz), 7.92 (d, 1H, J = 8.0 Hz), 8.10 (s, 1H). |
| 51 | cyclopropyl | —CH$_3$ | —OCH$_3$ | —Cl | 1,4-dimethylpyrazol-5-yl | $^1$H NMR (DMSO-d$_6$, 500 MHz): δ 0.88-1.05 (m, 4H), 2.23 (s, 3H), 2.52 (s, 1H), 3.34 (s, 3H), 3.36 (s, 3H), 3.40 (s, 3H), 3.78 (s, 3H), 4.96 (s, 2H), 7.40 (d, 1H, J = 8.0 Hz), 8.01 (d, 1H, J = 8.0 Hz), 8.10 (s, 1H). |
| 52 | cyclopropyl | —CH$_3$ | —OCH$_2$CH$_2$CH$_2$OCH$_3$ | —Cl | 1,4-dimethylpyrazol-5-yl | $^1$H NMR (DMSO-d$_6$, 300 MHz): δ 0.90-1.01 (m, 4H), 1.09 (m, 2H), 2.37 (s, 3H), 2.51 (s, 1H), 3.17 (s, 3H), 3.44 (s, 3H), 3.56-3.69 (m, 7H), 3.84 (s, 3H), 4.91 (s, 2H), 7.52 (d, 1H, J = 7.8 Hz), 7.85 (d, 1H, J = 7.8 Hz), 8.10 (s, 1H). |
| 53 | —H | —CH$_3$ | —OCH$_2$CH$_2$CH$_2$OCH$_3$ | —Cl | 1,4-dimethylpyrazol-5-yl | $^1$H NMR (DMSO-d$_6$, 300 MHz): δ 1.08 (m, 2H), 2.31 (s, 3H), 3.19 (s, 3H), 3.44 (s, 3H), 3.54-3.68 (m, 7H), 3.84 (s, 3H), 4.91 (s, 2H), 7.53 (d, 1H, J = 7.8 Hz), 7.70 (s, 1H), 7.86 (d, 1H, J = 7.8 Hz), 8.10 (s, 1H). |

TABLE 1-continued

COMPOUND STRUCTURES AND ¹H NMR DATA (I)

$$\text{Structure with pyrazole bearing } R_1, R_2, \text{ carbonyl linked to benzene ring with } R_3, R_4, SO_2CH_3, \text{ and ester group } O-C(O)-R_5$$

| NO. | $R_1$ | $R_2$ | $R_3$ | $R_4$ | $R_5$ | ¹H NMR |
|---|---|---|---|---|---|---|
| 54 | —H | —CH$_3$ | —OCH$_2$CF$_3$ | —Cl | 1-CH$_3$, 4-CH$_3$, 5-OEt pyrazole | ¹H NMR (DMSO-d$_6$, 500 MHz): δ 1.32 (t, 3H, J = 7.0 Hz), 3.23 (s, 3H), 3.61 (s, 3H), 3.69 (s, 3H), 4.26 (q, 2H, J$_{HF}$ = 9.0 Hz), 4.32 (q, 2H, J = 7.0 Hz), 5.14 (s, 2H), 7.61 (s, 1H), 7.65 (d, 1H, J = 8.0 Hz), 7.94 (d, 1H, J = 8.0 Hz), 7.98 (s, 1H). |
| 55 | —CH$_3$ | —CH$_3$ | —OCH$_2$CF$_3$ | —Cl | 1-CH$_3$, 4-CH$_3$, 5-OEt pyrazole | ¹H NMR (DMSO-d$_6$, 500 MHz): δ 1.33 (t, 3H, J = 7.0 Hz), 2.32 (s, 3H), 3.22 (s, 3H), 3.60 (s, 3H), 3.72 (s, 3H), 4.27 (q, 2H, J$_{HF}$ = 9.0 Hz), 4.35 (q, 2H, J = 7.0 Hz), 5.14 (s, 2H), 7.68 (d, 1H, J = 8.0 Hz), 7.95 (d, 1H, J = 8.0 Hz), 7.99 (s, 1H). |
| 56 | —CH$_3$ | —CH$_3$ | HC≡C—CH$_2$O— | —Cl | 1-CH$_3$, 4-CH$_3$, 5-OEt pyrazole | ¹H NMR (DMSO-d$_6$, 500 MHz): δ 1.32 (t, 3H, J = 7.0 Hz), 2.21 (s, 3H), 3.12 (s, 3H), 3.56 (s, 3H), 3.57 (s, 1H), 3.74 (s, 3H), 4.26 (s, 2H), 4.41 (q, 2H, J = 7.0 Hz), 4.91 (s, 2H), 7.59 (d, 1H, J = 8.0 Hz), 7.91 (d, 1H, J = 8.0 Hz), 8.02 (s, 1H). |
| 57 | —H | —CH$_3$ | —OCH$_2$CHF$_2$ | —Cl | 1-CH$_3$, 4-CH$_3$, 5-OEt pyrazole | ¹H NMR (DMSO-d$_6$, 500 MHz): δ 1.38 (t, 3H, J = 7.0 Hz), 3.19 (s, 3H), 3.68 (s, 3H), 3.78 (s, 3H), 3.85-3.90 (td, 2H, J = 3.5 Hz, J$_{HF}$ = 15.5 Hz), 4.45 (q, 2H, J = 7.0 Hz), 5.04 (s, 2H), 6.11-6.33 (tt, 1H, J = 3.5 Hz, J$_{HF}$ = 55 Hz), 7.63 (d, 1H, J = 8.0 Hz), 7.92 (d, 1H, J = 8.0 Hz), 7.99 (s, 1H), 8.02 (s, 1H), |
| 58 | —H | —CH$_3$ | HC≡C—CH$_2$O— | —Cl | 1-CH$_3$, 4-CH$_3$, 5-OEt pyrazole | ¹H NMR (DMSO-d$_6$, 500 MHz): δ 1.32 (t, 3H, J = 7.0 Hz), 3.12 (s, 3H), 3.56 (s, 3H), 3.57 (s, 1H), 3.74 (s, 3H), 4.26 (s, 2H), 4.41 (q, 2H, J = 7.0 Hz), 4.91 (s, 2H), 7.59 (d, 1H, J = 8.0 Hz), 7.91 (d, 1H, J = 8.0 Hz), 7.98 (s, 1H), 8.02 (s, 1H). |
| 59 | —H | —CH$_3$ | —OCH$_2$CH$_2$OCH$_2$CH$_3$ | —Cl | 1-CH$_3$, 4-CH$_3$, 5-OEt pyrazole | ¹H NMR (DMSO-d$_6$, 500 MHz): δ 1.10 (t, 3H, J = 7.0 Hz), 1.32 (t, 3H, J = 7.0 Hz), 3.23 (s, 3H), 3.42 (q, 2H, J = 7.0 Hz), 3.51-3.57 (m, 4H), 3.67 (s, 3H), 3.78 (s, 3H), 4.32 (q, 2H, J = 7.0 Hz), 5.14 (s, 2H), 7.65 (d, 1H, J = 8.0 Hz), 7.89 (d, 1H, J = 8.0 Hz), 7.97 |

TABLE 1-continued

COMPOUND STRUCTURES AND $^1$H NMR DATA

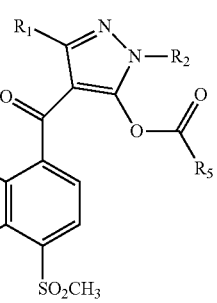

(I)

| NO. | $R_1$ | $R_2$ | $R_3$ | $R_4$ | $R_5$ | $^1$H NMR |
|---|---|---|---|---|---|---|
| | | | | | | (s, 1H), 8.01 (s, 1H). |
| 60 | cyclopropyl | —CH$_3$ | HC≡C—CH$_2$O— | —Cl | 1-methylpyrazol-4-yl (CH$_3$) | $^1$H NMR (DMSO-d$_6$, 300 MHz): δ 0.90-1.01 (m, 4H), 2.51 (s, 1H), 3.15 (s, 3H), 3.52 (s, 3H), 3.59 (s, 1H), 3.84 (s, 3H), 4.33 (s, 2H), 4.93 (s, 2H), 7.57 (d, 1H, J = 7.8 Hz), 7.69 (s, 1H), 7.85 (d, 1H, J = 7.8 Hz), 8.10 (s, 1H). |
| 61 | —H | —CH$_3$ | HC≡C—CH$_2$O— | —Cl | 1-methylpyrazol-4-yl (CH$_3$) | $^1$H NMR (DMSO-d$_6$, 500 MHz): δ 3.10 (s, 3H), 3.55 (s, 3H), 3.61 (s, 1H), 3.77 (s, 3H), 4.35 (s, 2H), 4.92 (s, 2H), 7.58 (d, 1H, J = 8.0 Hz), 7.81 (d, 1H, J = 8.0 Hz), 7.89 (s, 1H), 7.98 (s, 1H), 8.02 (s, 1H). |
| 62 | —H | —CH$_3$ | —OCH$_2$CH$_2$CH$_2$OCH$_3$ | —Cl | 1-methylpyrazol-4-yl (CH$_3$) | $^1$H NMR (DMSO-d$_6$, 300 MHz): δ 1.09 (m, 2H), 3.17 (s, 3H), 3.44 (s, 3H), 3.56-3.69 (m, 7H), 3.84 (s, 3H), 4.91 (s, 2H), 7.52 (d, 1H, J = 7.8 Hz), 7.70 (s, 1H), 7.85 (d, 1H, J = 7.8 Hz), 7.96 (s, 1H), 8.10 (s, 1H). |
| 63 | —CH$_3$ | —CH$_3$ | —OCH$_2$CF$_3$ | —Cl | 1-methylpyrazol-4-yl (CH$_3$) | $^1$H NMR (DMSO-d$_6$, 500 MHz): δ 2.21 (s, 3H), 3.23 (s, 3H), 3.61 (s, 3H), 3.69 (s, 3H), 4.26 (q, 2H, J$_{HF}$ = 9.0 Hz), 5.14 (s, 2H), 7.65 (s, 1H), 7.65 (d, 1H, J = 8.0 Hz), 7.94 (d, 1H, J = 8.0 Hz), 8.01 (s, 1H). |
| 64 | —CH$_3$ | —CH$_3$ | —OCH$_2$CHF$_2$ | —Cl | 1-methylpyrazol-4-yl (CH$_3$) | $^1$H NMR (DMSO-d$_6$, 500 MHz): δ 2.33 (s, 3H), 3.19 (s, 3H), 3.68 (s, 3H), 3.78 (s, 3H), 3.85-3.90 (td, 2H, J = 3.5 Hz, J$_{HF}$ = 15.5 Hz), 5.04 (s, 2H), 6.11-6.33 (tt, 1H, J = 3.5 Hz, J$_{HF}$ = 55 Hz), 7.63 (d, 1H, J = 8.0 Hz), 7.92 (d, 1H, J = 8.0 Hz), 7.99 (s, 1H), 8.10 (s, 1H). |
| 65 | —CH$_3$ | —CH$_3$ | —OCH$_2$CF$_2$CHF$_2$ | —Cl | 1-methylpyrazol-4-yl (CH$_3$) | $^1$H NMR (DMSO-d$_6$, 500 MHz): δ 2.36 (s, 3H), 3.19 (s, 3H), 3.68 (s, 3H), 3.78 (s, 3H), 3.96 (t, 2H, J$_{HF}$ = 15 Hz), 5.04 (s, 2H), 5.89-6.11 (m, 1H), 7.63 (d, 1H, J = 8.0 Hz), 7.92 (d, 1H, J = 8.0 Hz), 8.01 (s, 1H), 8.10 (s, 1H). |

TABLE 1-continued

COMPOUND STRUCTURES AND $^1$H NMR DATA

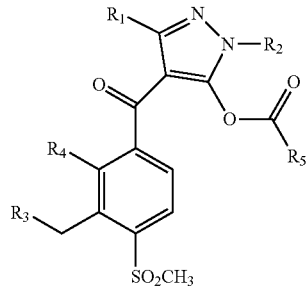

(I)

| NO. | $R_1$ | $R_2$ | $R_3$ | $R_4$ | $R_5$ | $^1$H NMR |
|---|---|---|---|---|---|---|
| 66 | —CH$_3$ | —CH$_3$ | —OCH$_2$CH$_2$CH$_2$OCH$_3$ | —Cl | | $^1$H NMR (DMSO-d$_6$, 300 MHz): δ 1.09 (m, 2H), 2.41 (s, 3H), 3.17 (s, 3H), 3.44 (s, 3H), 3.56-3.69 (m, 7H), 3.84 (s, 3H), 4.91 (s, 2H), 7.52 (d, 1H, J = 7.8 Hz), 7.70 (s, 1H), 7.85 (d, 1H, J = 7.8 Hz), 8.10 (s, 1H). |
| 67 | —H | —CH$_3$ | —OCH$_2$CF$_3$ | —Cl | | $^1$H NMR (DMSO-d$_6$, 500 MHz): δ 3.18 (s, 3H), 3.55 (s, 3H), 3.69 (s, 3H), 4.28 (q, 2H, $J_{HF}$ = 9.0 Hz), 5.14 (s, 2H), 7.61 (s, 1H), 7.65 (d, 1H, J = 8.0 Hz), 7.94 (d, 1H, J = 8.0 Hz), 7.98 (s, 1H), 8.09 (s, 1H). |
| 68 | —H | —CH$_3$ | —OCH$_2$CH$_2$OCH$_2$CH$_3$ | —Cl | | $^1$H NMR (DMSO-d$_6$, 500 MHz): δ 1.11 (t, 3H, J = 7.0 Hz), 3.13 (s, 3H), 3.48 (q, 2H, J = 7.0 Hz), 3.51-3.57 (m, 4H), 3.67 (s, 3H), 3.78 (s, 3H), 5.14 (s, 2H), 7.65 (d, 1H, J = 8.0 Hz), 7.89 (d, 1H, J = 8.0 Hz), 7.97 (s, 1H), 8.01 (s, 1H), 8.10 (s, 1H). |
| 69 | —CH$_3$ | —CH$_3$ | HC≡C—CH$_2$O— | —Cl | | $^1$H NMR (DMSO-d$_6$, 500 MHz): δ 2.27 (s, 3H), 3.12 (s, 3H), 3.56 (s, 3H), 3.57 (s, 1H), 3.74 (s, 3H), 4.32 (s, 2H), 4.91 (s, 2H), 7.54 (d, 1H, J = 8.0 Hz), 7.84 (d, 1H, J = 8.0 Hz), 7.90 (s, 1H), 7.99 (s, 1H). |
| 70 | ▷ | —CH$_3$ | —OCH$_2$CH$_3$ | —Cl | | $^1$H NMR (DMSO-d$_6$, 500 MHz): δ 0.92-1.05 (m, 4H), 1.14 (t, 3H, J = 7.0 Hz), 2.51 (s, 1H), 3.36 (s, 3H), 3.41 (s, 3H), 3.55 (q, 2H, J = 7.0 Hz), 3.77 (s, 3H), 4.98 (s, 2H), 7.45 (d, 1H, J = 8.0 Hz), 7.79 (s, 1H), 7.98 (d, 1H, J = 8.0 Hz), 8.06 (s, 1H). |
| 71 | ▷ | —CH$_3$ | —OCH$_2$CF$_2$CHF$_2$ | —Cl | | $^1$H NMR (DMSO-d$_6$, 500 MHz): δ 0.89-1.01 (m, 4H), 2.52 (s, 1H), 3.19 (s, 3H), 3.68 (s, 3H), 3.78 (s, 3H), 3.96 (t, 2H, $J_{HF}$ = 15 Hz), 5.04 (s, 2H), 5.89-6.11 (m, 1H), 7.63 (d, 1H, J = 8.0 Hz), 7.92 (d, 1H, J = 8.0 Hz), 8.01 (s, 1H), 8.10 (s, 1H). |

TABLE 1-continued

COMPOUND STRUCTURES AND ¹H NMR DATA

(I)

| NO. | R₁ | R₂ | R₃ | R₄ | R₅ | ¹H NMR |
|-----|----|----|----|----|----|--------|
| 72 | cyclopropyl | —CH₃ | —OCH₃ | —Cl | 1,4-dimethylpyrazolyl | ¹H NMR (DMSO-d₆, 500 MHz): δ 0.91-1.03 (m, 4H), 2.51 (s, 1H), 3.34 (s, 3H), 3.36 (s, 3H), 3.40 (s, 3H), 3.78 (s, 3H), 4.96 (s, 2H), 7.40 (d, 1H, J = 8.0 Hz), 7.74 (s, 1H), 8.01 (d, 1H, J = 8.0 Hz), 8.10 (s, 1H). |
| 73 | —CH₃ | —CH₃ | —OCH₂CH₃ | —Cl | 1,4-dimethylpyrazolyl | ¹H NMR (DMSO-d₆, 500 MHz): δ 1.14 (t, 3H, J = 7.0 Hz), 2.21 (s, 3H), 3.36 (s, 3H), 3.41 (s, 3H), 3.55 (q, 2H, J = 7.0 Hz), 3.77 (s, 3H), 4.98 (s, 2H), 7.45 (d, 1H, J = 8.0 Hz), 7.77 (s, 1H), 7.98 (d, 1H, J = 8.0 Hz), 8.08 (s, 1H). |
| 74 | cyclopropyl | —CH₃ | —OCH₂CH₂OCH₂CH₃ | —Cl | 1,4-dimethylpyrazolyl | ¹H NMR (DMSO-d₆, 500 MHz): δ 0.92-1.00 (m, 4H), 1.11 (t, 3H, J = 7.0 Hz), 2.51 (s, 1H), 3.13 (s, 3H), 3.48 (q, 2H, J = 7.0 Hz), 3.51-3.57 (m, 4H), 3.67 (s, 3H), 3.78 (s, 3H), 5.14 (s, 2H), 7.65 (d, 1H, J = 8.0 Hz), 7.89 (d, 1H, J = 8.0 Hz), 7.97 (s, 1H), 8.10 (s, 1H). |
| 75 | cyclopropyl | —CH₃ | —OCH₂CH₂CH₂CH₃ | —Cl | 1,4-dimethylpyrazolyl | ¹H NMR (DMSO-d₆, 500 MHz): δ 0.83-1.05 (m, 7H), 1.45-1.51 (m, 4H), 2.29 (s, 3H), 3.37 (s, 3H), 3.45 (s, 3H), 3.56 (t, 2H, J = 7.0 Hz), 3.78 (s, 3H), 4.99 (s, 2H), 7.58 (d, 1H, J = 8.0 Hz), 7.96 (d, 1H, J = 8.0 Hz), 8.09 (s, 1H). |
| 76 | —CH₃ | —CH₃ | HC≡C—CH₂O— | —CH₃ | 1,3,4-trimethylpyrazolyl | ¹H NMR (DMSO-d₆, 500 MHz): δ 2.09 (s, 3H), 2.31 (s, 3H), 2.42 (s, 3H), 3.12 (s, 3H), 3.56 (s, 3H), 3.57 (s, 1H), 3.74 (s, 3H), 4.32 (s, 2H), 4.91 (s, 2H), 7.54 (d, 1H, J = 8.0 Hz), 7.84 (d, 1H, J = 8.0 Hz), 7.98 (s, 1H). |
| 77 | —H | —CH₃ | 1-methylpyrazolyl | —CH₃ | 1,3,4-trimethylpyrazolyl | ¹H NMR (DMSO-d₆, 500 MHz): δ 2.22 (s, 3H), 2.37 (s, 3H), 3.23 (s, 3H), 3.54 (s, 3H), 3.72 (s, 3H), 5.78 (s, 2H), 6.23 (s, 1H), 7.22 (s, 1H), 7.35 (s, 1H), 7.55 (s, 1H), 7.61 (d, 1H, J = 8.0 Hz), 7.93 (d, 1H, J = 8.0 Hz), 8.07 (s, 1H). |

TABLE 1-continued

COMPOUND STRUCTURES AND ¹H NMR DATA

(I)

| NO. | $R_1$ | $R_2$ | $R_3$ | $R_4$ | $R_5$ | ¹H NMR |
|---|---|---|---|---|---|---|
| 78 | 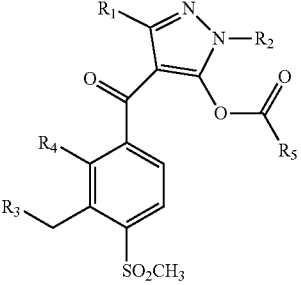 | —CH₃ | —OCH₂CF₃ | —CH₃ | 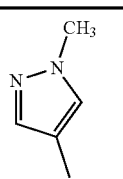 | ¹H NMR (DMSO-d₆, 500 MHz): δ 0.83-1.05 (m, 4H), 2.34 (s, 3H), 2.51 (s, 1H), 3.36 (s, 3H), 3.41 (s, 3H), 4.35 (q, 2H, J = 7.0 Hz), 3.77 (s, 3H), 4.98 (s, 2H), 7.45 (d, 1H, J = 8.0 Hz), 7.79 (s, 1H), 7.98 (d, 1H, J = 8.0 Hz), 8.06 (s, 1H). |
| 79 | —CH₃ | —CH₃ | 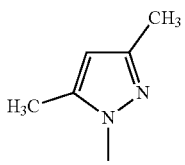 | —CH₃ | 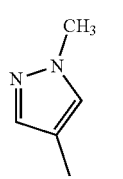 | ¹H NMR (DMSO-d₆, 500 MHz): δ 2.07 (s, 3H), 2.22(s, 3H), 2.29 (s, 3H), 2,44 (s, 3H), 3.09 (s, 3H), 3.58 (s, 3H), 3.74 (s, 3H), 5.72 (s, 2H), 6.24 (s, 1H), 7.56 (d, 1H, J = 8.0 Hz), 7.79 (s, 1H), 7.91 (d, 1H, J = 8.0 Hz), 8.02 (s, 1H). |
| 80 | —H | —CH₃ | —OCH₂CH₃ | —CH₃ | 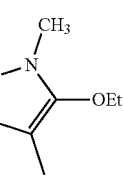 | ¹H NMR (DMSO-d₆, 500 MHz): δ 1.10 (t, 3H, J = 7.0 Hz), 1.32 (t, 3H, J = 7.0 Hz), 2.30 (s, 3H), 3.23 (s, 3H), 3.58 (q, 2H, J = 7.0 Hz), 3.61 (s, 3H), 3.72 (s, 3H), 4.32 (q, 2H, J = 7.0 Hz), 5.14 (s, 2H), 7.61 (s, 1H), 7.65 (d, 1H, J = 8.0 Hz), 7.94 (d, 1H, J = 8.0 Hz), 7.98 (s, 1H). |
| 81 | 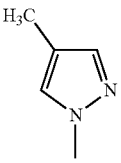 | —CH₃ | 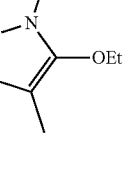 | —CH₃ |  | ¹H NMR (DMSO-d₆, 300 MHz): δ 0.86-1.21 (m, 4H), 1.32 (t, 3H, J = 7.2 Hz), 2.15 (s, 3H), 2.26 (s, 3H), 2.36 (s, 3H), 2.41 (s, 1H), 3.19 (s, 3H), 3.69 (s, 3H), 4.38 (q, 2H, J = 7.2 Hz), 5.86 (s, 2H), 6.42 (s, 1H), 7.64 (d, 1H, J = 7.8 Hz), 7.78 (s, 1H), 7.89 (d, 1H, J = 7.8 Hz), 7.98 (s, 1H). |
| 82 | —CH₃ | —CH₂CH₃ | 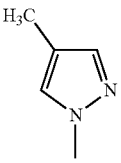 | —CH₃ | 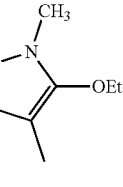 | ¹H NMR (DMSO-d₆, 500 MHz): δ 1.19 (t, 3H, J = 7.0 Hz), 1.35 (t, 3H, J = 7.0 Hz), 2.28 (s, 3H), 2.36 (s, 3H), 3.23 (s, 3H), 3.68 (q, 2H, J = 7.0 Hz), 3.76 (s, 3H), 4.37 (q, 2H, J = 7.0 Hz), 5.69 (s, 2H), 7.29 (s, 1H), 7.41 (s, 1H), 7.60 (d, 1H, J = 8.0 Hz), 7.92 (d, 1H, J = 8.0 Hz), 8.00 (s, 1H). |
| 83 | —H | —CH₂CH₃ | —OCH₂CH₂CH₂OCH₃ | —CH₃ | 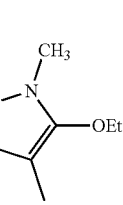 | ¹H NMR (DMSO-d₆, 300 MHz): δ 1.09 (m, 2H), 1.18 (t, 3H, J = 7.2 Hz), 2.26 (s, 3H), 2.35 (s, 3H), 3.17 (s, 3H), 3.56-3.69 (m, 7H), 3.74 (q, 2H, J = 7.2 Hz), 3.84 (s, 3H), 4.91 (s, 2H), 7.52 (d, 1H, J = 7.8 Hz), 7.70 (s, 1H), 7.85 (d, 1H, J = 7.8 Hz), 7.96 (s, 1H), 8.10 (s, 1H). |

TABLE 1-continued

COMPOUND STRUCTURES AND ¹H NMR DATA

(I)

| NO. | R₁ | R₂ | R₃ | R₄ | R₅ | ¹H NMR |
|---|---|---|---|---|---|---|
| 84 | cyclopropyl | —CH₂CH₃ | 4-chloro-1-methylpyrazol-3-yl | —CH₃ | 1,3-dimethyl-4-methylpyrazol-5-yl | ¹H NMR (DMSO-d₆, 500 MHz): δ 0.83-1.11 (m, 4H), 1.20 (t, 3H, J = 7.0 Hz), 2.22 (s, 3H), 2.37 (s, 3H), 2.49 (s, 1H), 3.23 (s, 3H), 3.70-3.76 (m, 5H), 5.78 (s, 2H), 7.22 (s, 1H), 7.35 (s, 1H), 7.61 (d, 1H, J = 8.0 Hz), 7.93 (d, 1H, J = 8.0 Hz), 8.07 (s, 1H). |
| 85 | —CH₃ | —CH₂CH₃ | —OCH₂CF₂CHF₂ | —CH₃ | 1,4-dimethylpyrazol-5-yl | ¹H NMR (DMSO-d₆, 500 MHz): δ 1.19 (t, 3H, J = 7.0 Hz), 2.24 (s, 3H), 2.36 (s, 3H), 3.19 (s, 3H), 3.65 (s, 3H), 3.78 (q, 2H, J = 7.0 Hz), 3.96 (t, 2H, J_HF = 15 Hz), 5.04 (s, 2H), 5.89-6.11 (m, 1H), 7.63 (d, 1H, J = 8.0 Hz), 7.92 (d, 1H, J = 8.0 Hz), 8.01 (s, 1H), 8.10 (s, 1H). |
| 86 | cyclopropyl | —CH₂CH₃ | —OCH₂CH₂OCH₂CH₃ | —CH₃ | 1-methyl-5-ethoxy-4-methylpyrazol-3-yl | ¹H NMR (DMSO-d₆, 500 MHz): δ 0.83-1.11 (m, 4H), 1.10-1.18 (m, 6H), 1.32 (t, 3H, J = 7.0 Hz), 2.31 (s, 3H), 2.44 (s, 1H), 3.23 (s, 3H), 3.42 (q, 2H, J = 7.0 Hz), 3.51-3.57 (m, 4H), 3.71 (q, 2H, J = 7.0 Hz), 3.78 (s, 3H), 4.32 (q, 2H, J = 7.0 Hz), 5.04 (s, 2H), 7.65 (d, 1H, J = 8.0 Hz), 7.89 (d, 1H, J = 8.0 Hz), 7.99 (s, 1H). |
| 87 | —H | —CH₂CH₃ | 4-methyl-1-methylpyrazol-3-yl | —CH₃ | 1,4-dimethylpyrazol-5-yl | ¹H NMR (DMSO-d₆, 500 MHz): δ 1.16 (t, 3H, J = 7.0 Hz), 2.01 (s, 3H), 2.27 (s, 3H), 2.49 (s, 1H), 3.23 (s, 3H), 3.68 (q, 2H, J = 7.0 Hz), 3.76 (s, 3H), 5.69 (s, 2H), 7.29 (s, 1H), 7.41 (s, 1H), 7.60 (d, 1H, J = 8.0 Hz), 7.68 (s, 1H), 7.97 (d, 1H, J = 8.0 Hz), 8.08 (s, 1H). |
| 88 | —H | —CH₂CH₃ | H₃C—CH=CH—CH₂O— | —Cl | 1,4-dimethylpyrazol-5-yl | ¹H NMR (DMSO-d₆, 500 MHz): δ 1.18 (t, 3H, J = 7.0 Hz), 1.95 (s, 3H), 3.27 (s, 3H), 3.72-3.79 (m, 5H), 3.92 (s, 2H), 4.96 (s, 2H), 5.28 (s, 1H), 5.31 (s, 1H), 7.49 (d, 1H, J = 8.0 Hz), 7.68 (s, 1H), 7.77 (s, 1H), 7.89 (d, 1H, J = 8.0 Hz), 8.08 (s, 1H). |
| 89 | —CH₃ | —CH₂CH₃ | 1-methylpyrazol-5-yl | —Cl | 1,3-dimethyl-4-methylpyrazol-5-yl | ¹H NMR (DMSO-d₆, 500 MHz): δ 1.20 (t, 3H, J = 7.0 Hz), 2.08 (s, 3H), 2.34 (s, 3H), 3.36 (s, 3H), 3.70-3.75 (m, 5H), 5.75 (s, 2H), 6.25 (s, 1H), 7.25 (s, 1H), 7.56 (s, 1H), 7.59 (d, 1H, J = 8.0 Hz), 7.91 (d, 1H, J = 8.0 Hz), 8.02 (s, 1H). |

TABLE 1-continued

COMPOUND STRUCTURES AND $^1$H NMR DATA

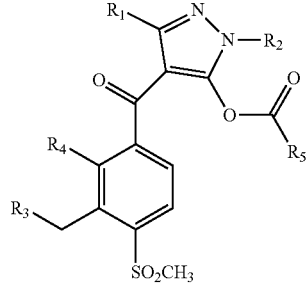

(I)

| NO. | R$_1$ | R$_2$ | R$_3$ | R$_4$ | R$_5$ | $^1$H NMR |
|---|---|---|---|---|---|---|
| 90 | cyclopropyl | —CH$_2$CH$_3$ | —OCH$_2$CHF$_2$ | —Cl | 1,3-dimethylpyrazol-4-yl | $^1$H NMR (DMSO-d$_6$, 500 MHz): δ 0.85-0.99 (m, 4H), 1.18 (t, 3H, J = 7.0 Hz), 2.23 (s, 3H), 2.52 (s, 1H), 3.19 (s, 3H), 3.69 (s, 3H), 3.74 (q, 2H, J = 7.0 Hz), 3.85-3.90 (td, 2H, J = 3.5 Hz, J$_{HF}$ = 15.5 Hz), 5.04 (s, 2H), 6.11-6.33 (tt, 1H, J = 3.5 Hz, J$_{HF}$ = 55 Hz), 7.63 (d, 1H, J = 8.0 Hz), 7.92 (d, 1H, J = 8.0 Hz), 8.10 (s, 1H). |
| 91 | cyclopropyl | —CH$_2$CH$_3$ | 4-methylpyrazol-1-yl | —Cl | 1-methyl-4-methylpyrazol-3-yl | $^1$H NMR (DMSO-d$_6$, 500 MHz): δ 0.92-1.19 (m, 4H), 1.19 (t, 3H, J = 7.0 Hz), 1.99 (s, 3H), 2.45 (s, 1H), 3.28 (s, 3H), 3.67 (s, 3H), 3.75 (q, 2H, J = 7.0 Hz), 5.76 (s, 2H), 7.26 (s, 1H), 7.44 (s, 1H), 7.58 (d, 1H, J = 8.0 Hz), 7.71 (s, 1H), 7.92 (d, 1H, J = 8.0 Hz), 8.06 (s, 1H). |
| 92 | —CH$_3$ | —CH$_2$CH$_3$ | —OCH$_3$ | —Cl | 1-methyl-5-ethoxy-4-methylpyrazol-3-yl | $^1$H NMR (DMSO-d$_6$, 500 MHz): δ 1.20 (t, 3H, J = 7.0 Hz), 1.30 (t, 3H, J = 7.0 Hz), 2.23 (s, 3H), 3.29 (s, 3H), 3.61 (s, 3H), 3.69 (s, 3H), 3.76 (q, 2H, J = 7.0 Hz), 4.24 (q, 2H, J = 7.0 Hz), 4.98 (s, 2H), 7.65 (d, 1H, J = 8.0 Hz), 7.94 (d, 1H, J = 8.0 Hz), 7.98 (s, 1H). |
| 93 | —H | —CH$_2$CH$_3$ | 3,5-dimethyl-1H-pyrazol-1-yl | —Cl | 1-methyl-5-ethoxy-4-methylpyrazol-3-yl | $^1$H NMR (DMSO-d$_6$, 500 MHz): δ 1.18 (t, 3H, J = 7.0 Hz), 1.30 (t, 3H, J = 7.0 Hz), 2.24 (s, 3H), 2.38 (s, 3H), 3.29 (s, 3H), 3.66 (s, 3H), 3.74 (q, 2H, J = 7.0 Hz), 4.30 (q, 2H, J = 7.0 Hz), 5.76 (s, 2H), 6.24 (s, 1H), 7.60 (s, 1H), 7.78 (d, 1H, J = 8.0 Hz), 7.96 (d, 1H, J = 8.0 Hz), 8.01 (s, 1H). |
| 94 | —CH$_2$CH$_3$ | —CH$_2$CH$_3$ | —OCH$_2$CHF$_2$ | —Cl | 1,3-dimethylpyrazol-4-yl | $^1$H NMR (DMSO-d$_6$, 500 MHz): δ 1.05 (t, 3H, J = 7.0 Hz), 1.18 (t, 3H, J = 7.0 Hz), 2.23 (s, 3H), 3.19 (s, 3H), 3.48 (q, 2H, J = 7.0 Hz), 3.69 (s, 3H), 3.74 (q, 2H, J = 7.0 Hz), 3.85-3.90 (td, 2H, J = 3.5 Hz, J$_{HF}$ = 15.5 Hz), 5.04 (s, 2H), 6.11-6.33 (tt, 1H, J = 3.5 Hz, J$_{HF}$ = 55 Hz), 7.63 (d, 1H, J = 8.0 Hz), 7.92 (d, 1H, J = 8.0 Hz), 8.10 (s, 1H). |

TABLE 1-continued

COMPOUND STRUCTURES AND $^1$H NMR DATA

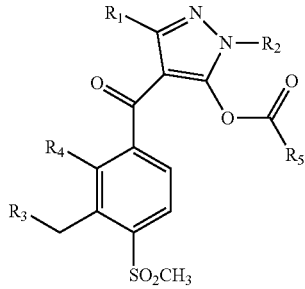

(I)

| NO. | R$_1$ | R$_2$ | R$_3$ | R$_4$ | R$_5$ | $^1$H NMR |
|---|---|---|---|---|---|---|
| 95 | —CH$_2$CH$_3$ | —CH$_2$CH$_3$ | 3,5-dimethyl-1-methyl-1H-pyrazol-4-yl-methyl | —Cl | 1,3-dimethyl-1H-pyrazol-4-yl | $^1$H NMR (DMSO-d$_6$, 500 MHz): δ 1.02 (t, 3H, J = 7.0 Hz), 1.19 (t, 3H, J = 7.0 Hz), 2.07 (s, 3H), 2.22 (s, 3H), 3.18 (s, 3H), 3.30 (s, 3H), 3.49 (q, 2H, J = 7.0 Hz), 3.62 (s, 3H), 3.78 (q, 2H, J = 7.0 Hz), 4.99 (s, 2H), 7.45 (s, 1H). 7.63 (d, 1H, J = 8.0 Hz), 7.92 (d, 1H, J = 8.0 Hz), 8.10 (s, 1H). |
| 96 | cyclopropyl | —CH(CH$_3$)$_2$ | —OCH$_2$CH$_3$ | —Cl | 1,3-dimethyl-1H-pyrazol-4-yl | $^1$H NMR (DMSO-d$_6$, 500 MHz): δ 0.87-1.05 (m, 4H), 1.17-1.28 (m, 9H), 2.28 (q, 2H, J = 7.0 Hz), 2.52 (s, 1H), 3.35 (s, 3H), 3.42 (s, 3H), 3.54-3.64 (m, 1H), 3.72 (s, 3H), 5.01 (s, 2H), 7.45 (d, 1H, J = 8.0 Hz), 7.99 (d, 1H, J = 8.0 Hz), 8.08 (s, 1H). |
| 97 | —H | —CH(CH$_3$)$_2$ | 4-methyl-1-methyl-1H-pyrazol-3-yl | —Cl | 1,3-dimethyl-1H-pyrazol-4-yl | $^1$H NMR (DMSO-d$_6$, 500 MHz): δ 1.17 (d, 6H, J = 7.0 Hz), 2.00 (s, 3H), 3.08 (s, 3H), 3.54-3.68 (m, 4H), 3.74 (s, 3H), 5.76 (s, 2H), 7.26 (s, 1H), 7.38 (s, 1H), 7.52 (s, 1H), 7.58 (d, 1H, J = 8.0 Hz), 7.92 (d, 1H, J = 8.0 Hz), 8.04 (s, 1H). |
| 98 | —CH$_3$ | —CH(CH$_3$)$_2$ | —OCH$_2$CF$_3$ | —Cl | 1,3-dimethyl-1H-pyrazol-4-yl | $^1$H NMR (DMSO-d$_6$, 500 MHz): δ 1.21 (d, 6H, J = 7.0 Hz), 2.16 (s, 3H), 3.34 (s, 3H), 3.40 (s, 3H), 3.54-3.62 (m, 1H), 3.78 (s, 3H), 4.22 (q, 2H, J$_{HF}$ = 9.0 Hz), 4.96 (s, 2H), 7.42 (d, 1H, J = 8.0 Hz), 8.02 (d, 1H, J = 8.0 Hz), 8.11 (s, 1H). |
| 99 | —CH$_2$CH$_3$ | —CH(CH$_3$)$_2$ | 1-methyl-1H-pyrazol-5-yl | —Cl | 1,3-dimethyl-1H-pyrazol-4-yl | $^1$H NMR (DMSO-d$_6$, 500 MHz): δ 1.09 (t, 3H, J = 7.0 Hz), 1.28 (d, 6H, J = 7.0 Hz), 2.22 (s, 3H), 2.49 (q, 2H, J = 7.0 Hz), 3.30 (s, 3H), 3.50-3.68 (m, 4H), 4.99 (s, 2H), 6.24 (s, 1H). 7.45 (s, 1H). 7.63 (d, 1H, J = 8.0 Hz), 7.92 (d, 1H, J = 8.0 Hz), 8.02 (s, 1H), 8.10 (s, 1H). |
| 100 | —H | —CH(CH$_3$)$_2$ | HC≡C—CH$_2$O— | —Cl | 1,3-dimethyl-1H-pyrazol-4-yl | $^1$H NMR (DMSO-d$_6$, 500 MHz): δ 1.25 (d, 6H, J = 7.0 Hz), 3.12 (s, 3H), 3.50-3.68 (m, 5H), 3.74 (s, 3H), 4.32 (s, 2H), 4.91 (s, 2H), 7.54 (d, 1H, J = 8.0 Hz), 7.71 (s, 1H), 7.84 (d, 1H, J = 8.0 Hz), 7.98 (s, 1H). |

TABLE 1-continued

COMPOUND STRUCTURES AND ¹H NMR DATA

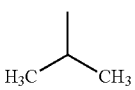

(I)

| NO. | R₁ | R₂ | R₃ | R₄ | R₅ | ¹H NMR |
|---|---|---|---|---|---|---|
| 101 | —CH₃ | 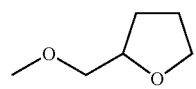 | 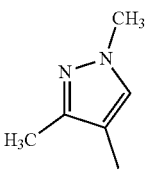 | —Cl | 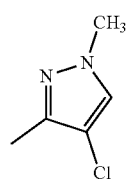 | ¹H NMR (DMSO-d₆, 500 MHz): δ 1.21 (d, 6H, J = 7.0 Hz), 1.70-1.90 (m, 4H), 2.16 (s, 3H), 3.34 (s, 3H), 3.40 (s, 3H), 3.54-3.62 (m, 1H), 3.78 (s, 3H), 3.82-3.94 (m, 2H), 4.26 (s, 2H), 4.68-4.76 (m, 1H), 4.96 (s, 2H), 7.42 (d, 1H, J = 8.0 Hz), 8.02 (d, 1H, J = 8.0 Hz), 8.10 (s, 1H). |
| 102 | —H | —CH₃ | —OCH₂CHF₂ | —Cl | 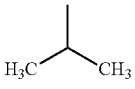 | ¹H NMR (DMSO-d₆, 500 MHz): δ 3.09 (s, 3H), 3.68 (s, 3H), 3.78 (s, 3H), 3.85-3.90 (td, 2H, J = 3.5 Hz, J_{HF} = 15.5 Hz), 5.04 (s, 2H), 6.11-6.33 (tt, 1H, J = 3.5 Hz, J_{HF} = 55 Hz), 7.40 (s, 1H), 7.63 (d, 1H, J = 8.0 Hz), 7.92 (d, 1H, J = 8.0 Hz), 8.00 (s, 1H). |
| 103 | —CH₃ | 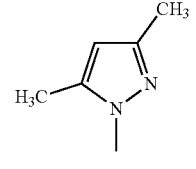 | 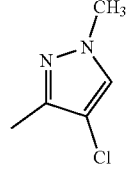 | —Cl | 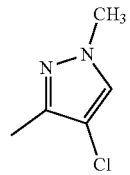 | ¹H NMR (DMSO-d₆, 500 MHz): δ 1.21 (d, 6H, J = 7.0 Hz), 2.07 (s, 3H), 2.29 (s, 3H), 2,44 (s, 3H), 3.09 (s, 3H), 3.42 (s, 3H), 3.59-3.68(m, 1H), 5.72 (s, 2H), 6.24 (s, 1H), 7.56 (d, 1H, J = 8.0 Hz), 7.91 (d, 1H, J = 8.0 Hz), 8.05 (s, 1H). |
| 104 | —CH₂CH₃ | —CH₂CH₃ | —OCH₂CH₃ | —Cl | 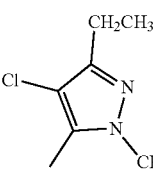 | ¹H NMR (DMSO-d₆, 500 MHz): δ 1.10-1.25 (m, 6H), 1.37 (t, 3H, J = 7.0 Hz), 2.29-2.41 (m, 4H), 3.12 (q, 2H, J = 7.0 Hz), 3.32 (s, 3H), 3.68 (s, 3H), 4.89 (s, 2H), 7.62 (d, 1H, J = 8.0 Hz), 7.99 (d, 1H, J = 8.0 Hz), 8.11 (s, 1H),. |
| 105 | —H | —CH₃ | —OCH₂CF₃ | —Cl | 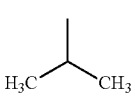 | ¹H NMR (DMSO-d₆, 500 MHz): δ 1.25 (t, 3H, J = 7.0 Hz), 2.35 (q, 2H, J = 7.0 Hz), 3.34 (s, 3H), 3.48 (s, 3H), 3.78 (s, 3H), 4.22 (q, 2H, J_{HF} = 9.0 Hz), 4.86 (s, 2H), 7.42 (d, 1H, J = 8.0 Hz), 7.71 (s, 1H), 8.02 (d, 1H, J = 8.0 Hz). |
| 106 | —CH₃ | 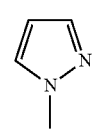 | 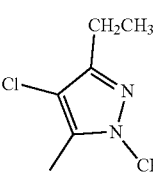 | —Cl | 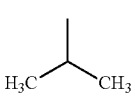 | ¹H NMR (DMSO-d₆, 500 MHz): δ 1.20 (t, 3H, J = 7.0 Hz), 1.48 (d, 6H, J = 7.0 Hz), 2.29 (q, 2H, J = 7.0 Hz), 3.34 (s, 3H), 3.48 (s, 3H), 3.53-3.62 (m, 1H), 3.78 (s, 3H), 4.86 (s, 2H), 6.26 (s, 1H), 7.25 (s, 1H), 7.59 (d, 1H, J = 8.0 Hz), 7.91 (d, 1H, J = 8.0 Hz), 8.02 (s, 1H). |

TABLE 1-continued

COMPOUND STRUCTURES AND ¹H NMR DATA

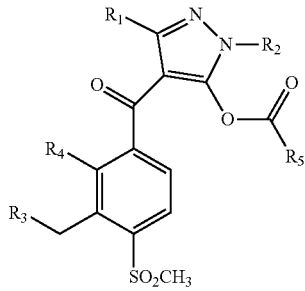

(I)

| NO. | R₁ | R₂ | R₃ | R₄ | R₅ | ¹H NMR |
|---|---|---|---|---|---|---|
| 107 | —CH₂CH₃ | —CH₂CH₃ | HC≡C—CH₂O— | —Cl | 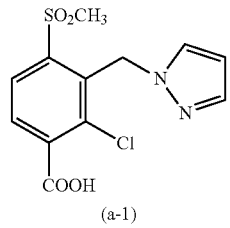 | ¹H NMR (DMSO-d₆, 500 MHz): δ 1.05-1.20 (m, 6H), 1.32 (t, 3H, J = 7.0 Hz), 2.31-2.46 (m, 4H), 3.19 (q, 2H, J = 7.0 Hz), 3.42 (s, 3H), 3.60 (s, 1H), 3.68 (s, 3H), 4.36 (s, 2H), 4.89 (s, 2H), 7.62 (d, 1H, J = 8.0 Hz), 7.99 (d, 1H, J = 8.0 Hz). |

SPECIFIC MODE FOR CARRYING OUT THE INVENTION

The content of the present invention is further explained in the following embodiments. The subject of the present invention should not be interpreted by those skilled in the art as being limited to the following examples: any techniques achieved on the basis of the content of the present invention should be included within the scope of the present invention. The technological parameters and production yield in the embodiments are presented without correction.

Embodiment 1

The method for preparing compound 01 in Table 1 is explicated in the embodiment. Compound 01 can be synthesized through the following reaction route:

Step 1: The Synthesis of Intermediate (a-1)

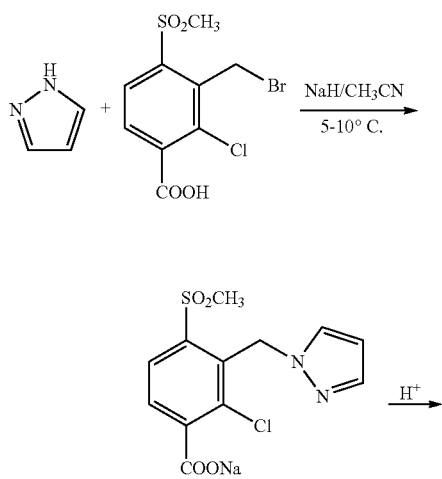

50 ml of acetonitrile was weighed and added into a 250 ml three-necked flask. The flask was placed in an ice-water bath, the temperature was controlled at 5 to 10° C. 3.0 g (0.075 mol) of 60% (mass fraction) NaH was weighed and slowly added into the three-necked flask. The temperature was controlled below 10° C. Then 2.4 g (0.036 mol) of pyrazole was dissolved into a little amount of acetonitrile, the obtained solution was put into a dropping funnel and dropped into the reaction system when the temperature was reduced to about 0° C. The mixture was kept stirring under the condition of ice-water bath after the dropping. When the temperature of the system became stable, 10 g (0.033 mol) of 2-chloro-3-bromomethyl-4-methylsulfonylbenzoic acid was weighed and slowly added in batches at a controlled temperature of no higher than 10° C. The system was stirred continuously in the ice-water bath after the addition. The reaction was tracked with HPLC until the raw material was consumed completely. Acetonitrile was removed through rotary evaporation, and 200 ml of water was added into the residue, followed by an addition of HCl drop by drop and stirred at room temperature to precipitated solid particles. The off-white solid, i.e. intermediate (a-1), was collected by sucking filtration and put into a drying oven for use later.

Step 2: The Synthesis of Intermediate (a-2)

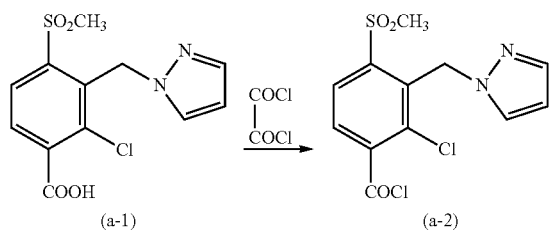

10 g (0.030 mol) of intermediate (a-1) was weighed and added into a 250 ml flask, followed by an addition of 50 ml of dichloroethane. A few drops of DMF was added into the resulting mixture as catalyst. Then 5 g (0.039 mol) of oxalyl chloride was dissolved into a little amount of dichloroethane and the obtained solution was put into a dropping funnel and dropped into the reaction system at room temperature. The reaction system was kept stirring for about 2 hours at room temperature after the addition to obtain the reaction solution containing intermediate (a-2). The reaction solution can be directly used for the next reaction without any treatment.

Step 3: The Synthesis of Intermediate a

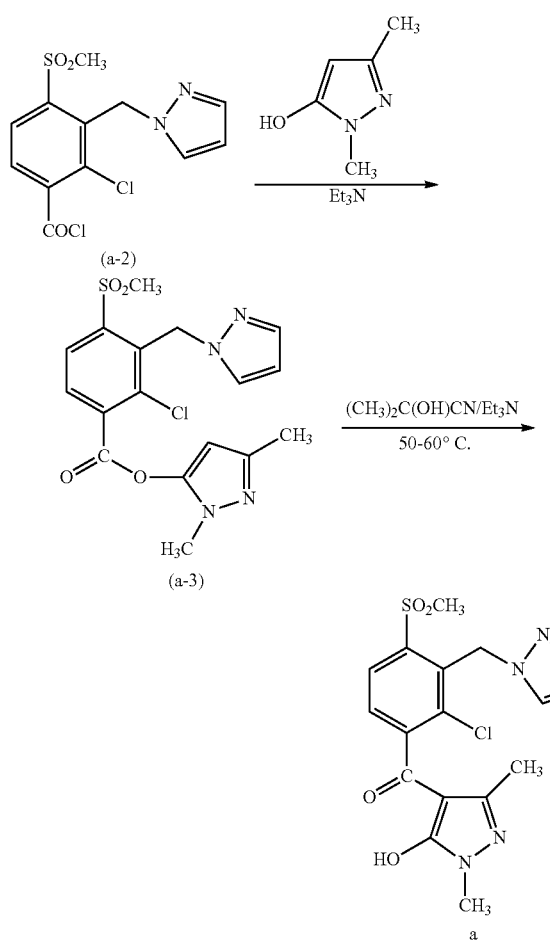

1.7 g (0.015 mol) of 1,3-dimethyl-5-pyrazol-ol was weighed and added into a 250 ml three-necked flask. 50 ml of 1,2-dichloroethane was added for dissolution. 4.0 g (0.040 mol) of triethylamine was weighed and added into the reaction system. The 1,2-dichloroethane solution of intermediate (a-2) (containing 0.010 mol intermediate (a-2)) was dropped into the reaction system under the condition of ice-water bath and argon protection. The reaction was tracked with HPLC after 1 hour. The reaction solution containing intermediate (a-3) was obtained after the raw material was consumed completely. 1.0 g (0.010 mol) of triethylamine and several drops of acetone cyanohydrins was added into the reaction solution containing intermediate (a-3) at a controlled temperature of 50 to 60° C. under argon protection. After reacting for 2 hours, the reaction was tracked with HPLC. 100 ml water was added when the reaction was complete, then slowly dropped with HCl with stirring at room temperature until pH was adjusted to about 3. The resulting aqueous layer was removed by extraction. The resulting organic layer was washed for 2 times with 200 ml of water, dried with anhydrous sodium sulfate, concentrated by rotary evaporation to obtain 3.6 g of pale brown powder solid as compound a.

Step 4: The Synthesis of Compound 01

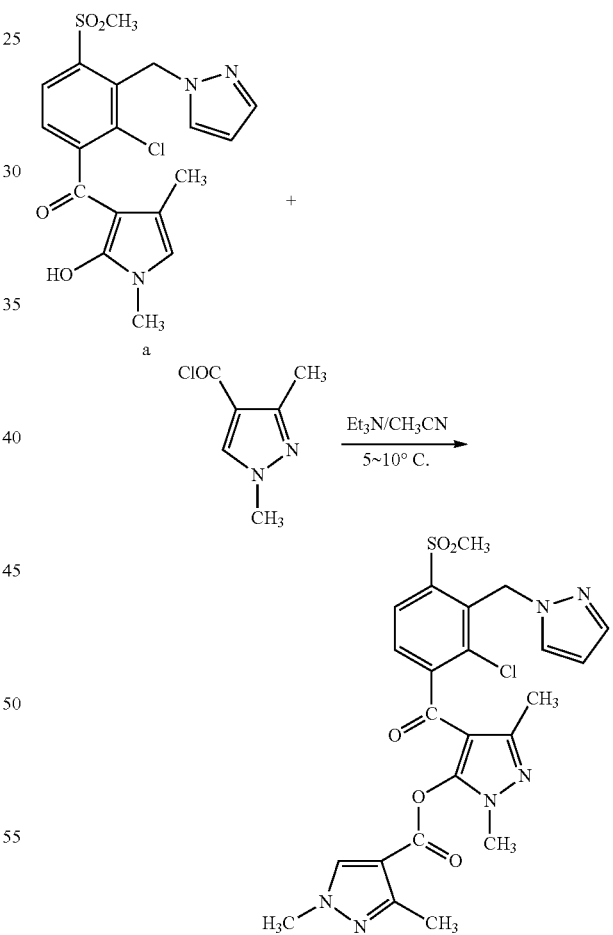

2.1 g (0.005 mol) of compound a was weighed and added into a 100 ml flask. 15 ml of acetonitrile and 1.0 g (0.010 mol) of triethylamine were added, the obtained mixture was stirred under the condition of ice water bath. 1.0 g (0.006 mol) of 1,3-dimethylpyrazole-4-formyl chloride was weighed and dissolved into 10 ml of acetonitrile. The solution was put into a dropping funnel and dropped under the condition of ice water bath. The reaction was tracked with HPLC until compound a was consumed completely. 100 ml of water and 100 ml of ethyl acetate were added into the reaction system when the reaction was complete. The resulting aqueous layer was removed by extraction. The resulting organic layer was washed for 2 times with 100 ml of saturated salt solution, dried with anhydrous sodium sulfate, concentrated by rotary evaporation to obtain the pale brown solid. 1.5 g of pale yellow powder solid, i.e. compound 01, was obtained after column chromatography purification. The content determined by HPLC was 93.9% and the yield was 53.1%.

$^1$H NMR data see Table 1.

Embodiments 2-13 provided the synthesis of compound 02 to compound 13 in Table 1, respectively, the synthetic methods of which were similar to that of embodiment 1, hence their description was not given here.

Embodiment 14

The embodiment explicated the synthesis of compound 14 in Table 1. Compound 14 can be synthesized through the following reaction route:

Step 1: The Synthesis of Intermediate (b-1)

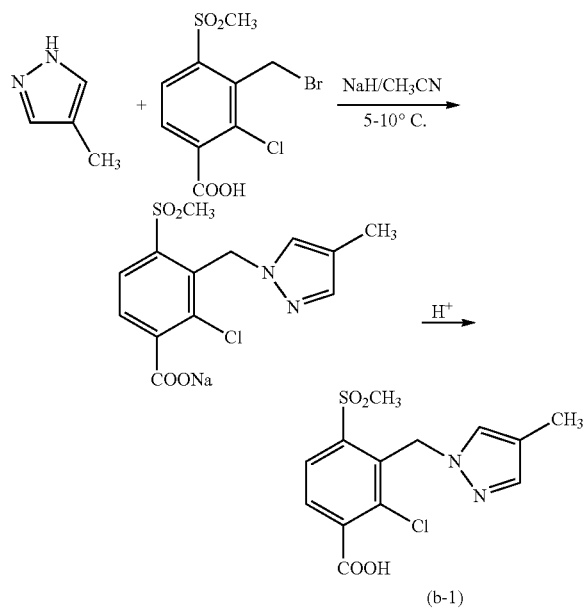

50 ml of acetonitrile was weighed and added into a 250 ml three-necked flask. The flask was put into an ice-water bath, and the temperature was controlled to 5 to 10° C. 3.0 g (0.075 mol) of NaH was weighed and slowly added into a three-necked flask at a controlled temperature of no higher than 10° C. 3 g (0.036 mol) of 4-methylpyrazol was weighed, then dissolved into a little amount of acetonitrile. The solution was put into a dropping funnel and added into the reaction system drop by drop when the temperature was reduced to about 0° C. The system was kept stirring under the condition of ice-water bath after the dropping. When the temperature became stable, 10 g (0.033 mol) of 2-chloro-3-bromomethyl-4-methylsulfonylbenzoic acid was weighed and added into the reaction system in batches at a controlled temperature of no higher than 10° C. with stirring under the condition of ice-water bath. The reaction was tracked with HPLC until the raw material was consumed completely. Acetonitrile was removed by rotary evaporation, the residue was add with 200 ml of water, then HCl was added drop by drop slowly and stirred at room temperature to precipitate solid particle. The particle was collected by sucking filtration to obtain an off-white solid, i.e., intermediate (b-1). The intermediate was placed into a drying oven for further use.

Step 2: The Synthesis of Intermediate (b-2)

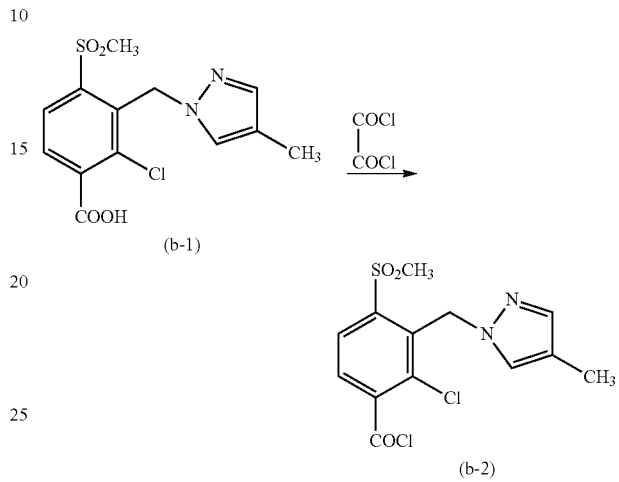

10 g (0.030 mol) of intermediate (b-1) was weighed and added into a 250 ml flask. 50 ml of dichloroethane was added and a little amount of DMF was dropped into the solution as catalyst. Then, 5 g (0.039 mol) of oxalyl chloride was weighed and dissolved into a little amount of dichloroethane. The obtained solution was put into a dropping funnel and dropped into the system at room temperature. The reaction system was kept stirring for about 2 hours at room temperature after the dropping to obtain the reaction solution containing intermediate (b-2). The reaction solution can be used directly for the next reaction without any treatment.

Step 3: Synthesis of Compound b

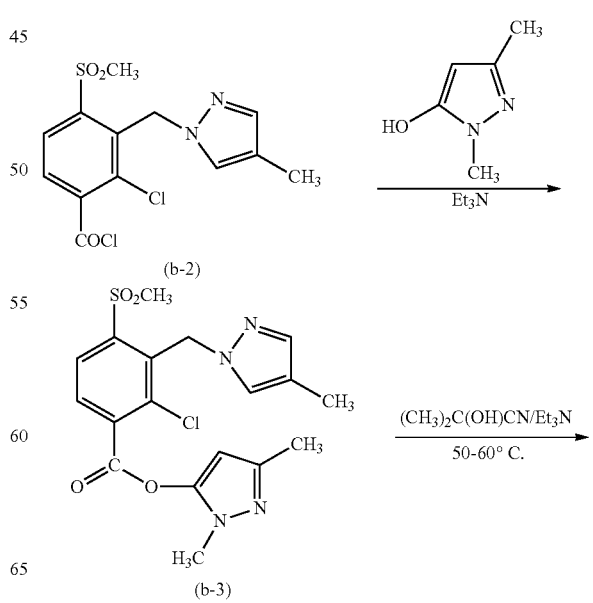

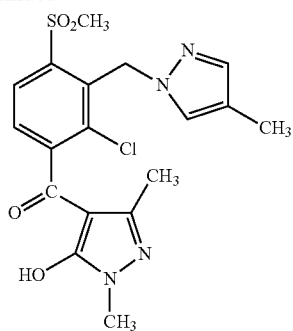

b 4.0 g (0.036 mol) of 1,3-dimethyl-5-pyrazol-ol was weighed and added into a 250 ml three-necked flask. 50 ml of 1,2-dichloroethane was added for dissolution. 12 g (0.12 mol) of triethylamine was weighed and put into the system. The reaction solution (0.030 mol) containing intermediate (b-2) was added drop by drop under the ice-water bath condition and argon protection. The reaction was tacked with HPLC after one hour, the reaction solution containing intermediate (b-3) was obtained when the raw material was consumed completely. 3.0 g (0.030 mol) of triethylamine and 0.5 ml of acetone cyanohydrin were added into the reaction solution containing intermediate (b-3) at a controlled temperature of 50 to 60° C. under argon protection and reacted for 2 hours, the reaction was tracked with HPLC. 100 ml of water was added when the reaction was complete, followed by an addition of HCl drop by drop slowly. The resulting mixture was stirred at room temperature until pH was adjusted to about 3. The aqueous layer was removed by extraction. The organic layer was washed for 2 times with 200 ml of water, dried with anhydrous sodium sulfate, concentrated by rotary evaporation to obtain 8.1 g of pale brown powder solid, i.e., compound b.

Step 4: The Synthesis of Compound 14

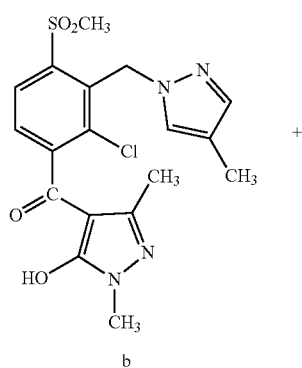

b

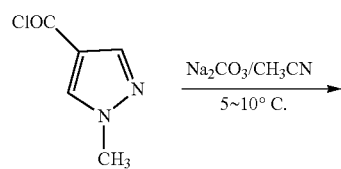

$\xrightarrow{\text{Na}_2\text{CO}_3/\text{CH}_3\text{CN}}{5\sim10°\text{C.}}$

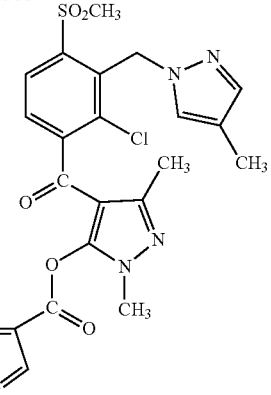

14

2.2 g (0.005 mol) of compound b was weighed and added into a 100 ml flask. 20 ml of acetonitrile and 1.0 g (0.010 mol) of sodium carbonate were added and stirred under the condition of ice-water bath. 0.8 g (0.0055 mol) of 1-methylpyrazole-4-formyl chloride was weighed and dissolved into 10 ml of acetonitrile. The obtained solution was put into a dropping funnel and dropped into the system under the condition of ice-water bath. The reaction was tracked with HPLC until compound b was consumed completely. Then 100 ml of water and 100 ml of ethyl acetate were added. The aqueous layer was removed by extraction. The organic layer was washed for 2 times with 100 ml of saturated salt solution, dried with anhydrous sodium sulfate, concentrated by rotary evaporation to obtain the dark brown grease, which was subjected to recrystallization in ethanol to afford 2.0 g of pale brown powder solid, i.e. compound 14. The content determined by HPLC was 94.1% and the yield was 70.9%.

$^1$H NMR data see Table 1.

Embodiments 15-22 provided the synthesis of compound 15 to compound 22 in Table 1, respectively, the synthetic methods of which were similar to that of embodiment 14, hence their description was not given here.

Embodiment 23

The embodiment explicated the specific synthesis for compound 23 in Table 1. Compound 23 can be synthesized through the following reaction route:

Step 1: The Synthesis of Intermediate (b-1)
See embodiment 14
Step 2: The Synthesis of Intermediate (b-2)
See embodiment 14
Step 3: The Synthesis of Compound c

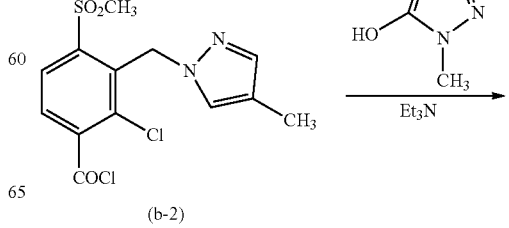

(b-2)

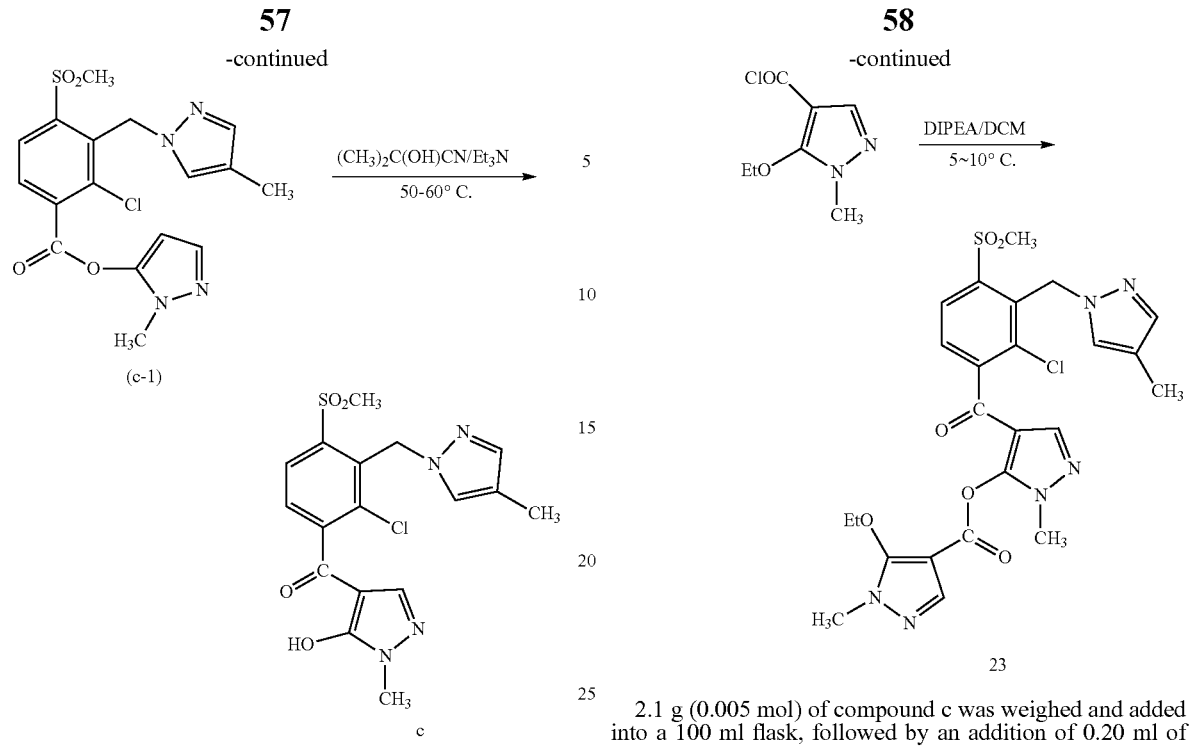

3.6 g (0.036 mol) of 1-methyl-5-pyrazol-ol was weighed and added into a 250 ml three-necked flask. 50 ml of 1,2-dichloroethane was added for dissolution. 12 g (0.12 mol) of triethylamine was weighed and added into the system. The reaction solution containing intermediate (b-2) (0.030 mol) was added into the system under the condition of ice-water bath and argon protection. The reaction was tracked with HPLC after 1 hour. The reaction solution containing intermediate (c-1) was obtained when the raw material was consumed completely. 3.0 g (0.030 mol) of triethylamine and 0.5 ml of acetone cyanohydrin were added into the reaction solution containing intermediate (c-1) at a controlled temperature of 50 to 60° C. under argon protection. The reaction was tracked with HPLC after 2 hours. 100 ml water was added when the reaction was complete, followed by an addition of HCl drop by drop slowly with stirring at room temperature until pH became about 3. The aqueous layer was removed by extraction. The organic layer was washed for 2 times with 200 ml water, dried with anhydrous sodium sulfate, concentrated by rotary evaporation to obtain 7.9 g of pale brown powder solid as compound c.

Step 4: The Synthesis of Compound 23

2.1 g (0.005 mol) of compound c was weighed and added into a 100 ml flask, followed by an addition of 0.20 ml of dichloromethane and 1.3 g (0.010 mol) of N,N-diisopropylethylamine, the resulting mixture was stirred under the condition of ice-water bath. 1.0 g (0.0055 mol) of 1-methyl-5-ethoxyl pyrazole-4-formyl chloride was weighed and dissolved into 10 ml of dichloromethane. The obtained solution was put into a dropping funnel and dropped into the reaction system under the condition of ice-water bath. The reaction was tracked with HPLC until compound c was consumed completely. Then 100 ml of water and 100 ml of dichloromethane were added. The obtained aqueous layer was removed by extraction. The obtained organic layer was washed for 2 times with 100 ml of saturated salt solution, dried with anhydrous sodium sulfate, concentrated by rotary evaporation to obtain the pale brown solid, which was subjected to recrystallization in 95% ethanol to obtain 1.9 g of pale yellow powder solid, i.e. compound 23. The content determined by HPLC was 95.1% and the yield was 64.4%.

$^1$H NMR data see Table 1.

Embodiment 24 provided the synthesis of compound 24 in table 1, the synthetic method of which is similar to that of embodiment 23, hence its description was not given here.

Embodiment 25

The embodiment explicated the specific synthesis for compound 25 in Table 1. Compound 25 can be synthesized through the following reaction route:

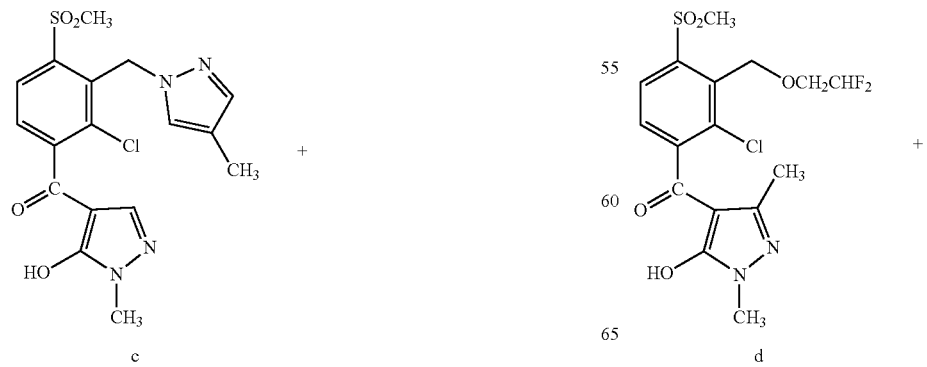

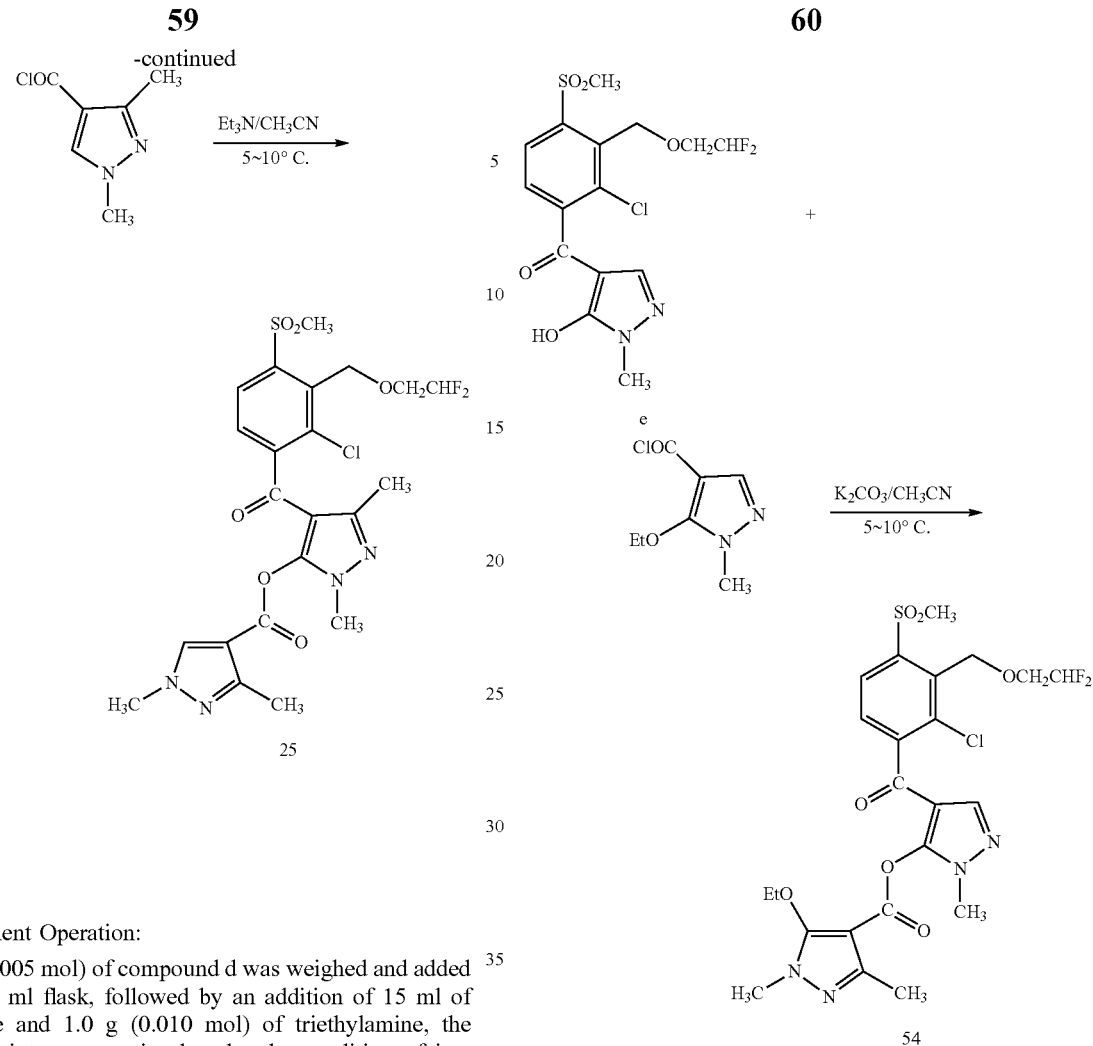

Experiment Operation:

2.2 g (0.005 mol) of compound d was weighed and added into a 100 ml flask, followed by an addition of 15 ml of acetonitrile and 1.0 g (0.010 mol) of triethylamine, the resulting mixture was stirred under the condition of ice-water bath. 1.0 g (0.006 mol) of 1,3-dimethyl pyrazole-4-formyl chloride was weighed and dissolved into 10 ml of acetonitrile. The solution was put into a dropping funnel and dropped into the reaction system under the condition of ice-water bath. The reaction was tracked with HPLC until compound d was consumed completely. Then 100 ml of water and 100 ml of ethyl acetate were added. The obtained aqueous layer was removed by extraction. The organic layer was washed for 2 times with 100 ml of saturated salt solution, dried with anhydrous sodium sulfate, concentrated by rotary evaporation to obtain the pale brown solid, which was subjected to recrystallization in 95% ethanol to obtain 1.7 g of pale yellow powder solid, i.e. compound 25. The content determined by HPLC was 92.3% and the yield was 57.6%.

$^1$H NMR data see Table 1.

Embodiments 26-53 provided the synthesis of compound 26 to compound 53 in Table 1, respectively, the synthetic methods of which were similar to that of embodiment 25, hence their description was not given here.

Embodiment 54

The embodiment explicated the synthesis for compound 54 in Table 1. Compound 54 can be synthesized through the following reaction route:

Experiment Operation 2.4 g (0.005 mol) of compound e was weighed and added into a 100 ml flask, followed by an addition of 20 ml of acetonitrile and 1.4 g (0.010 mol) of potassium carbonate, the resulting mixture was stirred under the condition of ice-water bath. 1.0 g (0.0055 mol) of 1-methyl-5-ethoxyl pyrazole-4-formyl chloride was weighed and dissolved into 10 ml of acetonitrile. The solution was put into a dropping funnel and dropped into the reaction system under the condition of ice-water bath. The reaction was tracked with HPLC until compound e was consumed completely. Then 100 ml of water and 100 ml of ethyl acetate were added. The obtained aqueous layer was removed by extraction. The obtained organic layer was washed for 2 times with 100 ml of saturated salt solution, dried with anhydrous sodium sulfate, concentrated by rotary evaporation to obtain the dark brown solid, which was subjected to recrystallization in 95% ethanol to obtain 2.1 g of yellow powder solid, i.e. compound 54. The content determined by HPLC was 94.3% and the yield was 68.3%.

$^1$H NMR data see Table 1.

Embodiments 55-59 provided the synthesis of compound 55 to compound 59 in Table 1, respectively, the synthetic methods of which were similar to that of embodiment 54, hence their description was not given here.

61

Embodiment 60

The embodiment explicated the synthesis for compound 60 in Table 1. Compound 60 can be synthesized through the following reaction route:

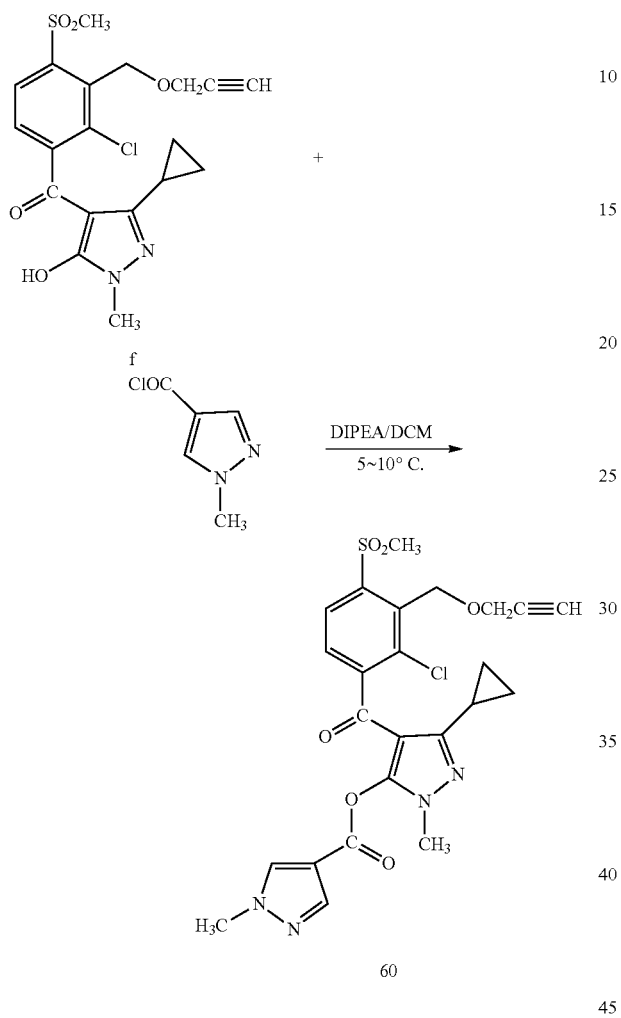

Experiment Operation 2.1 g (0.005 mol) of compound f was weighed and added into a 100 ml flask, followed by an addition of 20 ml of dichloromethane and 1.3 g (0.010 mol) of N,N-diisopropylethylamine, the resulting mixture was stirred under the condition of ice-water bath. 0.8 g (0.0055 mol) of 1-methyl pyrazole-4-formyl chloride was weighed and dissolved into 10 ml of dichloromethane. The obtained solution was put into a dropping funnel and dropped into the reaction system under the condition of ice-water bath. The reaction was tacked with HPLC until compound f was consumed completely. Then 100 ml of water and 100 ml of dichloromethane were added. The obtained aqueous layer was removed by extraction. The obtained organic layer was washed for 2 times with 100 ml of saturated salt solution, dried with anhydrous sodium sulfate, concentrated by rotary evaporation to obtain the dark brown solid, which was subjected to recrystallization in 95% ethanol to obtain 2.1 g of pale brown powder, i.e. compound 60. The content determined by HPLC was 95.7% and the yield was 76.6%.

1H NMR data see Table 1.

62

Embodiments 61-75 provided the synthesis of compound 61 to compound 75 in Table 1, respectively, the synthetic methods of which were similar to that of embodiment 60, hence their description was not given here.

Embodiment 76

The embodiment explicated the specific synthesis for compound 76 in Table 1. Compound 76 can be synthesized through the following reaction route:

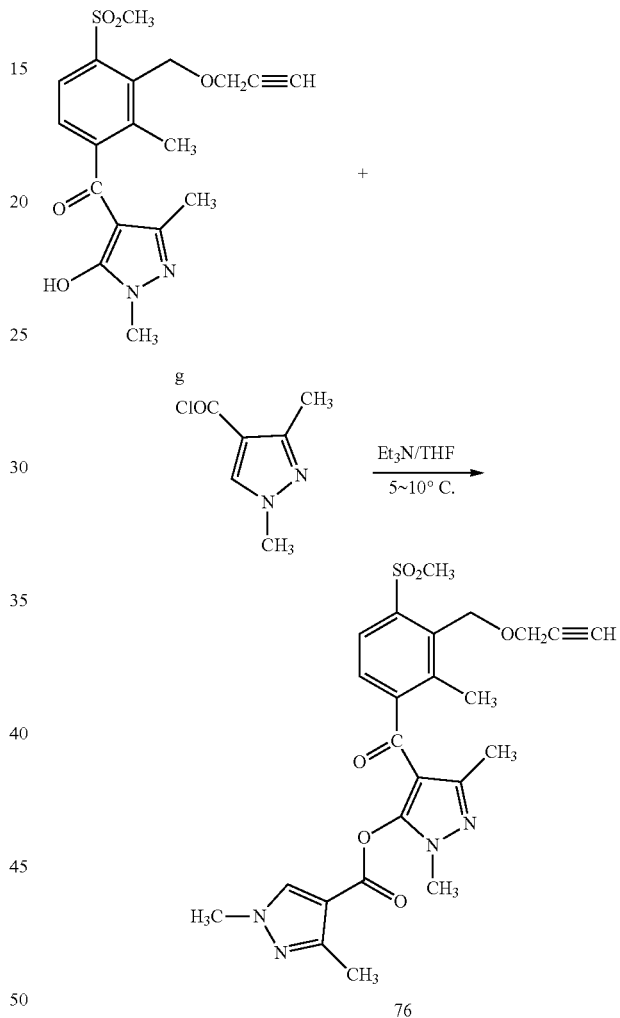

Experiment Operation 1.9 g (0.005 mol) of compound g was weighed and added into a 100 ml flask, followed by an addition of 20 ml of tetrahydrofuran and 1.0 g (0.010 mol) of triethylamine, the resulting mixture was stirred under the condition of ice-water bath. 0.9 g (0.0055 mol) of 1,3-dimethyl pyrazole-4-formyl chloride was weighed and dissolved into 10 ml of tetrahydrofuran. The obtained solution was put into a dropping funnel and dropped into the reaction system under the condition of ice-water bath. The reaction was tracked with HPLC until compound g was consumed completely. Then 100 ml of water and 100 ml of ethyl acetate were added. The obtained aqueous layer was removed by extraction. The obtained organic layer was washed for 2 times with 100 ml of saturated salt solution, dried with anhydrous sodium sulfate, concentrated by rotary evaporation to obtain the brown solid, which was subjected to recrystallization in 95% ethanol to obtain 1.8 g of pale brown powder solid, i.e. compound 76. The content determined by HPLC was 96.2% and the yield was 69.4%.

¹H NMR data see Table 1.

Embodiments 77-81 provided the synthesis of compound 77 to compound 81 in Table 1, respectively, the synthetic methods of which were similar to that of embodiment 76, hence their description was not given here.

Embodiment 82

The embodiment explicated the specific synthesis for compound 82 in Table 1. Compound 82 can be synthesized through the following reaction route:

Step 1: The Synthesis of Intermediate (h-1)

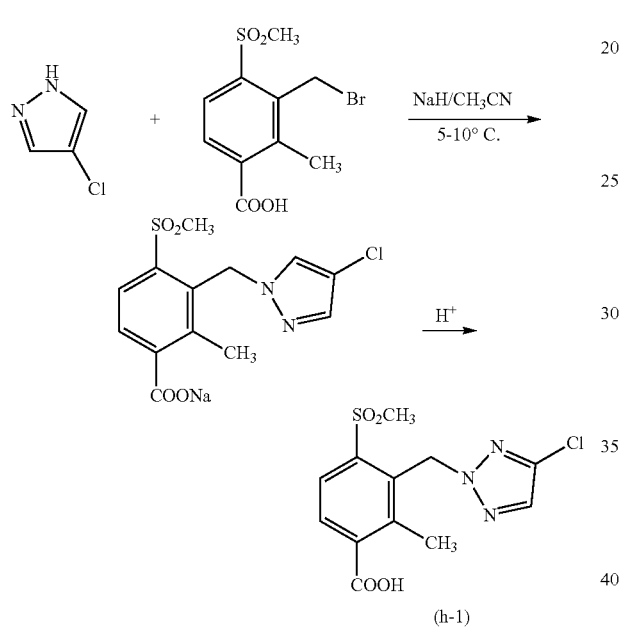

50 ml of acetonitrile was weighed and added into a 250 ml three-necked flask. The flask was placed in an ice-water bath for a controlled temperature of 5 to 10° C. 4.4 g (0.11 mol) of NaH was weighed and slowly added into the flask at a controlled temperature of no higher than 10° C. Then 4.6 g (0.045 mol) of 4-chloropyrazole was dissolved into a little amount of acetonitrile, the obtained solution was put into a dropping funnel and added into the reaction system drop by drop when the temperature of the reaction system was reduced to about 0° C. The reaction system was kept stirring under the condition of ice-water bath after the dropping. When the temperature of the system was stable, 10 g (0.034 mol) of 2-methyl-3-bromomethyl-4-methylsulfonyl benzoic acid was weighed and added slowly into the reaction system in batches at a controlled temperature of no higher than 10° C. with stirring under the condition of ice-water bath. The reaction was tracked with HPLC until the material was consumed completely. Acetonitrile was removed through rotary evaporation. 200 ml of water was added into the obtained residue, Followed by a slowly addition of HCl drop by drop with stirring at room temperature to precipitate particles. The off-white solid, i.e. intermediate (h-1), was obtained by sucking filtration. The intermediate was put into a drying oven for further use.

Step 2: The Synthesis of Intermediate (h-2)

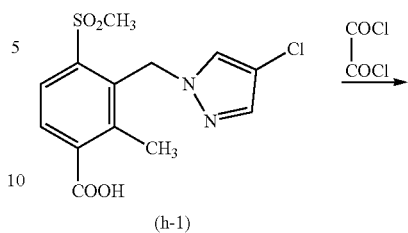

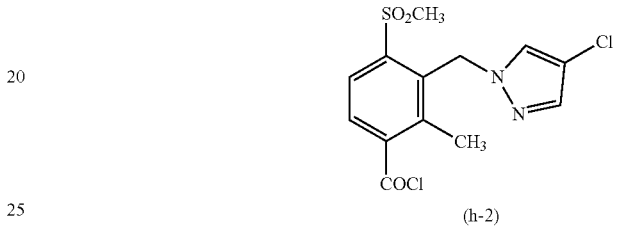

10.5 g (0.030 mol) of intermediate (h-1) was weighed and added into a 250 ml flask, followed by an addition of 50 ml of dichloroethane, a few drops of DMF was added as catalyst. Then, 5 g (0.039 mol) of oxalyl chloride was dissolved into a little amount of dichloroethane, the obtained solution was put into a dropping funnel and dropped into the reaction system at room temperature. The reaction system was continued to stir for about 2 hours at room temperature after the dropping to obtain the reaction solution containing intermediate (h-2). The reaction solution can be directly used for the next reaction without any treatment.

Step 3: The Synthesis of Compound h

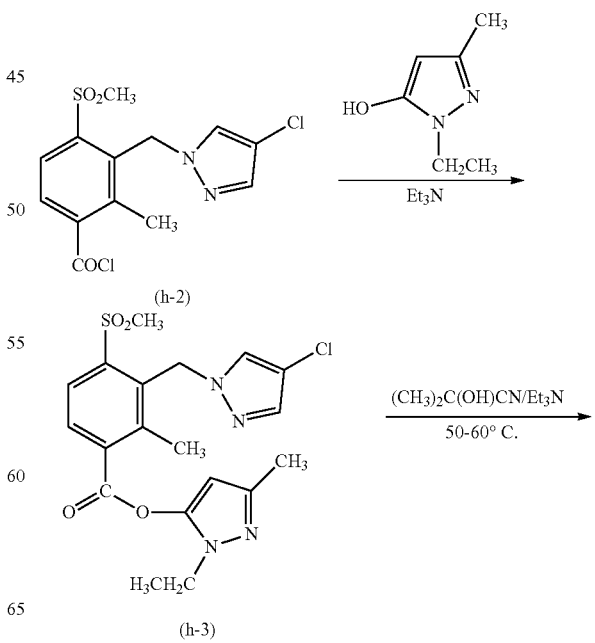

-continued

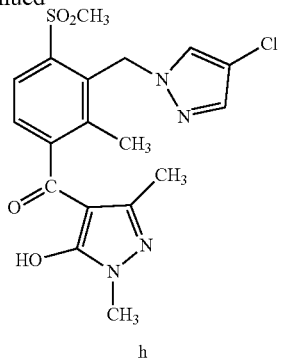

h

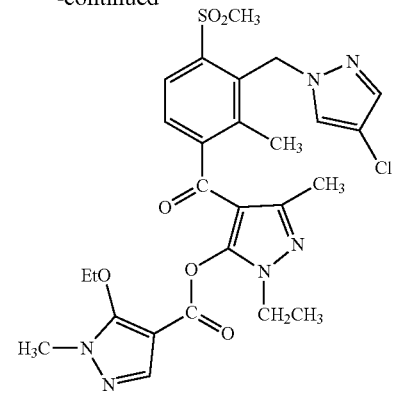

82

4.5 g (0.036 mol) of 1-ethyl-3-methyl-5-pyrazol-ol was weighed and added into a 250 ml three-necked flask. 50 ml of 1,2-dichloroethane was added for dissolution. 12 g (0.012 mol) of triethylamine was weighed and added into the system. The reaction solution (0.030 mol) containing intermediate (h-2) was dropped under the condition of ice-water bath into the system under argon protection. The reaction was tracked with HPLC after 1 hour. The reaction solution containing intermediate (h-3) was obtained when the raw material was consumed completely. 3.0 g (0.030 mol) of triethylamine and 0.5 ml of acetone cyanohydrin were added into the reaction solution containing intermediate (h-3) at a controlled temperature of 40 to 50° C. under argon protection. The reaction was tracked with HPLC after 2 hours. 100 ml water was added when the reaction was complete, followed by an addition of HCl drop by drop slowly with stirring at room temperature until pH was adjusted to about 3. The resulting aqueous layer was removed by extraction. The resulting organic layer was washed for 2 times with 200 ml water, dried with anhydrous sodium sulfate, concentrated by rotary evaporation to obtain 6.7 g of dark brown powder solid, i.e., compound h.

Step 4: The Synthesis of Compound 82

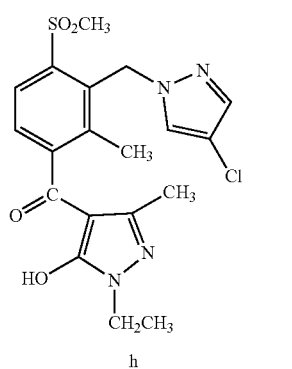

h

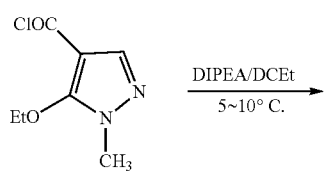

2.2 g (0.005 mol) of compound h was weighed and added into a 100 ml flask, followed by an addition of 20 ml of 1,2-dichloroethane and 1.3 g (0.010 mol) of N,N-diisopropylethylamine and stirred under the condition of ice-water bath. 1.0 g (0.0055 mol) of 1-methyl-5-ethoxyl pyrazole-4-formyl chloride was weighed and dissolved into 10 ml of 1,2-dichloroethane. The obtained solution was put into a dropping funnel and dropped into the reaction system under the condition of ice-water bath. The reaction was tracked with HPLC until compound h was consumed completely. Then 100 ml of water and 100 ml of dichloromethane were added. The resulting aqueous layer was removed by extraction. The resulting organic layer was washed for 2 times with 100 ml of saturated salt solution, dried with anhydrous sodium sulfate, concentrated by rotary evaporation to obtain the pale brown solid, which was subjected to recrystallization in 95% ethanol to obtain 1.9 g of yellow powder solid, i.e. compound 82. The content determined by HPLC was 93.8% and the yield was 62.0%.

$^1$H NMR data see Table 1.

Embodiments 83-87 provided the synthesis of compound 83 to compound 87 in Table 1, respectively, the synthetic methods of which were similar to that of embodiment 82, hence their description was not given here.

Embodiment 88

The embodiment explicated the synthesis for compound 88 in Table 1. Compound 88 can be synthesized through the following reaction route:

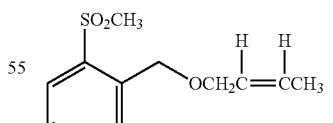

+

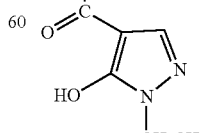

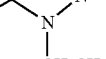

i

-continued

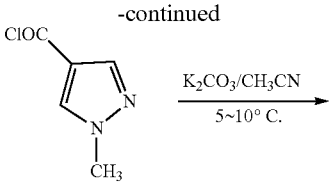

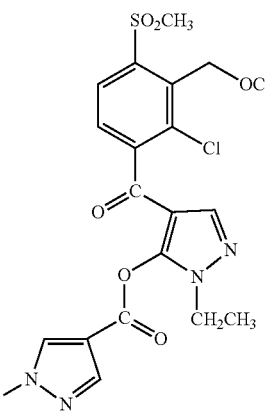

88

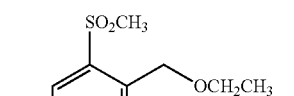

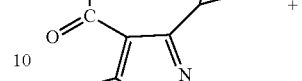

j

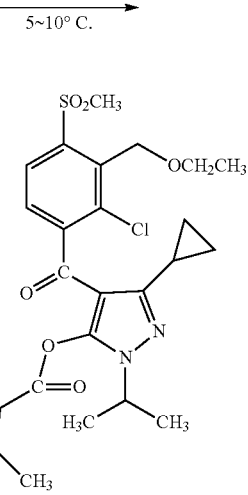

96

Experiment Operation 2.1 g (0.005 mol) of compound i was weighed and added into a 100 ml flask followed by an addition of 20 ml of acetonitrile and 1.4 g (0.010 mol) of potassium carbonate. The resulting mixture was stirred under the condition of ice-water bath. 0.8 g (0.0055 mol) of 1-methyl pyrazole-4-formyl chloride was weighed and dissolved into 10 ml of acetonitrile. The obtained solution was put into a dropping funnel and dropped into the reaction system under the condition of ice-water bath. The reaction was tracked with HPLC until compound i was consumed completely. Then 100 ml of water and 100 ml of ethyl acetate were added. The resulting aqueous layer was removed by extraction. The resulting organic layer was washed for 2 times with 100 ml of saturated salt solution, dried with anhydrous sodium sulfate, concentrated by rotary evaporation to obtain the dark brown solid, which was subjected to recrystallization in 95% ethanol to obtain 1.6 g of brown powder solid, i.e. compound 88. The content determined by HPLC was 90.6% and the yield was 57.2%.

$^1$H NMR data see Table 1.

Embodiments 89-95 provided the synthesis of compound 89 to compound 95 in Table 1, respectively, the synthetic methods of which were similar to that of embodiment 88, hence their description was not given here.

Embodiment 96

The embodiment explicated the specific synthesis for compound 96 in Table 1. Compound 96 can be synthesized through the following reaction route:

Experiment Operation 2.2 g (0.005 mol) of compound j was weighed and added into a 100 ml flask, followed by an addition of 20 ml of acetonitrile and 1.4 g (0.010 mol) of potassium carbonate. The resulting mixture was stirred under the condition of ice-water bath. 0.95 g (0.006 mol) of 1,3-dimethyl pyrazole-4-formyl chloride was weighed and dissolved into 10 ml of acetonitrile. The obtained solution was put into a dropping funnel and dropped into the reaction system under the condition of ice-water bath. The reaction was tracked with HPLC until compound j was consumed completely. Then 100 ml of water and 100 ml of ethyl acetate were added. The resulting aqueous layer was removed by extraction. The resulting organic layer was washed for 2 times with 100 ml of saturated salt solution, dried with anhydrous sodium sulfate, concentrated by rotary evaporation to obtain the dark brown solid, which was subjected to recrystallization in 95% ethanol to obtain 1.6 g of brown powder solid, i.e. compound 96. The content determined by HPLC was 94.7% and the yield was 53.8%.

$^1$H NMR data see Table 1.

Embodiments 97-101 provided the synthesis of compound 97 to compound 101, respectively, the synthetic methods of which were similar to that of embodiment 96, hence their description was not given here.

Embodiment 102

The embodiment explicated the specific synthesis for compound 102 in Table 1. Compound 102 can be synthesized through the following reaction route:

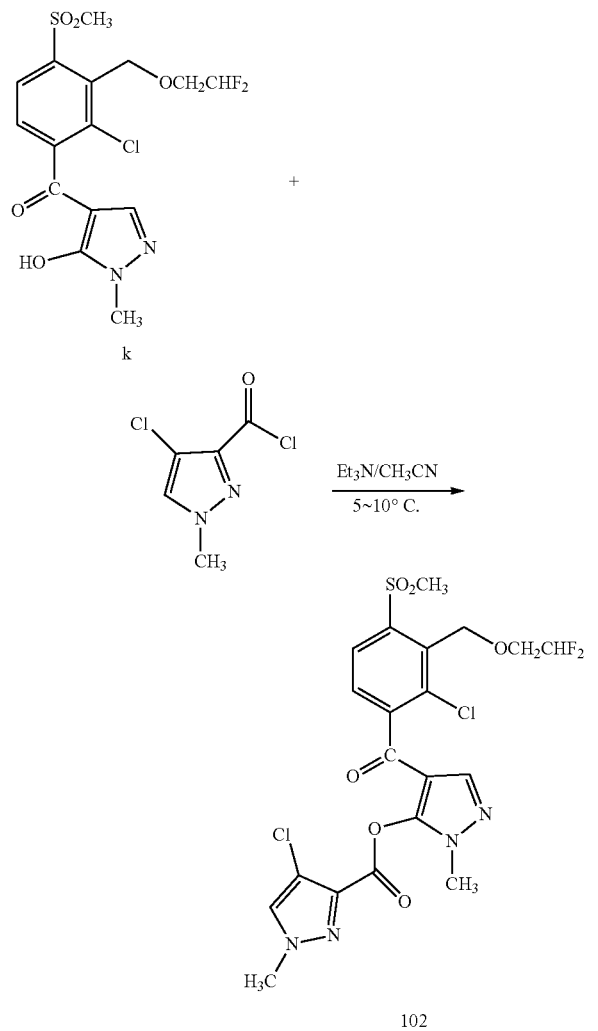

102

Experiment Operation 2.0 g (0.005 mol) of compound k was weighed and added into a 100 ml flask, followed by an addition of 20 ml of acetonitrile and 1.0 g (0.010 mol) of triethylamine. The resulting mixture was stirred under the condition of ice-water bath. 1.0 g (0.0055 mol) of 1-methyl-4-chloropyrazole-3-formyl chloride was weighed and dissolved into 10 ml of acetonitrile. The obtained solution was put into a dropping funnel and dropped into the reaction system under the condition of ice-water bath. The reaction was tracked with HPLC until compound k was consumed completely. Then 100 ml of water and 100 ml of ethyl acetate were added. The resulting aqueous layer was removed by extraction. The resulting organic layer was washed for 2 times with 100 ml of saturated salt solution, dried with anhydrous sodium sulfate, concentrated by rotary evaporation to obtain the brown solid, which was subjected to recrystallization in 95% ethanol to obtain 1.8 g of pale brown powder, i.e. compound 102. The content determined by HPLC was 96.2% and the yield was 62.8%.

$^1$H NMR data see Table 1.

Embodiments 103-104 provided the synthesis of compound 103 to compound 104 in Table 1, respectively, the synthetic methods of which were similar to that of embodiment 102, hence their description was not given here.

Embodiment 105

The embodiment explicated the specific synthesis for compound 105 in Table 1. Compound 105 can be synthesized through the following reaction route:

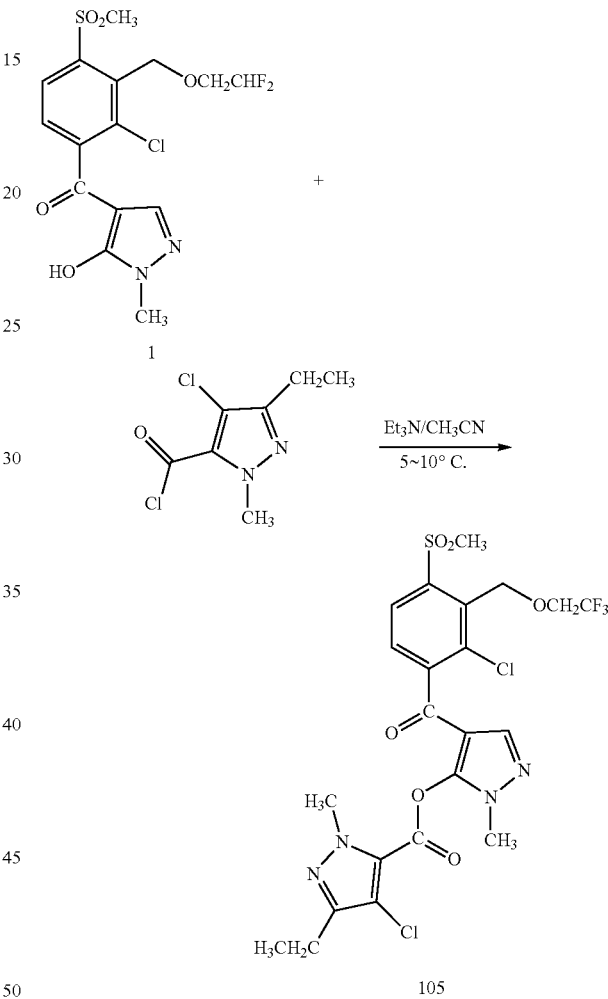

105

Experiment Operation 2.1 g (0.005 mol) of compound 1 was weighed and added into a 100 ml flask, followed by an addition of 15 ml of acetonitrile and 1.0 g (0.010 mol) of triethylamine. The resulting reaction mixture was stirred under the condition of ice-water bath. 1.2 g (0.006 mol) of 1-methyl-3-ethyl-4-chloropyrazole-5-formyl chloride was weighed and dissolved into 10 ml of acetonitrile. The obtained solution was put into a dropping funnel and dropped into the reaction system under the condition of ice-water bath. The reaction was tracked with HPLC until compound 1 was consumed completely. Then 100 ml of water and 100 ml of ethyl acetate were added. The resulting aqueous layer was removed by extraction. The resulting organic layer was washed for 2 times with 100 ml of saturated salt solution, dried with anhydrous sodium sulfate, concentrated by rotary evaporation to obtain the pale brown solid, which was subjected to recrystallization in 95% ethanol to obtain 1.7 g of pale yellow powder solid, i.e. compound 105. The content determined by HPLC was 95.3% and the yield was 54.2%.

$^1$H NMR data see Table 1.

Embodiments 106-107 provided the synthesis of compound 106 to compound 107 in Table 1, respectively, the synthetic methods of which were similar to that of embodiment 105, hence their description was not given here.

Biological Activity Evaluation:

The activity level standard of noxious plant destruction (i.e. growth inhibition rate) is as follows:

Level 10: completely dead;
Level 9: above 90% growth inhibition rate;
Level 8: above 80% growth inhibition rate;
Level 7: above 70% growth inhibition rate;
Level 6: above 60% growth inhibition rate;
Level 5: above 50% growth inhibition rate;
Level 4: above 30% growth inhibition rate;
Level 3: above 20% growth inhibition rate;
Level 2: above 10% growth inhibition rate;
Level 1: above 1-10% growth inhibition rate;
Level 0: no effect The above described growth control rate is fresh weight control rate.

Post-emergence test experiment: Monocotyledonous and dicotyledonous weed seeds and main crop seeds (i.e. wheat, corn, rice, soybean, cotton, oilseed, millet and *sorghum*.) were put into a plastic pot loaded with soil. Then covered with 0.5-2 cm soil, the seeds were allowed to grow in good greenhouse environment. The test plants were treated at 2-3 leaf stage 2-3 weeks after sowing. The test compounds of the invention were dissolved with acetone respectively, then added with 80 tween and diluted by certain amount of water to certain concentration. The solution was sprayed to the plants with a sprayer. Then the plants were cultured for 3 weeks in the greenhouse. The experiment result of weed controlling effect after 3 weeks was listed in table 2.

TABLE 2

EXPERIMENT ON WEED CONTROL EFFECT IN POST EMERGENCE STAGE

| Compound serial No. | g/ha | *Setaria viridis* | *Echinochloa crus-galli* | *Digitaria sanguinalis* | *Rorippa indica* | *Abutilon theophrasti* | *Bidens pilosa* | corn | wheat | rice |
|---|---|---|---|---|---|---|---|---|---|---|
| 1 | 60 | 10 | 10 | 10 | 10 | 10 | 8 | 1 | 1 | 1 |
| 2 | 120 | 6 | 10 | 2 | 10 | 8 | 9 | 0 | 0 | 1 |
| 3 | 120 | 6 | 10 | 0 | 0 | 4 | 6 | 0 | 0 | 0 |
| 4 | 120 | 5 | 10 | 1 | 4 | 6 | 6 | 0 | 0 | 0 |
| 5 | 120 | 5 | 10 | 9 | 10 | 9 | 8 | 0 | 0 | 1 |
| 6 | 120 | 6 | 10 | 2 | 10 | 7 | 9 | 0 | 0 | 1 |
| 7 | 120 | 5 | 10 | 1 | 4 | 6 | 6 | 0 | 0 | 0 |
| 8 | 60 | 7 | 9 | 7 | 10 | 10 | 8 | 1 | 1 | 1 |
| 9 | 120 | 6 | 9 | 2 | 10 | 7 | 9 | 0 | 0 | 1 |
| 10 | 120 | 7 | 10 | 2 | 10 | 7 | 9 | 0 | 0 | 1 |
| 11 | 120 | 6 | 10 | 0 | 0 | 4 | 6 | 0 | 0 | 0 |
| 12 | 120 | 1 | 10 | 0 | 4 | 6 | 6 | 0 | 0 | 0 |
| 13 | 60 | 7 | 10 | 10 | 10 | 10 | 8 | 0 | 1 | 1 |
| 14 | 120 | 1 | 10 | 0 | 4 | 6 | 6 | 0 | 0 | 0 |
| 15 | 120 | 5 | 10 | 4 | 10 | 9 | 8 | 0 | 0 | 1 |
| 16 | 60 | 8 | 10 | 10 | 10 | 10 | 8 | 1 | 1 | 1 |
| 17 | 120 | 1 | 10 | 0 | 4 | 6 | 6 | 0 | 0 | 0 |
| 18 | 120 | 5 | 10 | 4 | 10 | 9 | 8 | 0 | 0 | 1 |
| 19 | 60 | 8 | 10 | 10 | 10 | 10 | 8 | 0 | 0 | 1 |
| 20 | 120 | 5 | 10 | 1 | 4 | 6 | 6 | 0 | 0 | 0 |
| 21 | 120 | 3 | 10 | 1 | 4 | 6 | 6 | 0 | 0 | 0 |
| 22 | 120 | 3 | 10 | 1 | 4 | 6 | 6 | 0 | 0 | 0 |
| 23 | 120 | 3 | 10 | 1 | 4 | 6 | 6 | 0 | 0 | 0 |
| 24 | 120 | 2 | 9 | 1 | 4 | 6 | 6 | 0 | 0 | 0 |
| 25 | 30 | 9 | 10 | 10 | 5 | 7 | 7 | 0 | 0 | 6 |
| 26 | 30 | 10 | 10 | 10 | 8 | 7 | 8 | 1 | 0 | 5 |
| 27 | 30 | 6 | 9 | 7 | 5 | 7 | 7 | 0 | 0 | 6 |
| 28 | 30 | 5 | 9 | 7 | 5 | 7 | 7 | 0 | 0 | 6 |
| 29 | 15 | 10 | 8 | 9 | 4 | 8 | 5 | 0 | 0 | 3 |
| 30 | 120 | 10 | 8 | 4 | 4 | 6 | 6 | 0 | 0 | 0 |
| 31 | 30 | 9 | 10 | 10 | 5 | 7 | 7 | 0 | 0 | 5 |
| 32 | 30 | 10 | 10 | 10 | 5 | 7 | 7 | 1 | 0 | 5 |
| 33 | 30 | 9 | 9 | 9 | 5 | 7 | 7 | 1 | 0 | 5 |
| 34 | 60 | 8 | 10 | 10 | 10 | 10 | 8 | 0 | 0 | 1 |
| 35 | 30 | 6 | 10 | 7 | 5 | 7 | 7 | 1 | 0 | 5 |
| 36 | 60 | 7 | 10 | 10 | 10 | 10 | 8 | 0 | 0 | 1 |
| 37 | 60 | 5 | 9 | 10 | 10 | 10 | 8 | 0 | 0 | 1 |
| 38 | 60 | 10 | 8 | 8 | 10 | 10 | 8 | 0 | 0 | 1 |
| 39 | 60 | 10 | 10 | 9 | 10 | 10 | 8 | 0 | 0 | 1 |
| 40 | 30 | 9 | 10 | 10 | 10 | 7 | 7 | 0 | 0 | 5 |
| 41 | 30 | 10 | 10 | 8 | 10 | 7 | 7 | 0 | 0 | 5 |
| 42 | 30 | 9 | 10 | 7 | 10 | 7 | 7 | 0 | 0 | 5 |
| 43 | 30 | 9 | 10 | 7 | 10 | 7 | 7 | 0 | 0 | 3 |
| 44 | 30 | 9 | 10 | 10 | 10 | 7 | 7 | 0 | 0 | 3 |
| 45 | 30 | 7 | 9 | 7 | 10 | 7 | 7 | 0 | 0 | 3 |
| 46 | 30 | 10 | 10 | 10 | 10 | 7 | 7 | 1 | 0 | 3 |
| 47 | 30 | 9 | 10 | 7 | 10 | 7 | 7 | 0 | 0 | 3 |
| 48 | 30 | 9 | 10 | 7 | 10 | 7 | 7 | 0 | 0 | 3 |

TABLE 2-continued

EXPERIMENT ON WEED CONTROL EFFECT IN POST EMERGENCE STAGE

| Compound serial No. | g/ha | Setaria viridis | Echinochloa crus-galli | Digitaria sanguinalis | Rorippa indica | Abutilon theophrasti | Bidens pilosa | corn | wheat | rice |
|---|---|---|---|---|---|---|---|---|---|---|
| 49 | 30 | 9 | 10 | 7 | 10 | 7 | 7 | 0 | 0 | 3 |
| 50 | 30 | 9 | 10 | 8 | 10 | 6 | 7 | 0 | 0 | 3 |
| 51 | 30 | 10 | 10 | 10 | 10 | 7 | 7 | 4 | 0 | 3 |
| 52 | 30 | 6 | 10 | 7 | 10 | 7 | 7 | 1 | 0 | 3 |
| 53 | 30 | 6 | 10 | 8 | 10 | 7 | 7 | 1 | 0 | 3 |
| 54 | 30 | 10 | 10 | 7 | 10 | 7 | 7 | 1 | 0 | 3 |
| 55 | 30 | 10 | 10 | 10 | 10 | 7 | 7 | 2 | 0 | 3 |
| 56 | 30 | 9 | 10 | 7 | 10 | 7 | 7 | 0 | 0 | 3 |
| 57 | 30 | 9 | 10 | 7 | 10 | 7 | 7 | 0 | 0 | 3 |
| 58 | 30 | 9 | 10 | 7 | 10 | 7 | 7 | 0 | 0 | 3 |
| 59 | 30 | 6 | 8 | 7 | 10 | 7 | 7 | 0 | 0 | 3 |
| 60 | 30 | 7 | 10 | 7 | 7 | 6 | 4 | 0 | 0 | 5 |
| 61 | 30 | 5 | 10 | 7 | 10 | 7 | 7 | 0 | 0 | 3 |
| 62 | 30 | 7 | 10 | 7 | 10 | 7 | 7 | 0 | 0 | 3 |
| 63 | 30 | 10 | 10 | 10 | 10 | 7 | 7 | 1 | 0 | 6 |
| 64 | 30 | 10 | 10 | 9 | 10 | 5 | 5 | 2 | 0 | 3 |
| 65 | 30 | 6 | 10 | 7 | 10 | 6 | 7 | 0 | 0 | 3 |
| 66 | 30 | 5 | 10 | 7 | 10 | 7 | 7 | 0 | 0 | 3 |
| 67 | 30 | 9 | 10 | 7 | 10 | 7 | 7 | 1 | 0 | 3 |
| 68 | 30 | 9 | 10 | 7 | 10 | 7 | 7 | 0 | 0 | 3 |
| 69 | 30 | 6 | 10 | 6 | 10 | 7 | 7 | 0 | 0 | 3 |
| 70 | 30 | 10 | 10 | 10 | 10 | 7 | 7 | 3 | 0 | 3 |
| 71 | 30 | 5 | 8 | 7 | 10 | 6 | 8 | 0 | 0 | 3 |
| 72 | 30 | 8 | 10 | 8 | 10 | 7 | 7 | 2 | 0 | 3 |
| 73 | 30 | 9 | 10 | 9 | 10 | 7 | 7 | 0 | 0 | 3 |
| 74 | 30 | 6 | 10 | 6 | 10 | 7 | 5 | 0 | 0 | 3 |
| 75 | 30 | 7 | 10 | 9 | 10 | 5 | 6 | 0 | 0 | 3 |
| 76 | 30 | 10 | 10 | 7 | 10 | 7 | 7 | 1 | 0 | 3 |
| 77 | 30 | 10 | 10 | 7 | 10 | 7 | 7 | 1 | 0 | 3 |
| 78 | 30 | 10 | 10 | 7 | 10 | 7 | 7 | 1 | 0 | 3 |
| 79 | 120 | 3 | 10 | 1 | 4 | 6 | 6 | 0 | 0 | 0 |
| 80 | 30 | 6 | 10 | 7 | 10 | 6 | 7 | 0 | 0 | 3 |
| 81 | 120 | 3 | 10 | 1 | 4 | 6 | 6 | 0 | 0 | 0 |
| 82 | 120 | 3 | 10 | 1 | 4 | 6 | 6 | 0 | 0 | 0 |
| 83 | 30 | 8 | 9 | 8 | 10 | 6 | 7 | 0 | 0 | 3 |
| 84 | 120 | 3 | 10 | 1 | 4 | 6 | 6 | 0 | 0 | 0 |
| 85 | 30 | 8 | 9 | 8 | 10 | 6 | 7 | 0 | 0 | 3 |
| 86 | 30 | 8 | 8 | 8 | 10 | 6 | 7 | 0 | 0 | 3 |
| 87 | 120 | 3 | 10 | 1 | 4 | 6 | 6 | 0 | 0 | 0 |
| 88 | 30 | 8 | 7 | 8 | 10 | 6 | 7 | 0 | 0 | 3 |
| 89 | 30 | 8 | 10 | 7 | 10 | 7 | 7 | 1 | 0 | 1 |
| 90 | 30 | 10 | 10 | 10 | 10 | 7 | 7 | 1 | 0 | 3 |
| 91 | 120 | 3 | 10 | 1 | 4 | 6 | 6 | 0 | 0 | 0 |
| 92 | 30 | 10 | 10 | 8 | 10 | 5 | 7 | 1 | 0 | 3 |
| 93 | 120 | 3 | 10 | 1 | 4 | 6 | 6 | 0 | 0 | 0 |
| 94 | 60 | 10 | 8 | 8 | 10 | 10 | 8 | 0 | 0 | 3 |
| 95 | 120 | 3 | 10 | 1 | 4 | 6 | 6 | 0 | 0 | 0 |
| 96 | 60 | 10 | 10 | 8 | 10 | 10 | 8 | 0 | 0 | 4 |
| 97 | 120 | 3 | 10 | 1 | 4 | 6 | 6 | 0 | 0 | 0 |
| 98 | 30 | 10 | 10 | 8 | 10 | 5 | 7 | 1 | 0 | 5 |
| 99 | 30 | 8 | 10 | 7 | 10 | 7 | 7 | 1 | 0 | 1 |
| 100 | 30 | 10 | 10 | 7 | 10 | 7 | 7 | 1 | 0 | 5 |
| 101 | 250 | 7 | 9 | 6 | 10 | 7 | 7 | 1 | 0 | 8 |
| 102 | 30 | 6 | 10 | 7 | 10 | 7 | 7 | 1 | 0 | 5 |
| 103 | 120 | 3 | 10 | 2 | 10 | 7 | 7 | 1 | 0 | 0 |
| 104 | 60 | 10 | 10 | 10 | 10 | 10 | 8 | 0 | 0 | 4 |
| 105 | 60 | 10 | 10 | 9 | 10 | 10 | 8 | 0 | 0 | 4 |
| 106 | 60 | 10 | 10 | 8 | 10 | 10 | 8 | 0 | 0 | 1 |
| 107 | 60 | 10 | 10 | 8 | 10 | 10 | 8 | 0 | 0 | 7 |

Experiment on Weed Effect in Pre-Emergence Stage

Seeds of monocotyledonous and dicotyledonous weeds and main crops (e.g. wheat, corn, rice, soybean, cotton, oilseed, millet and *Sorghum*) were put into a plastic pot loaded with soil and covered with 0.5-2 cm soil. The test compounds of the present invention was dissolved with acetone, then added with tween 80, diluted by a certain amount of water to reach a certain concentration, and sprayed immediately after sowing. The obtained seeds were incubated for 4 weeks in the greenhouse after spraying. The test results were observed 3 weeks later. It was observed that the herbicide mostly had excellent effect at the application rate of 250 g/ha, especially to weeds such as *Echinochloa crus-galli*, *Digitaria sanguinalis* and *Abutilon theophrasti*, etc. Many compounds had good selectivity for corn, wheat, rice, soybean, oilseed rape, etc.

Transplanted rice safety evaluation and weed control effect evaluation in rice field:

Rice field soil was loaded into a $1/1,000,000$ ha pot. The seeds of *Echinochloa*, *Scirpus juncoides*, *Bidens tripartite* and *Sagittaria trifolia* were sowed and gently covered with soil, then left to stand still in greenhouse in the state of 0.5-1 cm of water storage. The tuber of *Sagittaria trifolia* was planted in the next day or 2 days later. It was kept at 3-4 cm of water storage thereafter. The weeds were treated by dripping the WP or SC water diluents prepared according to the common preparation method of the compounds of the present invention with pipette homogeneously to achieve specified effective amount when *Echinochloa*, *Scirpus juncoides* and *Bidens tripartite* reached 0.5 leaf stage and *Sagittaria trifolia* reached the time point of primary leaf stage.

In addition, the rice field soil that loaded into the 1/1,000,000 ha pot was leveled to keep water storage at 3-4 cm depth. The 3 leaf stage rice (*japonica* rice) was transplanted at 3 cm of transplanting depth the next day. The compound of the present invention was treated by the same way after 5 days of transplantation.

The fertility condition of *Echinochloa*, *Scirpus juncoides*, *Bidens tripartite* and *Sagittaria trifolia* 14 days after the treatment of the compound of the invention and the fertility condition of rice 21 days after the treatment of the compound of the invention respectively with the naked eye. Evaluate the weed control effect with 1-10 activity standard level, which was presented in table 3.

TABLE 3

THE EXPERIMENT RESULTS OF WEED CONTROL EFFECT IN TRANSPLANTED RICE FIELD (500 G A.I./HA)

| Compound serial No. | Echinochloa crus-galli | Scirpus juncoides | Monochoria vaginalis | Rice | Application Rate (g/ha) |
|---|---|---|---|---|---|
| 2 | 10 | 10 | 9 | 0 | 500 |
| 6 | 10 | 10 | 10 | 1 | 500 |
| 10 | 10 | 10 | 10 | 1 | 500 |
| 24 | 10 | 10 | 9 | 1 | 60 |
| 36 | 9 | 10 | 10 | 0 | 60 |
| 40 | 10 | 9 | 9 | 0 | 60 |
| 46 | 8 | 9 | 9 | 0 | 60 |
| 51 | 10 | 9 | 10 | 0 | 60 |
| 60 | 10 | 10 | 10 | 2 | 60 |
| 68 | 7 | 10 | 10 | 1 | 60 |
| 76 | 10 | 10 | 10 | 0 | 60 |
| 90 | 10 | 10 | 10 | 0 | 60 |
| 100 | 10 | 10 | 8 | 0 | 60 |
| 107 | 9 | 10 | 10 | 10 | 60 |

The seeds of *Echinochloa crus-galli*, *Scirpus juncoides* and *Monochoria vaginalis* were collected from Heilongjing and Jiangsu Province of China. Tests indicated that the weeds were resistant to common rate of pyrazosulfuron-ethyl.

Control Experiment:
Compound A as Control:

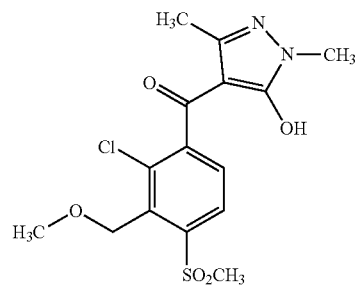

Compound B as Control:

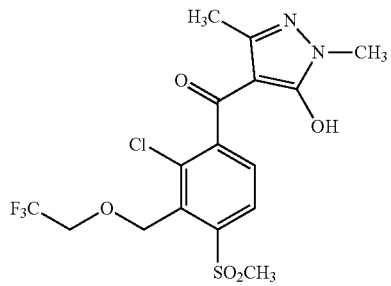 [SMILES: Cc1nn(C)c(O)c1C(=O)c1ccc(S(C)(=O)=O)c(COCC(F)(F)F)c1Cl]

The control compounds were selected from those presented in patent CN88101455A.

Test in post-emergence stage: seeds of monocotyledonous weeds and corn were put into a plastic pot loaded with soil, covered with 0.5-2 cm soil, and allowed to grow in good greenhouse environment. The test plants were treated at 5-6 leaf stage 4 weeks after sowing. The test compounds of the present invention were dissolved with acetone respectively, then added with tween 80, diluted by a certain amount of water to reach a certain concentration. The solution was sprayed to the plants by a spray tower. The test application rate was 15 g/ha and the observe time was 25 day.

TABLE 4

RESULT OF THE CONTROL EXPERIMENT

| Compound | Digitaria sanguinalis | Echinochloa crus-galli | Setaria viridis | Corn |
|---|---|---|---|---|
| Compound 26 | 10 | 10 | 10 | 0 |
| Compound A as control | 6 | 7 | 7 | 1 |
| Compound 29 | 10 | 8 | 9 | 0 |
| Compound B as control | 5 | 6 | 7 | 0 |

Table 4 indicates that the compounds of the present invention have better herbicidal activity and safety than the compounds as control.

At the same time, it is found after several tests that the compound of the present invention has good selectivity to many gramineae grass such as *Zoysia japonica*, bermuda grass, tall fescue, bluegrass, ryegrass and seashore *Paspalum* etc, and is able to control many important grass weeds and broadleaf weeds. The compound also shows excellent selectivity and commercial value in the tests on soybean, cotton, oil sunflower, potato, orchards and vegetables in different herbicide application methods.

The invention claimed is:
1. A pyrazole compound or a salt thereof of formula (I'):

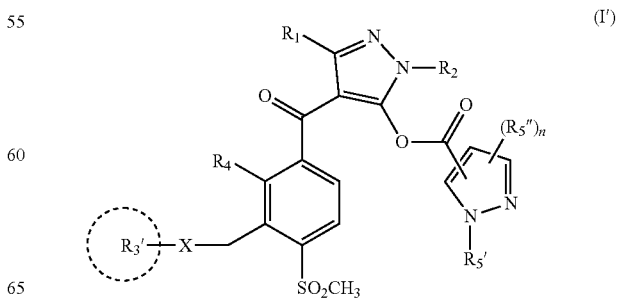

wherein,

R₁ is hydrogen or C1-C4 alkyl;

R₂ is C1-C3 alkyl;

X is O, N or S, X and R₃' may form a ring or a linear chain, wherein, when X is O or S, R₃' is C1-C6 alkyl, C3-C6 alkoxyl alkyl, C2-C6 halogenated alkyl, C3-C6 alkenyl or C3-C6 alkynyl; when X is N, X and R₃' form a pyrazole ring or substituted pyrazole ring, C3-C5 lactam ring or substituted lactam ring;

R₄ is C1-C3 alkyl or halogen;

R₅' is hydrogen or C1-C3 alkyl;

R₅" is hydrogen, C1-C3 alkyl, C1-C3 alkoxyl, C1-C3 halogenated alkyl, halogen, amino or nitro; and n is 0, 1 or 2, wherein, when n is 2, the two R₅" may be the same or different.

2. The pyrazole compound or the salt thereof according to claim 1, wherein

R₁ is hydrogen, methyl, ethyl or cyclopropyl;

R₂ is methyl, ethyl or isopropyl;

X is O, N or S, X and R₃' may form a ring or a linear chain, wherein, when X is O or S, R₃' is C1-C6 alkyl, C3-C6 alkoxyl alkyl, C2-C4 halogenated alkyl, C3-C5 alkenyl or C3-C5 alkynyl; when X is N, X and R₃' form a pyrazole ring or substituted pyrazole ring, C3-C5 lactam ring or substituted lactam ring R₄ is methyl or chlorine;

R₅' is hydrogen, methyl, ethyl or isopropyl;

R₅" is hydrogen, methyl, ethyl, isopropyl, methoxyl, ethoxyl, difluoromethyl, chloro or bromo; and n is 0, 1, or 2, wherein, when n is 2, the two R₅" may be the same or different.

3. The pyrazole compound or the salt thereof according to claim 2, wherein X is O or N, X and R₃' may form a ring or a linear chain, wherein, when X is O, R₃' is methyl, ethyl, n-butyl, methoxyl ethyl, ethoxyl ethyl, methoxyl isopropyl, methoxyl n-propyl, 2,2-difluoroethyl, 2,2,2-trifluoroethyl, 1,1,2,2-tetrafluoropropyl, propargyl, 2-butenyl or tetrahydrofurfuryl; when X is N, X and R₃' form a pyrazole ring, 3-methyl pyrazole ring, 4-methyl pyrazole ring, 3,5-dimethyl pyrazole ring, 4-chloropyrazole ring or pyrrolidone ring.

4. An herbicidal composition comprising an herbicidally effective amount of at least one pyrazole compound or the salt thereof according to claim 1.

5. The herbicidal composition according to claim 4, further comprising a preparation auxiliary.

6. The pyrazole compound or the salt thereof according to claim 1, wherein the compound is selected from

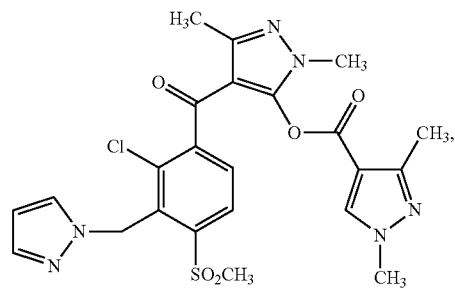

01

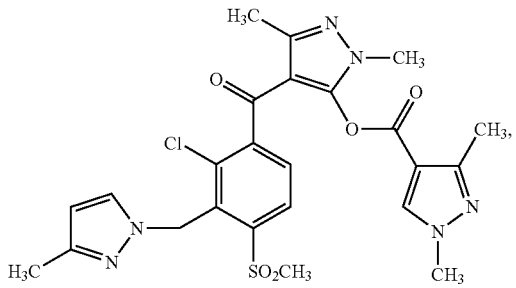

02

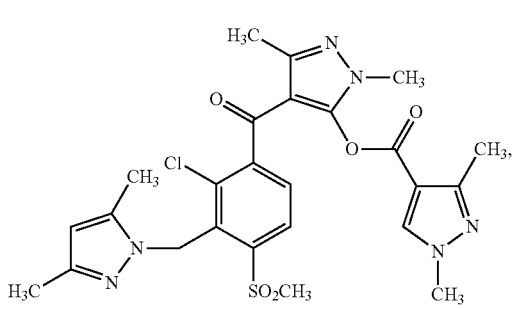

03

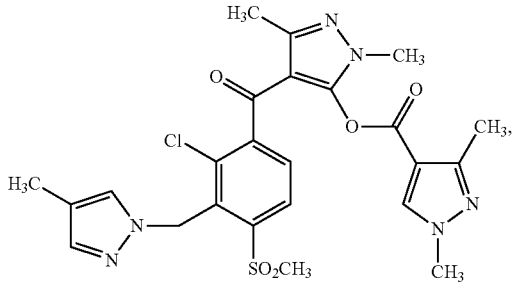

04

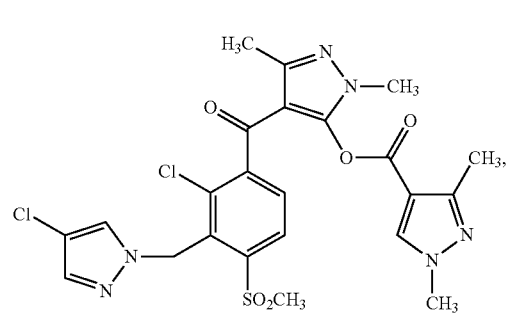

05

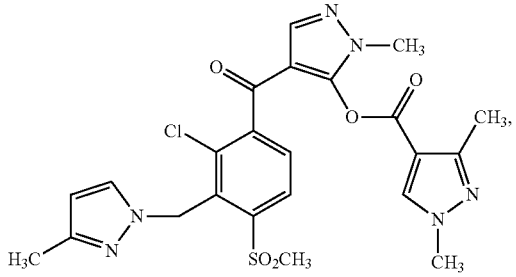

06

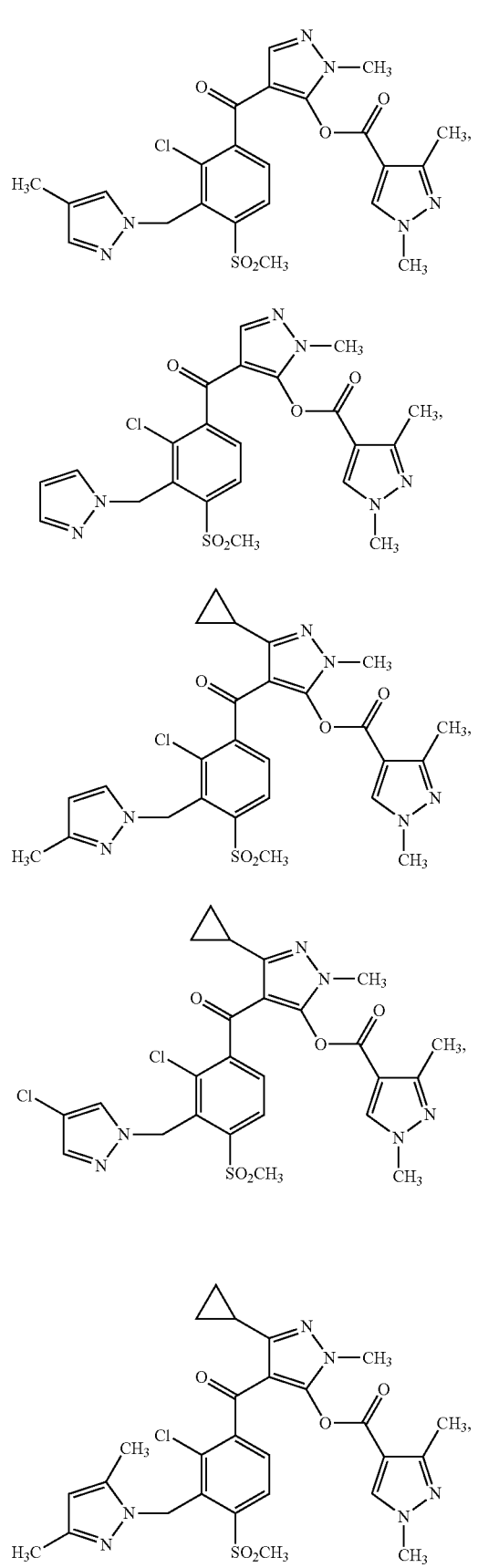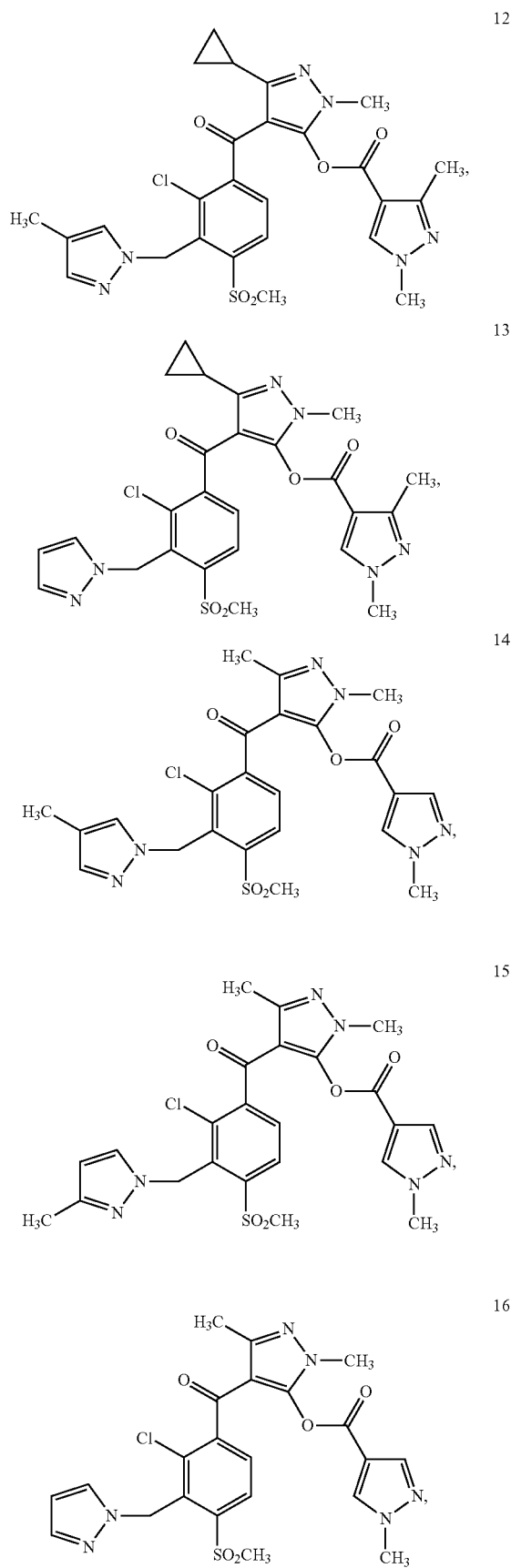

17
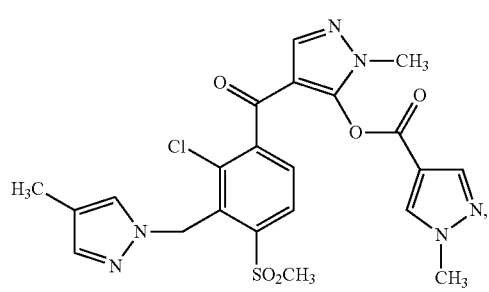
18
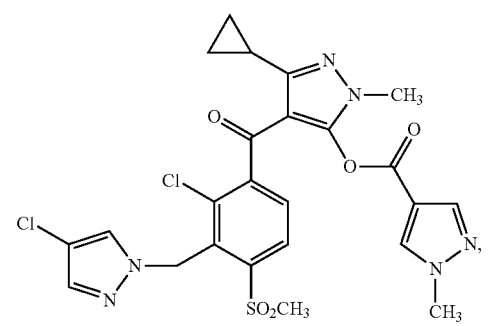
19
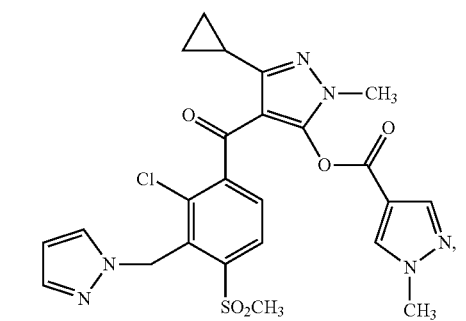
20
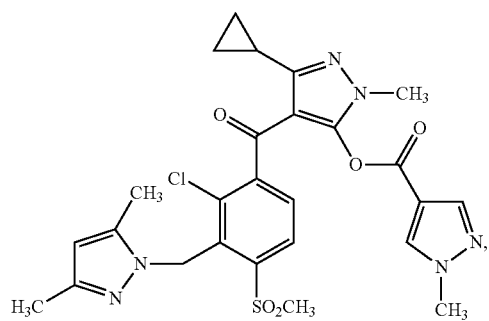
21
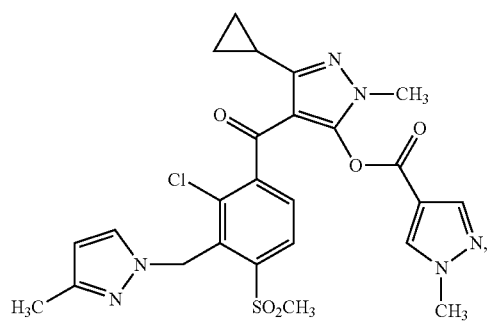
22
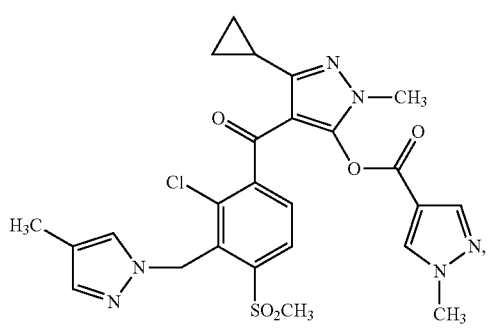
23
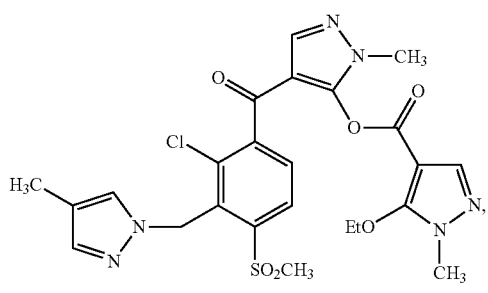
24
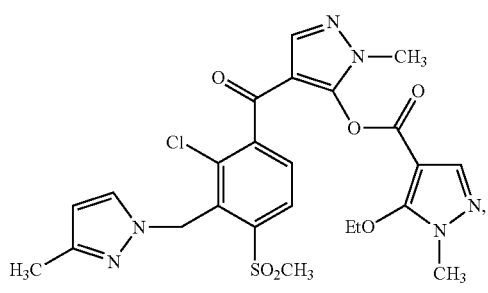
25
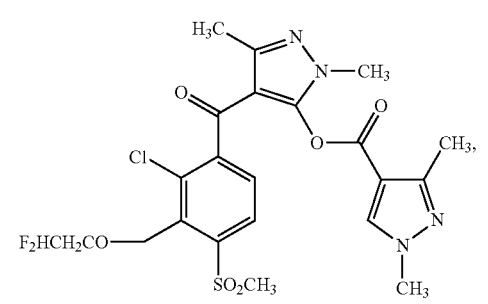
26
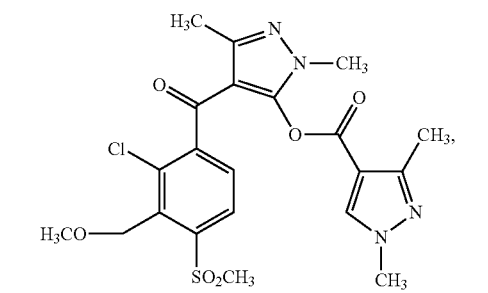

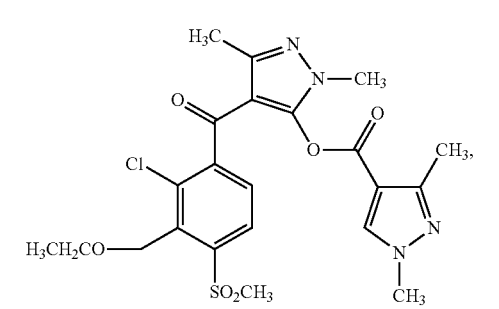
27
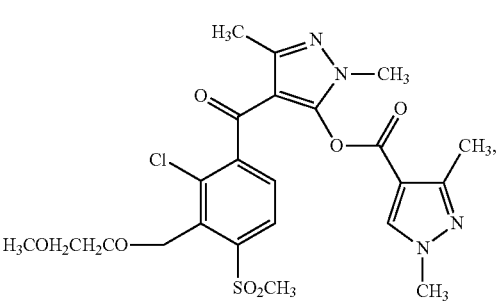
28
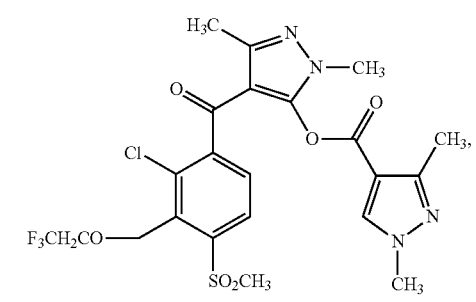
29
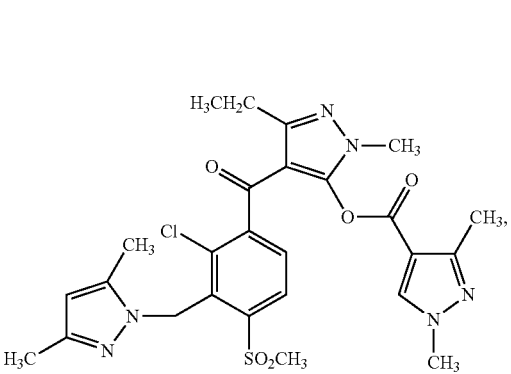
30
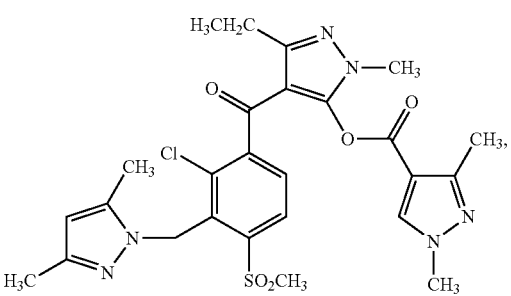
31
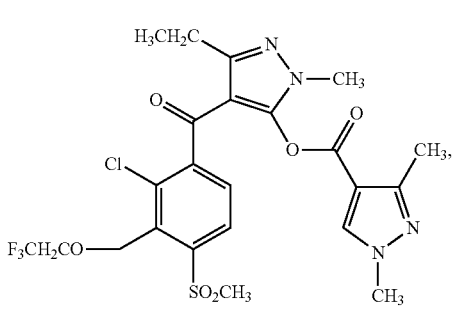
32
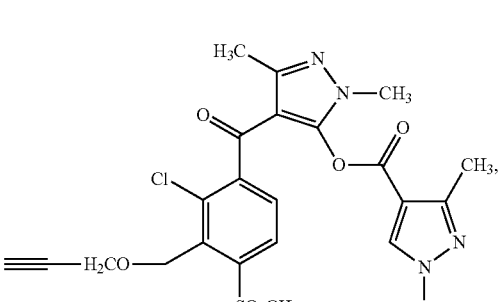
33
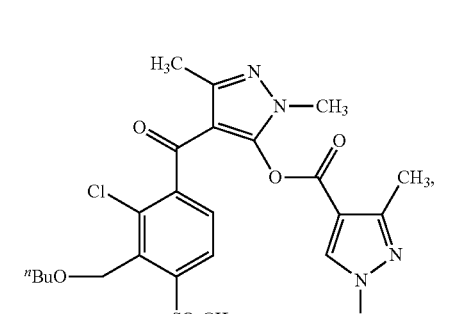
34
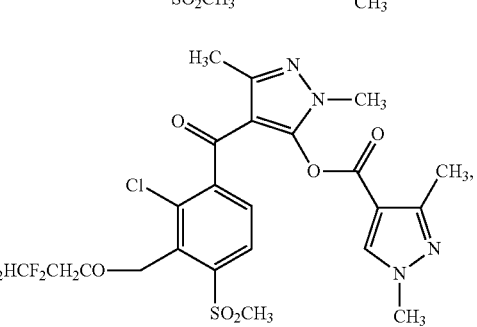
35
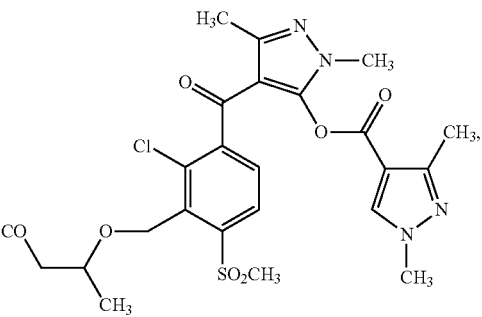
36

37
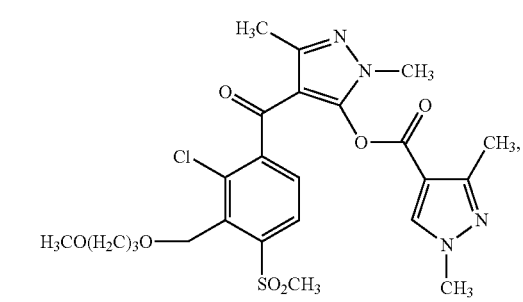
38
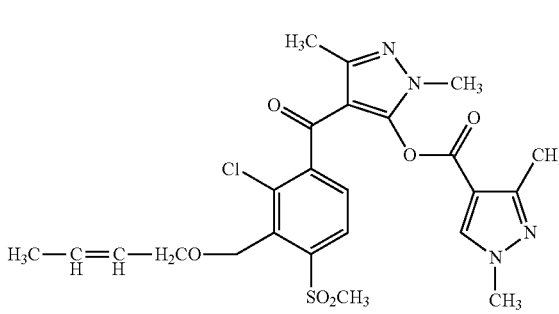
39
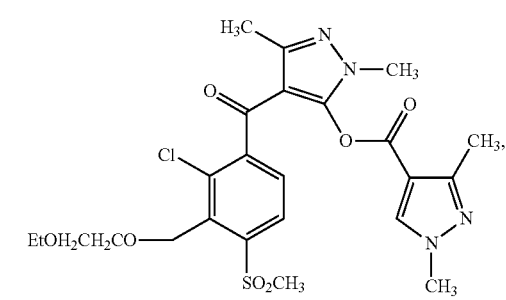
40
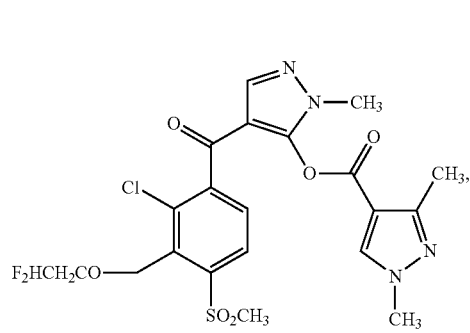
41
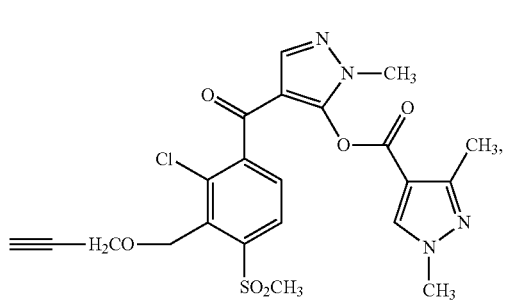
42
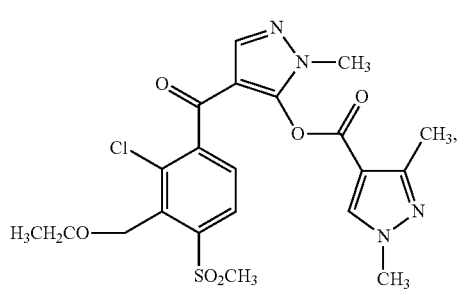
43
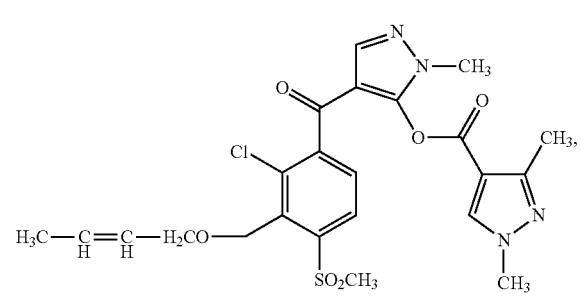
44
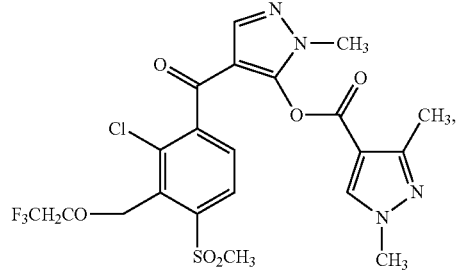
45
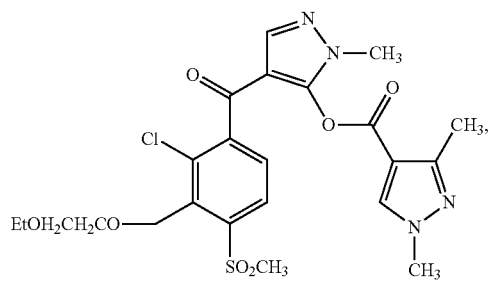
46
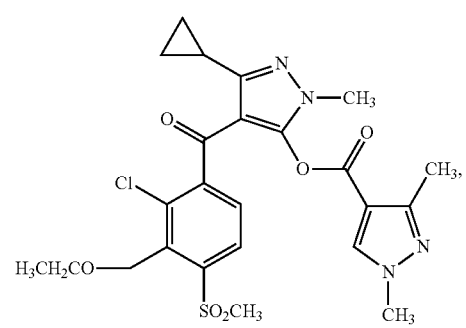

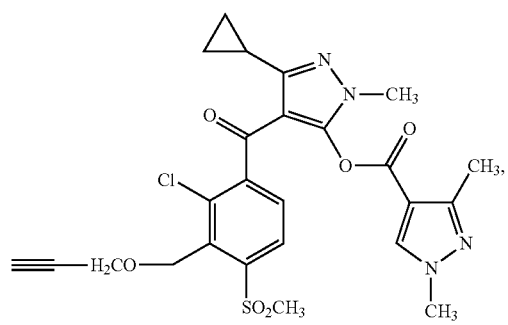
47
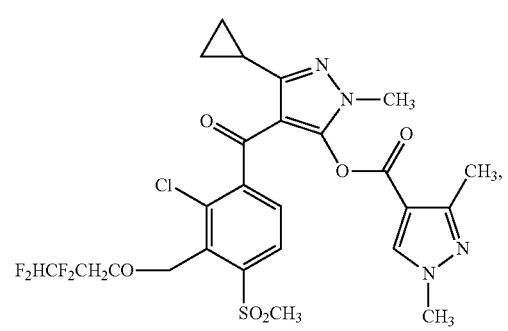
48
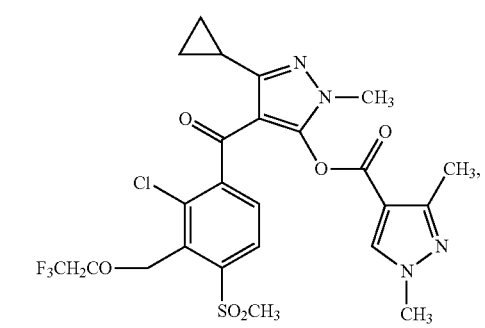
49
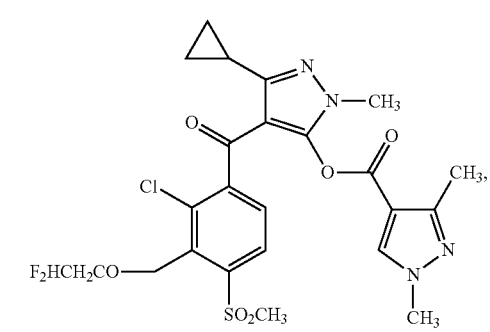
50
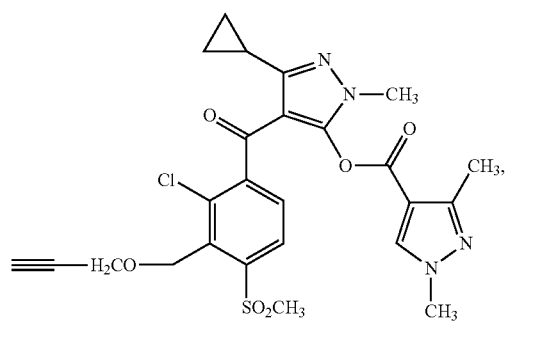
51
52
53
54
55

56
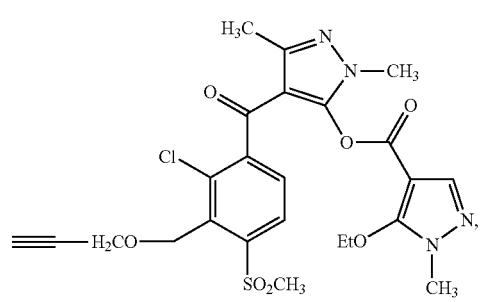
57
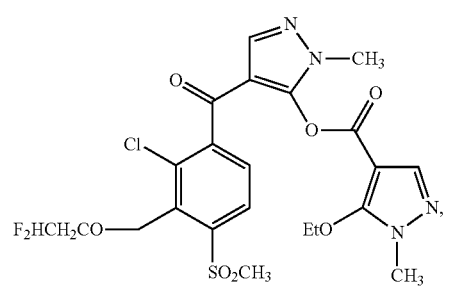
58
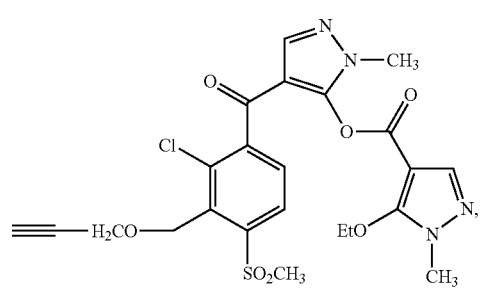
59
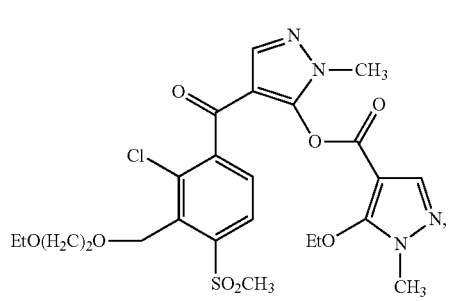
60
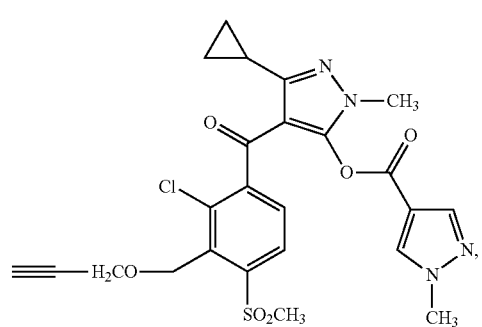
61
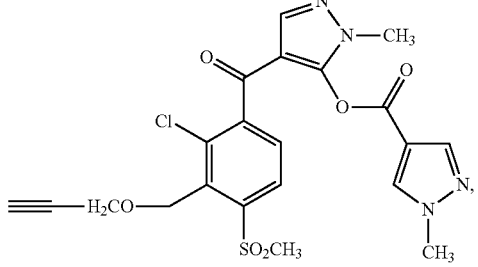
62
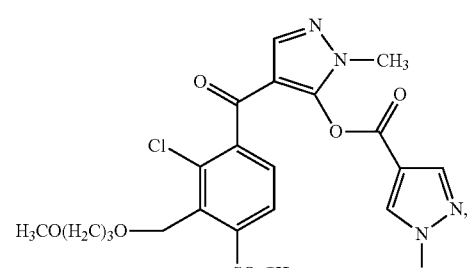
63
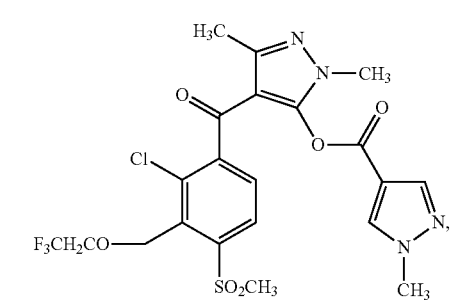
64
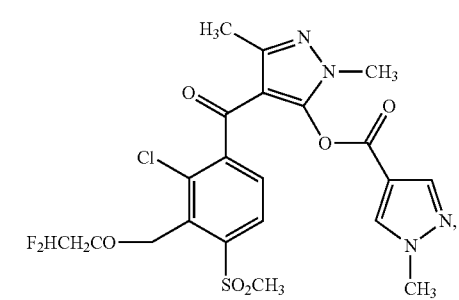
65
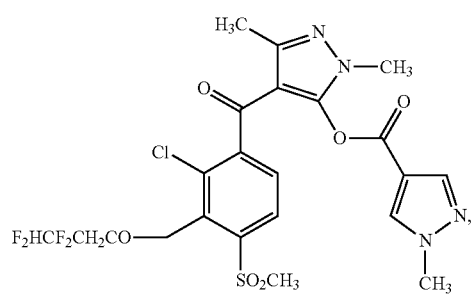

66
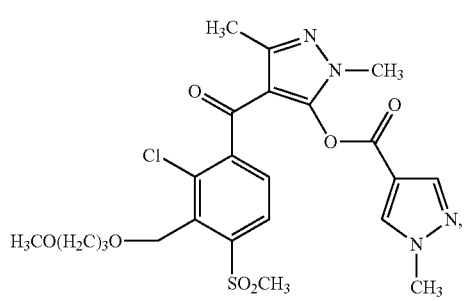
67
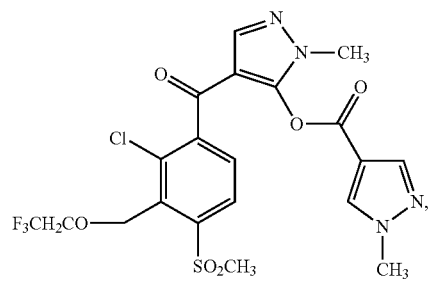
68
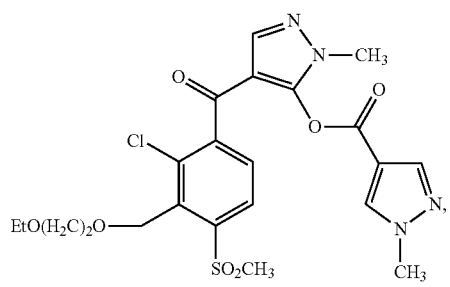
69
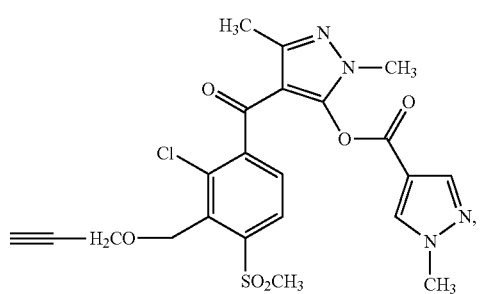
70
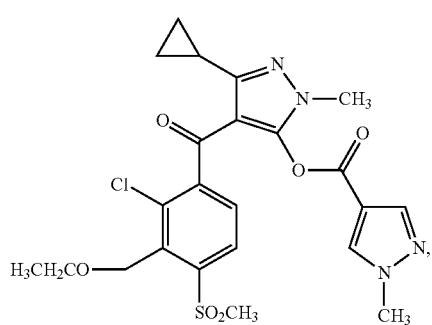
71
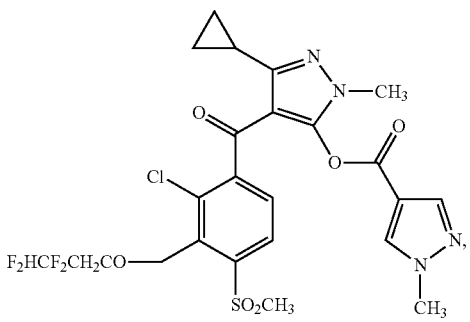
72
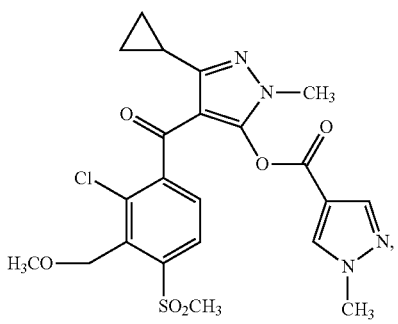
73
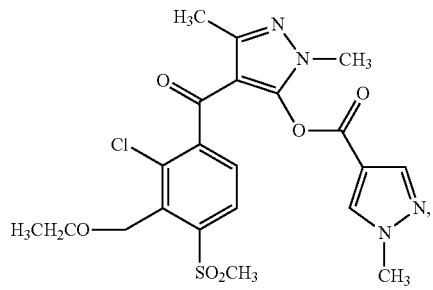
74
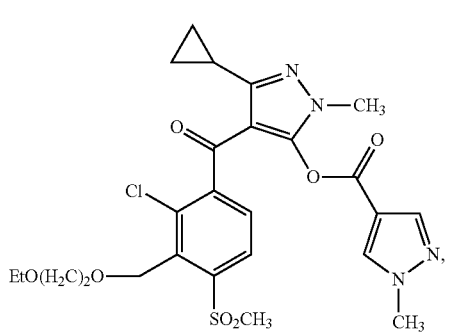
75
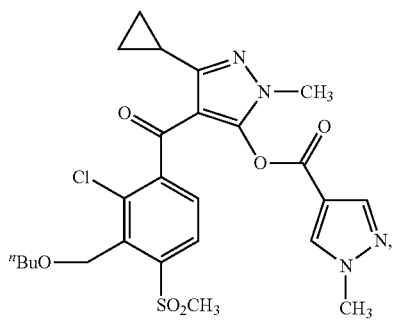

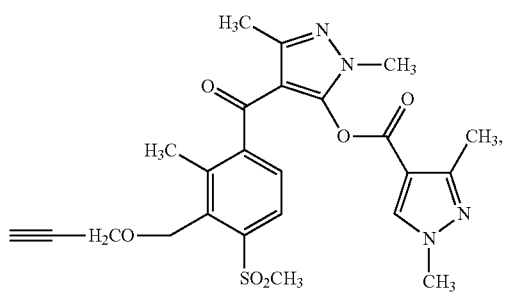
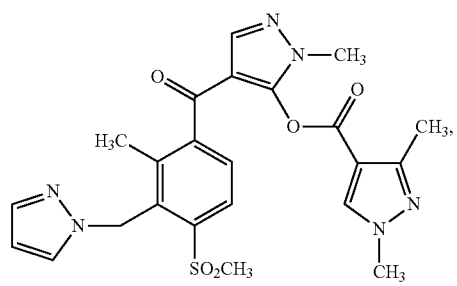
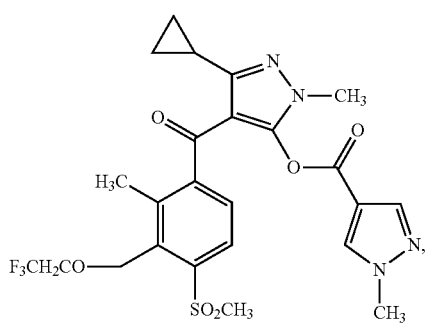
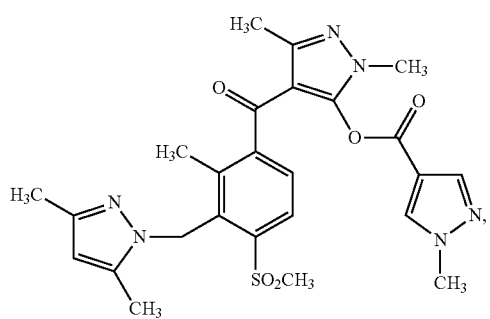
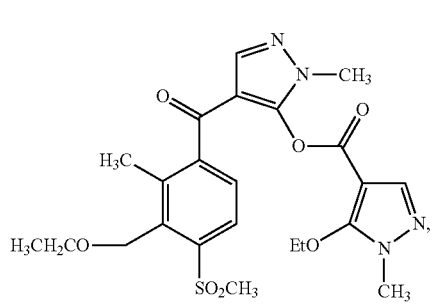
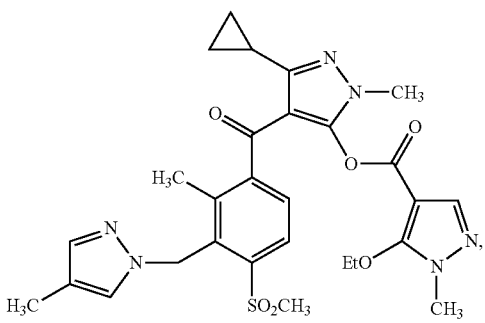
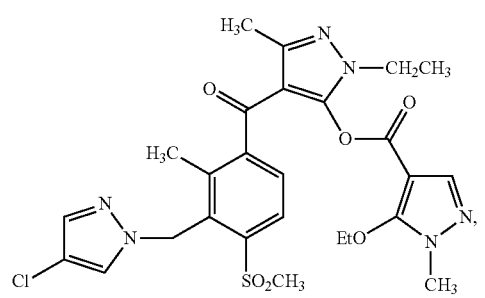
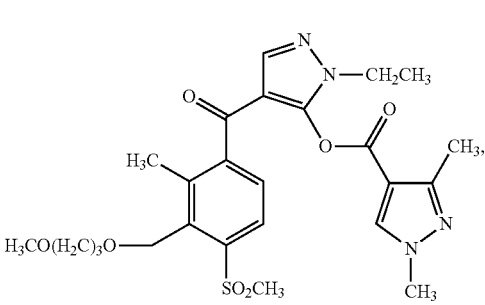
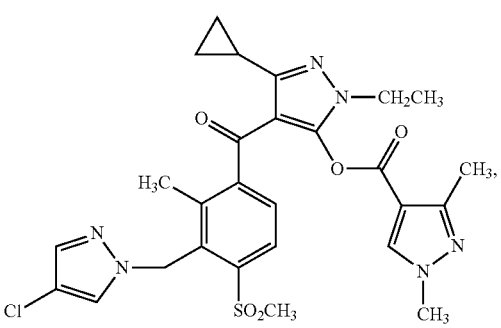
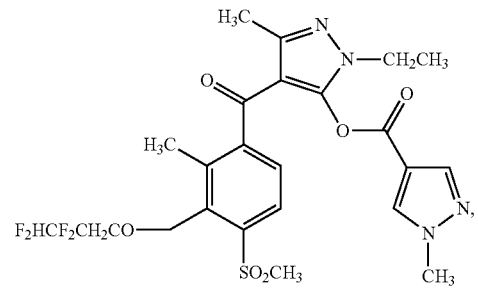

86
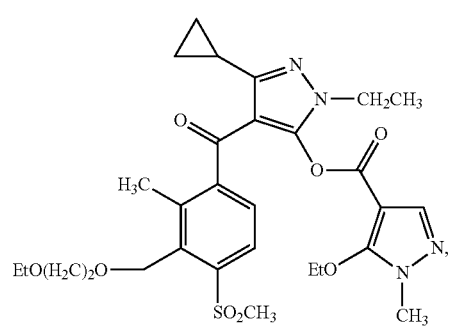
87
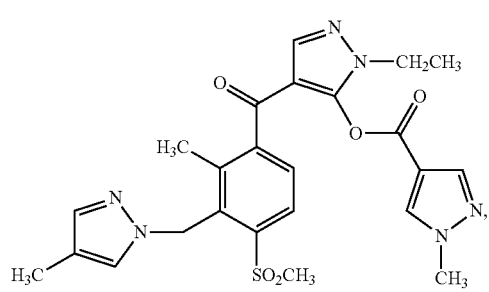
88
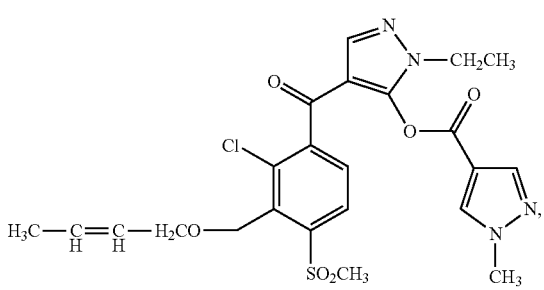
89
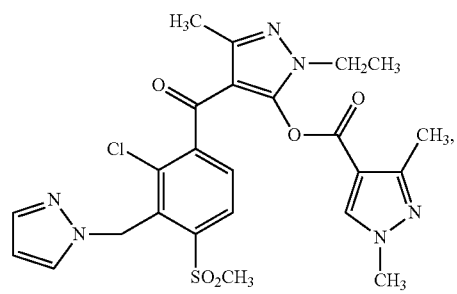
90
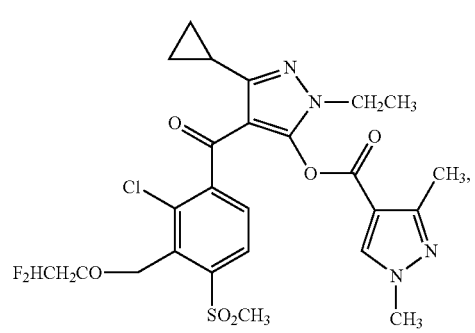
91
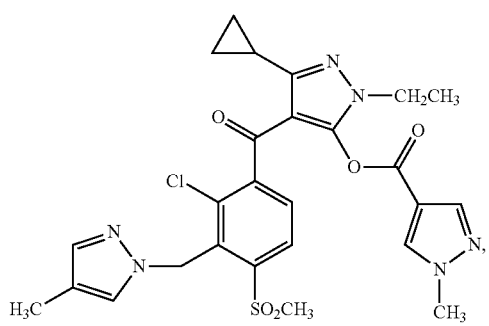
92
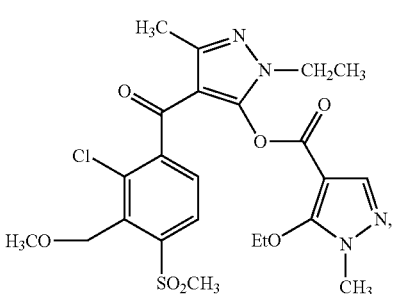
93
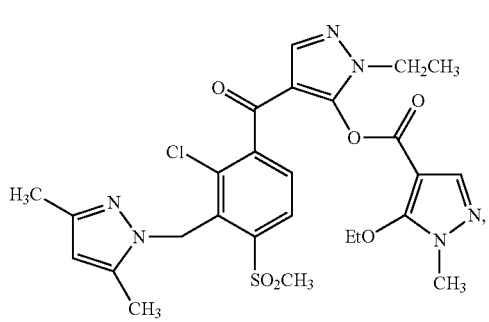
94
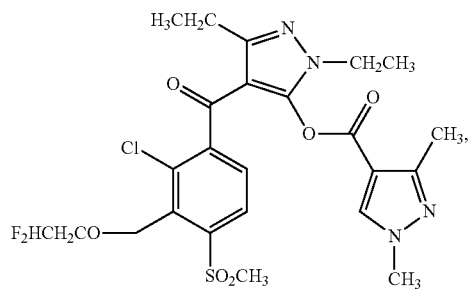
95
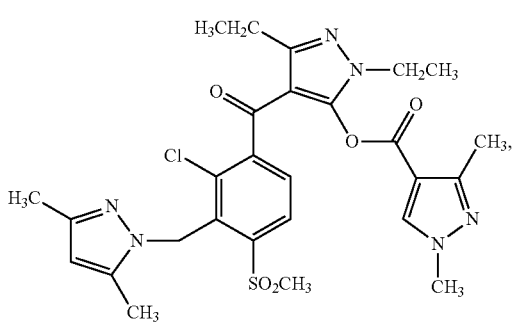

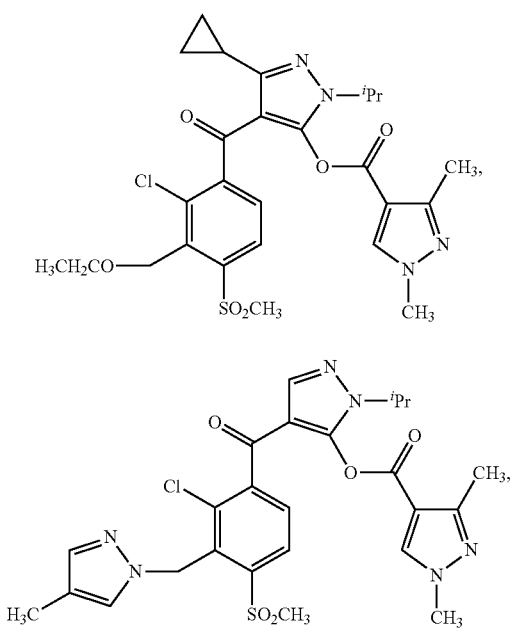
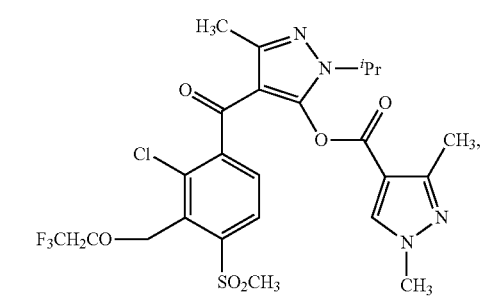
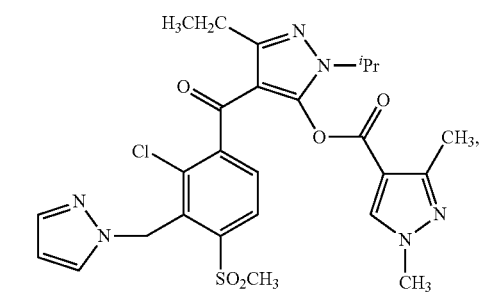
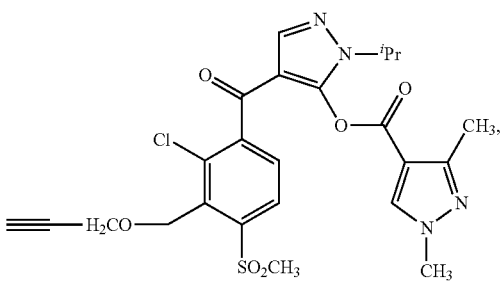
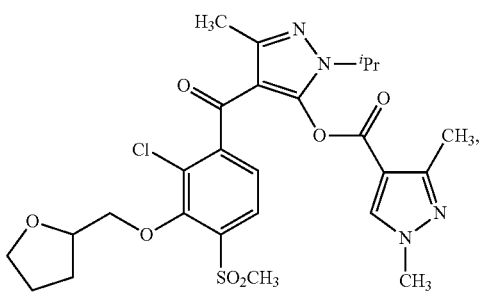
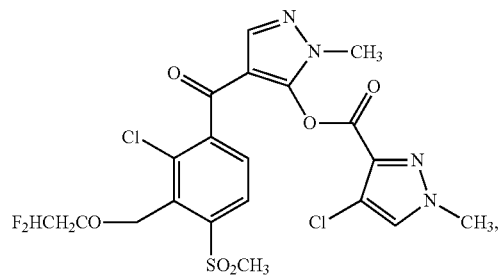
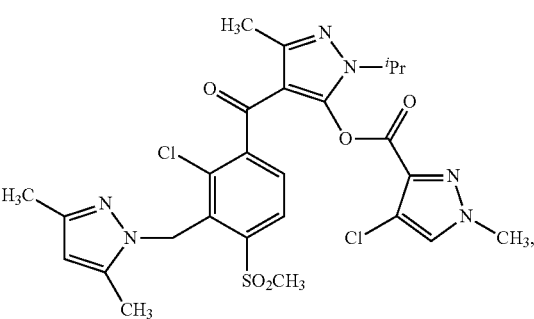
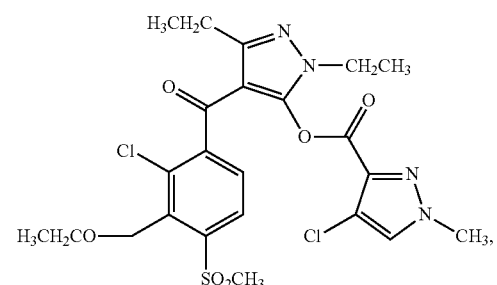
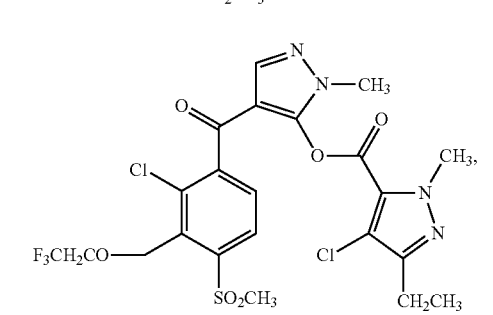

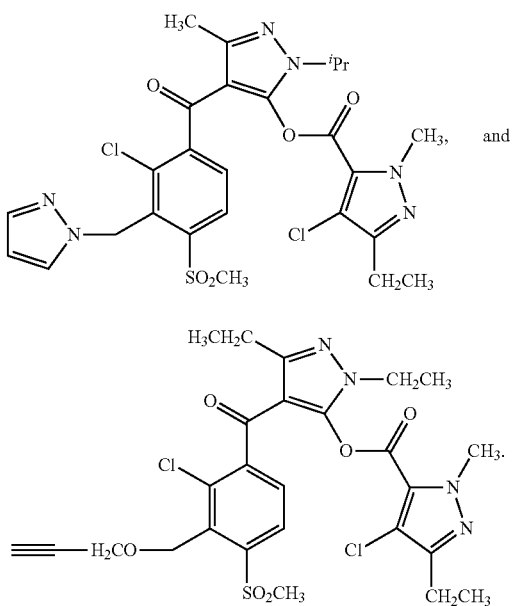

106

107

7. A method for preparing the pyrazole compound or the salt thereof according to claim 1, wherein a compound of formula (II')

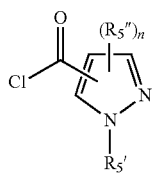

(II')

and a compound of formula (III')

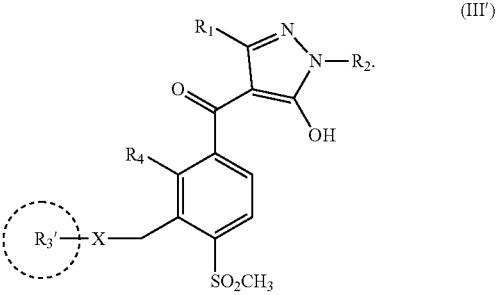

(III')

are subjected to an esterification reaction to obtain the pyrazole compound or the salt thereof.

8. The method according to claim 7, wherein the reaction is conducted in the presence of a solvent and an alkali at a temperature of −10 to 50° C. for 0.1-12 hours; the solvent is acetonitrile or dichloromethane, and the alkali is triethylamine or potassium carbonate.

9. The method according to claim 7, wherein the reaction is conducted at 0 to 20° C.

10. The method according to claim 7, wherein the reaction is conducted for 0.5-3 hours.

11. A method for controlling a harmful plant comprising applying an herbicidally effective amount of at least one pyrazole compound or the salt thereof according to claim 1 or an herbicidal composition comprising the pyrazole compound or the salt thereof to the plant or an area with the plant.

12. A method for controlling a harmful plant growing in a desirable crop, comprising applying an herbicidally effective amount of at least one pyrazole compound or the salt thereof according to claim 1 or an herbicidal composition comprising the pyrazole compound or the salt thereof to the plant or an area with the harmful plant.

13. The method according to claim 12, wherein the desirable crop is a genetically modified crop or a crop treated by a genome editing technique.

\* \* \* \* \*